(12) United States Patent
Dininno et al.

(10) Patent No.: US 6,207,823 B1
(45) Date of Patent: Mar. 27, 2001

(54) CARBAPENEM ANTIBACTERIAL COMPOUNDS, COMPOSITIONS CONTAINING SUCH COMPOUNDS AND METHODS OF TREATMENT

(75) Inventors: Frank P. Dininno, Old Bridge; Milton L. Hammond, Somerville, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/166,506

(22) Filed: Oct. 5, 1998

Related U.S. Application Data

(60) Provisional application No. 60/063,241, filed on Oct. 23, 1997.

(51) Int. Cl.$^7$ ................. C07D 477/14; A61P 31/04; A61K 31/407; A61K 31/428
(52) U.S. Cl. ..................... 540/210.03; 540/302
(58) Field of Search ................ 540/302; 514/210

(56) References Cited

U.S. PATENT DOCUMENTS

| | | | |
|---|---|---|---|
| 4,309,438 | 1/1982 | Christensen et al. | 424/274 |
| 4,479,947 | 10/1984 | Christensen | 424/203 |
| 5,138,048 | * 8/1992 | Tamburini et al. | 540/200 |
| 5,459,260 | * 10/1995 | Sendai et al. | 540/302 |

FOREIGN PATENT DOCUMENTS

0416953 * 3/1991 (EP) .

OTHER PUBLICATIONS

S. M. Schmitt et al. *J. Antibiotics*, 41(6), pp. 780–787 (1988).

*Bioorganic & Medicinal Chem.Ltrs*, 6, p. 2449, (1996.

* cited by examiner

*Primary Examiner*—Mark L. Berch
(74) *Attorney, Agent, or Firm*—Sylvia A. Ayler; Mark R. Daniel

(57) ABSTRACT

The present invention relates to tricyclic carbapenem antibacterial agents in which the carbapenem nucleus is fused to a 6 membered carbocyclic ring. The compound is further substituted with various substituent groups including at least one cationic group.

The compounds are represented by formula I:

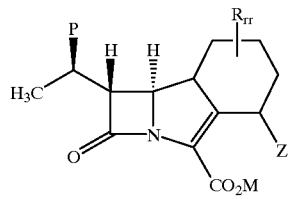

Pharmaceutical compositions and methods of use are also included.

26 Claims, No Drawings

CARBAPENEM ANTIBACTERIAL COMPOUNDS, COMPOSITIONS CONTAINING SUCH COMPOUNDS AND METHODS OF TREATMENT

This application claims the benefit of Provisional Application No. 60/063,241, filed Oct. 23, 1997.

BACKGROUND OF THE INVENTION

Infections caused by methicillin resistant *Staphylococcus aureus* (MRSA) and related gram positive pathogens are a growing medical concern. Vancomycin, a glycopeptide antibiotic, is currently the agent of choice for combating these infections which are predominantly encountered in hospital settings. With the increased usage of Vancomycin, the emergence of resistant stains of staphylococci is inevitable, and the first confirmed report of vancomycin resistance in *Staphylococcus epidermidis* was disclosed at the 36th Interscience Conference on Antimicrobial Agents and Chemotherapy, New Orleans, La., 1996. Consequently, there is a dire need to develop new agents with an alternative mode of action.

The present invention relates to novel tricyclic carbapenem compounds (trinems) in which the lipophilic side-chain necessary for anti-MRSA activity replaces the common simple ether based substitutents found in EPO 416,953, substituted carbon atoms found in EPO 507,313, and substituted amines found in WO9523149. The antibacterial compounds of the present invention thus comprise an important contribution to therapy for treating infections caused by these difficult to control pathogens. There is an increasing need for agents effective against such pathogens (MRSA/MRCNS) which are at the same time relatively free from undesirable side effects.

SUMMARY OF THE INVENTION

The present invention relates to anti-MRSA tricyclic carbapenem antibiotics containing aromatic based side-chains. The side-chain imparts MRS activity previously unassociated with the trinem skeleton.

The compounds of the invention are represented by formula I:

Z represents

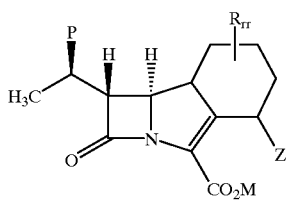

or a pharmaceutically acceptable salt thereof, wherein:

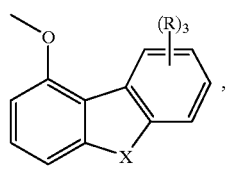

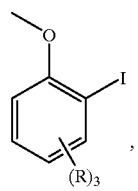

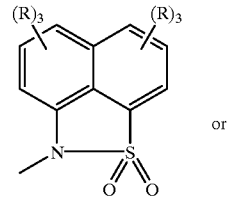

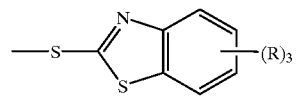

X represents $CH_2$, CHR, C=CHR, O, S, SO, $SO_2$, CO, $CO_2$, OCO, or NR;

$CO_2M$ represents a carboxylic acid, a carboxylate anion counter balanced by a counterion, a pharmaceutically acceptable ester group or a carboxylic acid protected by a protecting group;

Rrr represents hydrogen, —$C_{1-6}$ straight- or branched-chain alkyl, unsubstituted or substituted with one to four $R^i$ groups;

P represents hydrogen, hydroxyl, F or hydroxyl protected by a hydroxyl-protecting group;

each R is independently selected from: —$R^*$; —Q; hydrogen; halo; —CN; —$NO_2$; —$NR^aR^b$; —$OR^c$; —$SR^c$; —C(O)$NR^aR^b$; —C(O)$OR^h$; —S(O)$R^c$; —$SO_2R^c$; —$SO_2NR^aR^b$; —$NR^aSO_2R^b$; —C(O)$R^a$; OC(O)$R^a$; —OC(O)$NR^aR^b$; —$NR^aC(O)NR^bR^c$; —$NR^aCO_2R^h$; —$OCO_2R^h$; —$NR^aC(O)R^b$; —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups;

with the proviso that at least one R is present which contains at least one positive charge;

each $R^a$, $R^b$ and $R^c$ independently represents hydrogen, —$R^*$, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —C(NR$^e$)$NR^fR^g$; —$NR^eC(NH)NR^fR^g$; —$NR^eC(NR^f)R^g$; —$R^*$ or —Q;

$R^e$, $R^f$ and $R^g$ represent hydrogen; —$R^*$; —$C_{1-6}$ straight- or branched-chain alkyl unsubstituted or substituted with one to four $R^i$ groups;

or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$; —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3$–$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

Q is selected from the group consisting of:

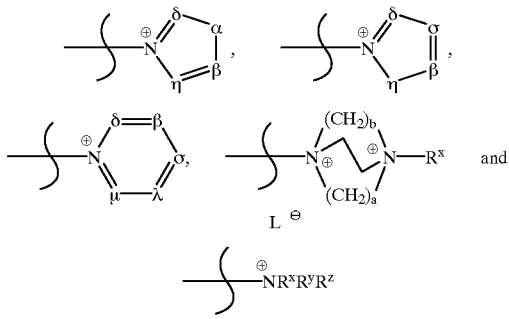

wherein:
a and b are 1, 2 or 3;
$L^-$ is a pharmaceutically acceptable counterion;
α represents O, S or $NR^s$;
β, δ, λ, μ and σ represent $CR^t$, N or $N^+R^s$, provided that no more than one of β, δ, λ, μ and σ is $N^+R^s$;
$R^*$ is selected from the group consisting of:

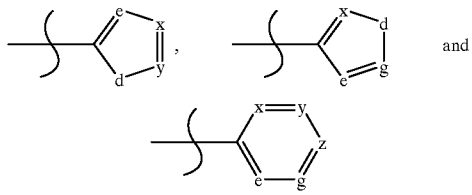

wherein:
d represents O, S or $NR^k$;
e, g, x, y and z represent $CR^m$, N or $N^+R^k$, provided that no more than one of e, g, x, y and z in any given structure represents $N^+R^k$;
$R^k$ represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;
each $R^m$ independently represents a member selected from the group consisting of: hydrogen; halo; —CN; —$NO_2$; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^n$; —$OCONR^nR^o$; —$NR^nCO_2R^h$; —$NR^nCONR^oR^h$;
—$OCO_2R^h$; —$CNR^nNR^oR^h$; —$NR^nCNHNR^oR^h$; —$NR^nC(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)Q$ where n and Q are as defined above;

$R^n$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

or $R^u$ and $R^v$ together with any intervening atoms represent a 4–6 membered saturated ring optionally interrupted by one or more of O, S, $NR^w$ or —C(O)—, said ring being unsubstituted or substituted with one to four $R^i$ groups;

each $R^w$ independently represents hydrogen; —C1–6 straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

or $R^h$ and $R^w$ taken together with any intervening atoms represent a 5–6 membered saturated ring, optionally interrupted by one or two of O, S, $SO_2$, NH or $NCH_3$;

$R^x$ represents hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteraryl, said phenyl and heteroaryl being optionally substituted with from one to four $R^i$ groups or with one to two $C_{1-3}$ straight- or branched- chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

or $R^x$ and $R^y$ together with any intervening atoms represent a 4–6 membered saturated ring optionally interrupted by O, S, $SO_2$, $NR^w$, $N^+R^hR^w$ or —C(O)—, unsubstituted or substituted with 1–4 $R^i$ groups, and when $R^x$ and $R^y$ together represent a 4–6 membered ring as defined above, $R^z$ is as defined above or $R^z$ represents an additional saturated 4–6 membered ring fused to the ring represented by $R^x$ and $R^y$ taken together, optionally interrupted by O, S, $NR^w$ or —C(O)—, said rings being unsubstituted or substituted with one to four $R^i$ groups.

Pharmaceutical compositions and methods of treatment are also included herein.

DETAILED DESCRIPTION OF THE INVENTION

The invention is described herein in detail using the terms defined below unless otherwise specified.

Carboxylate anion refers to a negatively charged group —COO—.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, selected from $R^d$ and $R^i$, as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 10.carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

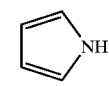 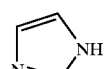 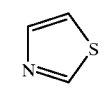
pyrrole (pyrrolyl)  imidazole (imidazolyl)  thiazole (thiazolyl)

  
oxazole (oxazolyl)  furan (furyl)  thiophene (thienyl)

-continued

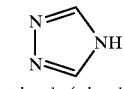 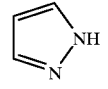 
triazole (triazolyl)  pyrazole (pyrazolyl)  isoxazole (isoxazolyl)

  
isothiazole (isothiazolyl)  pyridine (pyridinyl)  pyrazine (pyrazinyl)

  
pyridazine (pyridazinyl)  pyrimidine (pyrimidinyl)  triazine (triazinyl)

Heteroarylium refers to heteroaryl groups bearing a quaternary nitrogen atom and thus a positive charge. Examples include the following:

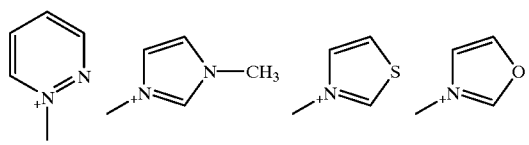

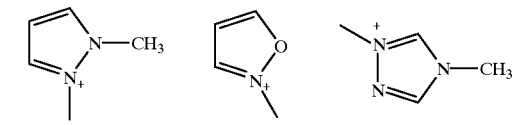

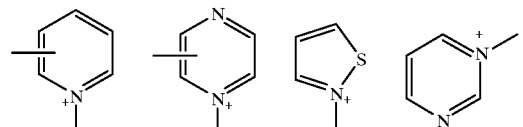

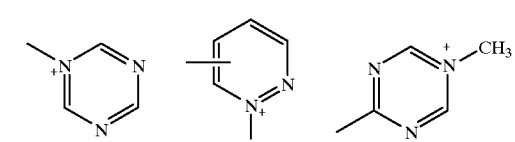

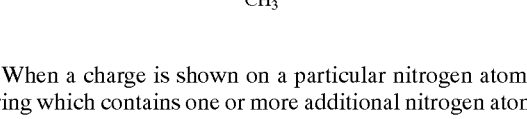

When a charge is shown on a particular nitrogen atom in a ring which contains one or more additional nitrogen atoms, it is understood that the charge may reside on a different nitrogen atom in the ring by virtue of charge resonance that occurs.

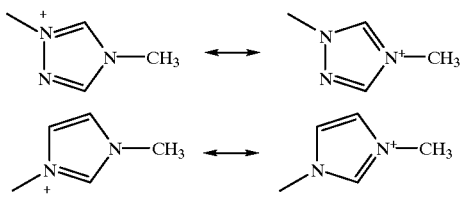

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e. g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

Alkoxy refers to $C_1$–$C_4$ alkyl—O—, with the alkyl group optionally substituted as described herein.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

In some of the carbapenem compounds of the present invention, M is a readily removable carboxyl protecting group, and/or P represents a hydroxyl which is protected by a hydroxyl- protecting group. Such conventional protecting groups consist of known groups which are used to protectively block the hydroxyl or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBS), phenacyl, p-methoxybenzyl, o-nitrobenzyl, p-methoxyphenyl, p-nitrobenzyl, 4-pyridylmethyl and t-butyl.

Examples of suitable hydroxyl protecting groups include triethylsilyl (TES), t-butyldimethylsilyl(TBS), t-butyldiphenylsilyl (DPTBS), o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

The carbapenem compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —$CO_2M$, which is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a protecting group (M represents a carboxyl protecting group). The pharmaceutically acceptable salts referred to above may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable. salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The pharmaceutically acceptable esters are such as would be readily apparent to a medicinal chemist, and include, for example, those described in detail in U.S. Pat. No. 4,309, 438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and may be suitable for oral administration, due to good absorption through the stomach or intenstinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

L⁻ can be present or absent as necessary to maintain the appropriate charge balance. When present, L⁻ represents a pharmaceutically acceptable counterion. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when L⁻ represents a specie with more than one negative charge, such as malonate, tartrate or ethylenediamine-tetraacetate (EDTA), an appropriate number of carbapenem molecules can be found in association therewith to maintain the overall charge balance and neutrality.

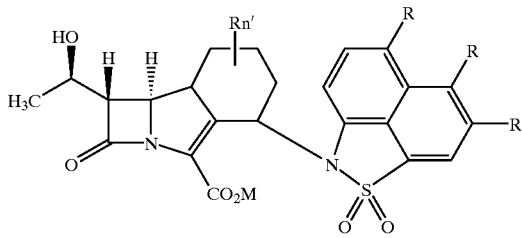

A subset of compounds of formula Ia which is of interest relates to those compounds where $CO_2M$ represents a carboxylate anion. Hence, M in this instance represents a negative charge which will be balanced by a positively charged group, such as in the positively charged R group. Likewise, if the positively charged R group contains more than one positive charge, a negatively charged counterion may be present which in combination with the carboxylate anion, provides overall charge neutrality.

Another subset of compounds of formula Ia which is of interest relates to compounds wherein one R represents a group which contains a positively charged moiety, and the remaining R groups are selected from hydrogen and $C_{1-6}$ straight or branched chain alkyl, unsubstituted or substituted with one to four $R^d$ groups. More particularly, this subset of interest includes compounds of formula Ia wherein one R represents a group containing a positively charged moiety and the remaining R groups are hydrogen.

With respect to the positively charged moiety or moieties that are contained in one or more R groups, it is preferred that from 1–3 positive charges be present, and most preferably two positive charges be present, balanced by the carboxylate anion and a negatively charged counterion.

Another subset of compounds which is of interest is represented by formula Ia wherein one R group represents a —$C_{1-6}$ straight or branched chain alkyl group, substituted with one to four $R^d$ groups, wherein one $R^d$ group represents —$R^*$ or Q. Hence, a positively charged moiety —$R^*$ or Q is attached to an alkyl group.

Another group of compounds of interest is represented by formula Ia wherein Q is selected from the group consisting of:

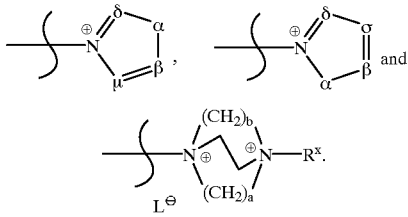

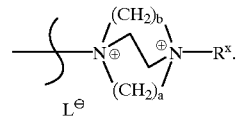

More particularly, the group of compounds which is of interest is represented by formula I wherein Q represents:

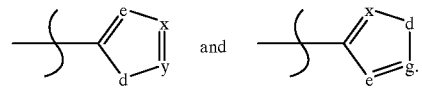

Within this subset of compounds, L⁻, a and b are as originally defined, and $R^x$ is as originally defined, and represents a member selected from the group consisting of: hydrogen or a $C_{1-8}$ straight- or branched- chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched- chain alkyl groups, said alkyl groups being unsubstituted or substituted with one to four $R^i$ groups.

Another group of compounds of interest is represented by formula I wherein Q represents —$N^+R^xR^yR^z$, wherein $R^x$, $R^y$ and $R^z$ are as originally defined.

Another group of compounds of interest is represented by formula I wherein one $R^*$ group is present and is selected from:

Within this subset, d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

A preferred subset of compounds of formula I which is of particular interest relates to compounds represented by formula I wherein:
  Z represents a*;
  $CO_2M$ represents a carboxylate anion;
  one R group which is attached to the naphthosultam platform contains at least one positively charged moiety, and the remaining R groups are selected from hydrogen and $C_{1-6}$ straight or branched chain alkyl, unsubstituted or substituted with one to four $R^d$ groups;
  $R^d$ is as originally defined;
  $R^h$ represents hydrogen or a $C_{1-6}$ straight or branched chain alkyl group;

Q is selected from the group consisting of:

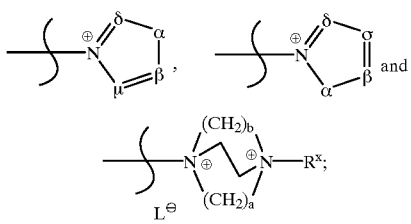

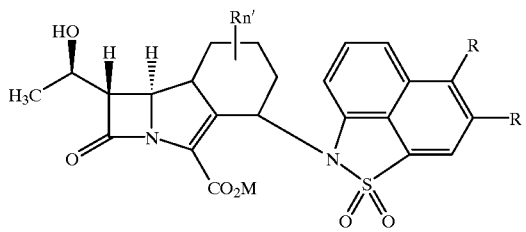

wherein L⁻, a and b are as originally defined, and $R^x$ represents a member selected from the group consisting of: hydrogen or a $C_{1-8}$ straight- or branched- chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $CO_2R^w$, $OC(O)R^w$, OC(O)$NR^hR^w$, $NR^hC(O)R^w$, $NR^hC(O)NR^hR^w$, phenyl or heteroaryl, said phenyl or heteroaryl group being optionally substituted with from one to four $R^i$ groups or with one to two $C_{1-3}$ straight- or branched- chain alkyl groups, said alkyl groups being unsubstituted or substituted with one to four $R^i$ groups;

$R^*$ is selected from:

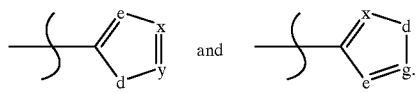

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Within this subset, all other variables are as originally defined with respect to formula I.

Another more preferred subset of compounds is represented by formula Ib:

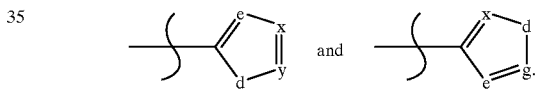

Ib or a pharmaceutically acceptable salt thereof, wherein:

$CO_2M$ represents a carboxylate anion;

one R group is attached to the naphthosultam platform which contains a positively charged moiety, and the other R group is selected from hydrogen and $C_{1-6}$ straight or branched chain alkyl, unsubstituted or substituted with one to four $R^d$ groups;

$R^d$ is as originally defined;

Q is selected from the group consisting of:

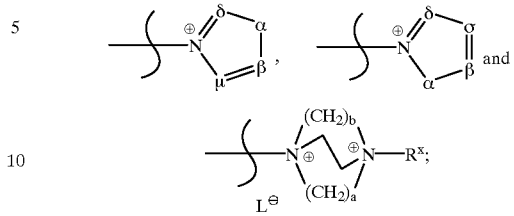

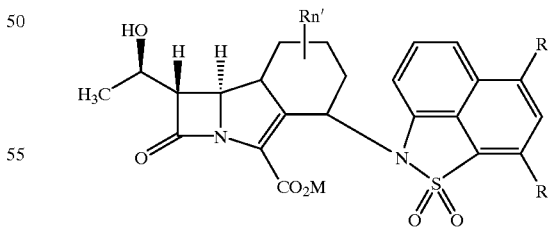

wherein L⁻, a and b are as originally defined, and $R^x$ represents a member selected from the group consisting of: hydrogen or a $C_{1-8}$ straight- or branched- chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight- or branched- chain alkyl groups, said alkyl groups being unsubstituted or substituted with one to four $R^i$ groups;

$R^h$ represents hydrogen or a $C_{1-6}$ straight or branched chain alkyl group;

$R^w$ is as originally defined;

$R^*$ is selected from:

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen. Within this subset, all other variables are as originally defined with respect to formula I.

Another more preferred subset of compounds is represented by formula Ic:

Ic or a pharmaceutically acceptable salt thereof, wherein:

$CO_2M$ represents a carboxylate anion;

one R group is attached to the naphthosultam platform which contains a positively charged moiety, and the other R group is selected from hydrogen, halo and $C_{1-6}$ straight or branched chain alkyl, unsubstituted or substituted with one to four $R^d$ groups;

$R^d$ is as originally defined;

Q is selected from the group consisting of:

[chemical structures]

wherein $L^-$, a and b are as originally defined, and $R^x$ represents a member selected from the group consisting of: hydrogen or a $C_{1-8}$ straight- or branched- chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

$R^h$ represents hydrogen or a $C_{1-6}$ straight or branched chain alkyl group;

$R^w$ is as originally defined;

$R^*$ is selected from:

[chemical structures]

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen. Within this subset, all other variables are as originally defined with respect to formula I.

Another more preferred subset of compounds is represented by formula Id:

Id

[chemical structure]

or a pharmaceutically acceptable salt thereof, wherein:

$CO_2M$ represents a carboxylate anion;

one R group is attached to the naphthosultam platform which contains a positively charged moiety, and the other R group is selected from hydrogen, halo and $C_{1-6}$ straight or branched chain alkyl, unsubstituted or substituted with one to four $R^d$ groups;

$R^d$ is as originally defined;

Q is selected from the group consisting of:

[chemical structures]

wherein $L^-$, a and b are as originally defined, and $R^x$ represents a member selected from the group consisting of: hydrogen or a $C_{1-8}$ straight- or branched- chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight- or branched- chain alkyl groups, said alkyl groups being unsubstituted or substituted with one to four $R^i$ groups;

$R^h$ represents hydrogen or a $C_{1-6}$ straight or branched chain alkyl group;

$R^w$ is as originally defined;

$R^*$ is selected from:

[chemical structures]

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen. Within this subset, all other variables are as originally defined with respect to formula I.

Still more preferably, the present invention relates to a compound represented by formula Ia wherein the R group at position 4 represents a positively charged moiety, and the R groups at position 3 and 5 represent hydrogen.

In particular, such compounds can be represented by formula Ie:

Ie

[chemical structure]

or a pharmaceutically acceptable salt thereof, wherein:

R contains a positively charged moiety selected from the group consisting of: —$R^*$, Q, and a $C_{1-6}$ straight or branched alkyl chain substituted with one $R^d$ group;

$R^d$ is independently selected —$R^*$ or Q;
Q is selected from the group consisting of:

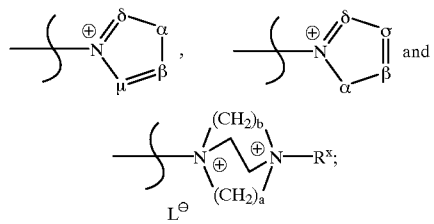

wherein $L^-$, a and b are as originally defined, and $R^x$ represents a member selected from the group consisting of: hydrogen or a $C_{1-8}$ straight- or branched- chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

$R^*$ is selected from:

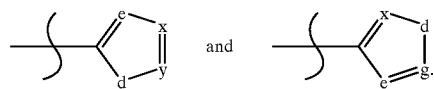

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Likewise, such compounds can be represented by formula If:

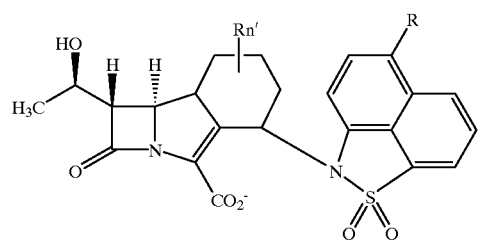

or a pharmaceutically acceptable salt thereof, wherein:

R contains a positively charged moiety selected from the group consisting of: —$R^*$, Q, and a $C_{1-6}$ straight or branched alkyl chain substituted with one $R^d$ group;

$R^d$ is independently selected —$R^*$ or Q;
Q is selected from the group consisting of:

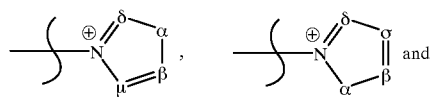

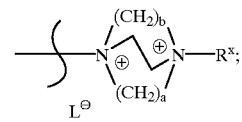

wherein $L^-$, a and b are as originally defined, and Rx represents a member selected from the group consisting of: hydrogen or a $C_{1-8}$ straight- or branched- chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^{hRw}$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

$R^*$ is selected from:

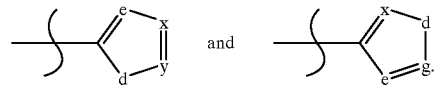

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

A still more preferred subset of compounds of the invention is represented by formula Ie wherein:
R represents

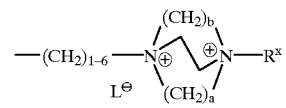

and $R^x$, a, b and $L^-$ are as originally defined.

Another more preferred subset of compounds of the invention is represented by formula Ig:

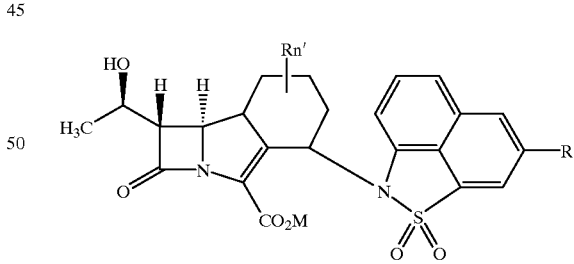

wherein:
R represents

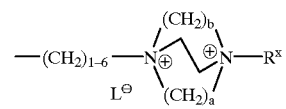

and $R^x$, a, b and $L^-$ are as originally defined.

Another more preferred subset of compounds of the invention are presented by formula Ih:

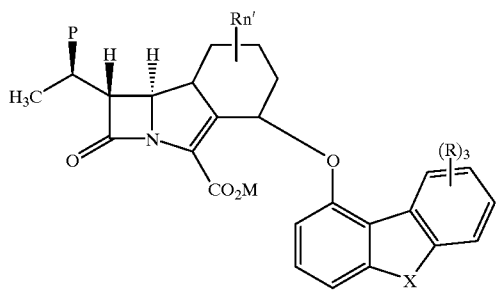

Ih wherein:

X represents $CH_2$, CHR, C=CHR, O, S, SO, $SO_2$, CO, $CO_2$, OCO, NR;

$CO_2M$ represents a carboxylate anion;

$R^d$ is as originally defined;

$R^h$ represents hydrogen or a $C_{1-6}$ straight or branched chain alkyl group;

Q is selected from the group consisting of:

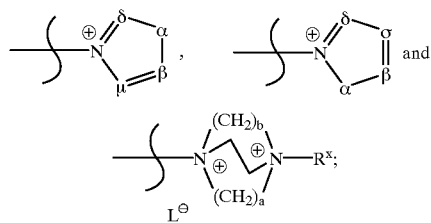

wherein $L^-$, a and b are as originally defined, and $R^x$ represents a member selected from the group consisting of: hydrogen or a $C_{1-8}$ straight- or branched- chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight- or branched- chain alkyl groups, said alkyl groups being unsubstituted or substituted with one to four $R^i$ groups;

$R^*$ is selected from:

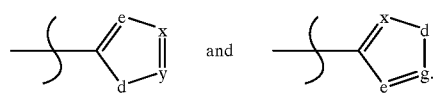

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Within this subset, all other variables are as originally defined with respect to formula I.

Another more preferred subset of compounds of the invention are presented by formula Ii:

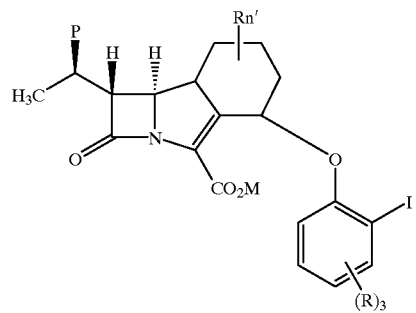

Ii $CO_2M$ represents a carboxylate anion;

$R^d$ is as originally defined;

$R^h$ represents hydrogen or a $C_{1-6}$ straight or branched chain alkyl group;

Q is selected from the group consisting of:

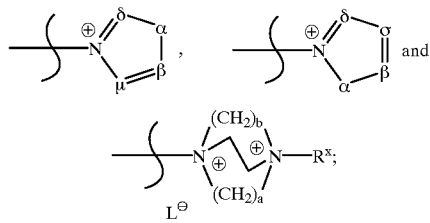

wherein $L^-$, a and b are as originally defined, and $R^x$ represents a member selected from the group consisting of: hydrogen or a $C_{1-8}$ straight- or branched- chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight- or branched- chain alkyl groups, said alkyl groups being unsubstituted or substituted with one to four $R^1$ groups;

$R^*$ is selected from:

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Within this subset, all other variables are as originally defined with respect to formula I.

Another more preferred subset of compounds of the invention are presented by formula Ij:

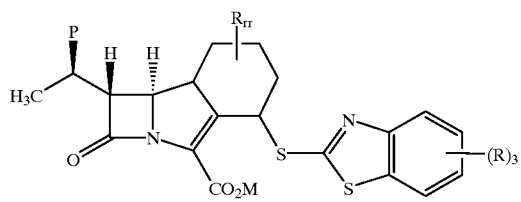

wherein:
$CO_2M$ represents a carboxylate anion;
$R^d$ is as originally defined;
$R^h$ represents hydrogen or a $C_{1-6}$ straight or branched chain alkyl group;
Q is selected from the group consisting of:

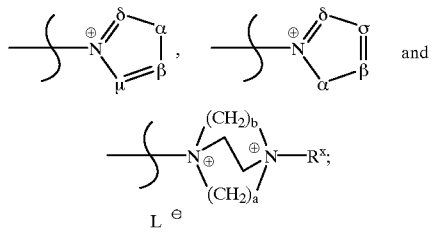

wherein $L^-$, a and b are as originally defined, and $R^x$ represents a member selected from the group consisting of: hydrogen or a $C_{1-8}$ straight- or branched- chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight- or branched- chain alkyl groups, said alkyl groups being unsubstituted or substituted with one to four $R^i$ groups;

$R^*$ is selected from:

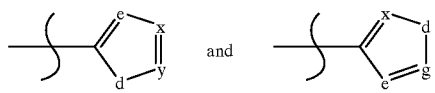

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Within this subset, all other variables are as originally defined with respect to formula I.

Representative examples of compounds of the invention are shown below. The invention is intended, where appropriate, to include protonated amines protonated at the appropriate pH, e.g., pH 7.

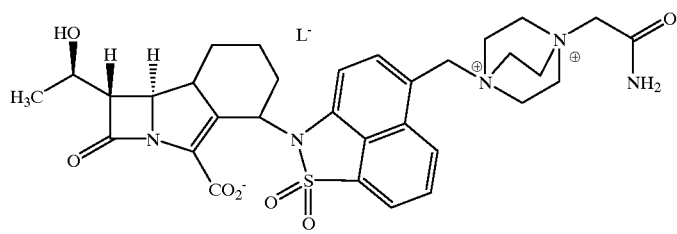

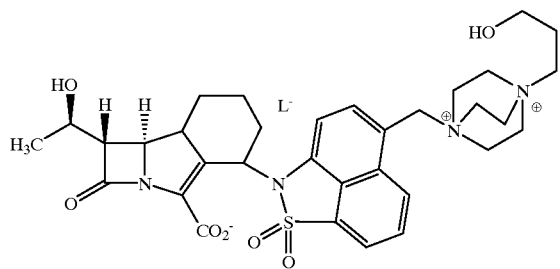

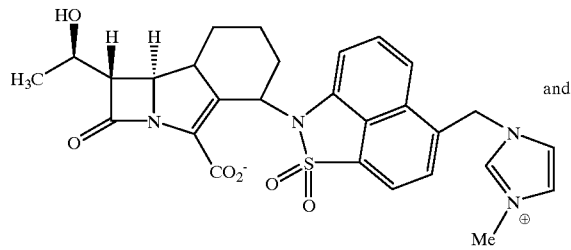

-continued
E-4
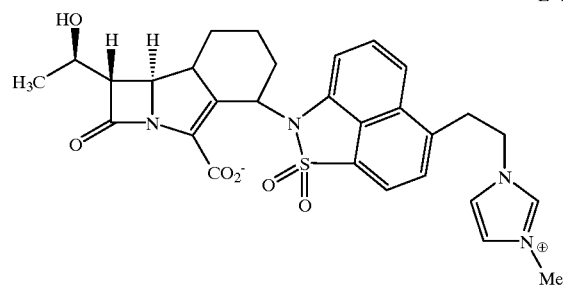
E-5
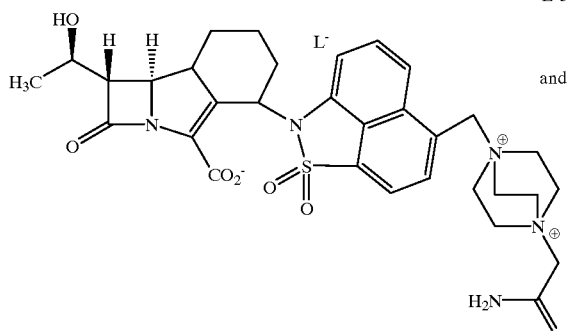
and
E-7
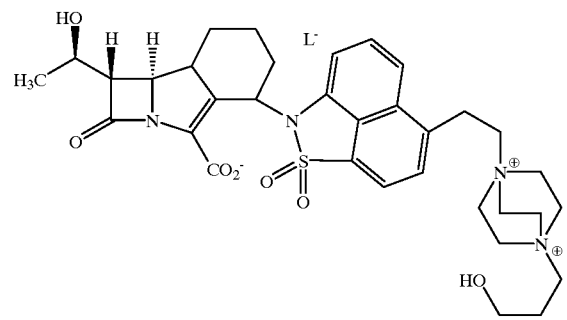
E-6
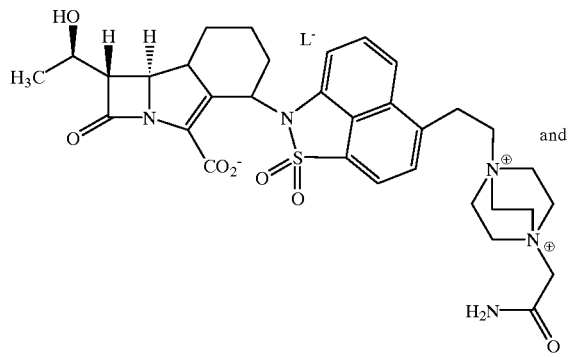
and
E-8
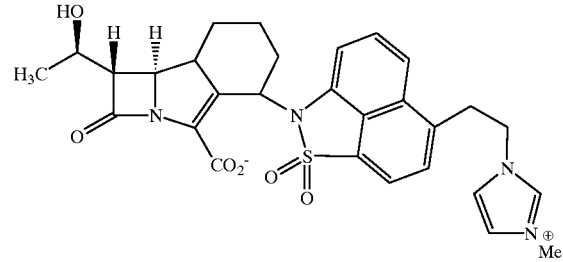
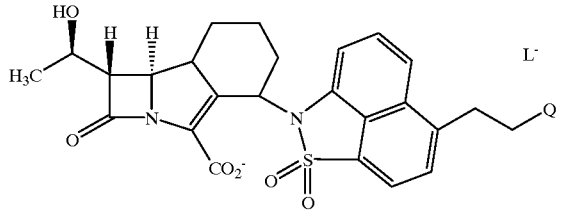
L⁻
| # | Q |
|---|---|
| 9 | 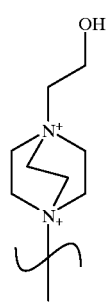 |
| 10 | 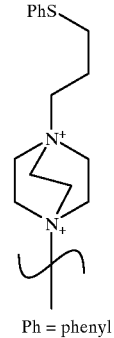  Ph = phenyl |

TABLE-continued

| # | Q |
|---|---|
| 11 | (1-(2-fluoroethyl)-DABCO structure) |
| 12 | (1-(3-fluoropropyl)-DABCO structure) |
| 13 | (1-(3-ureidopropyl)-DABCO structure) |
| 14 | (1-(3-carbamoyloxypropyl)-DABCO structure) |
| 15 | (1-(N-methylcarbamoylmethyl)-piperazinium structure) |
| 16 | (1-(N,N-dimethylcarbamoylmethyl)-DABCO structure) |
| 17 | (1-methyl-DABCO structure) |
| 18 | (1-(methylthiomethyl)-DABCO structure) |
| 19 | (1-(methylsulfinylmethyl)-DABCO structure) |

TABLE-continued

| # | Q |
|---|---|
| 20 | (1-methylsulfonylmethyl-1,4-diazoniabicyclo[2.2.2]octane) |
| 21 | (1-phenylthiomethyl-1,4-diazoniabicyclo[2.2.2]octane) |
| 22 | (1-phenylsulfonylmethyl-1,4-diazoniabicyclo[2.2.2]octane) |
| 23 | (1-(3-hydroxypropyl)pyrazinium) |

TABLE-continued

| # | Q |
|---|---|
| 24 | (1-(2-aminoethyl)-1,4-diazoniabicyclo[2.2.2]octane) |
| 25 | (1-(3-aminopropyl)-1,4-diazoniabicyclo[2.2.2]octane) |
| 26 | (1-(phenylcarbamoylmethyl)-1,4-diazoniabicyclo[2.2.2]octane) |
| 27 | (pyridinium) |

TABLE-continued

| # | Q |
|---|---|
| 28 | [imidazolium with N-CH2CH2OH substituent] |
| 29 | [quinuclidinium] |
| 30 | [thiazolium] |
| 31 | [oxazolium] |
| 32 | [triethylammonium] |
| 33 | [carbapenem core with (1-hydroxyethyl) substituent, fused naphthosultam bearing –(CH2)3–Q side chain; CO2⁻] |
| 34 | [DABCO-based bis-quaternary with –CH2C(O)NH2; L⁻] |

TABLE-continued

| # | Q |
|---|---|
| 35 | [DABCO-based bis-quaternary with –(CH2)3OH; L⁻] |
| 36 | [1-methylimidazolium] |
| 37 | [carbapenem core with (1-hydroxyethyl) substituent, fused naphthosultam bearing –CH2–Q; CO2⁻; L⁻] |
| 38 | [DABCO-based bis-quaternary with –CH2C(O)NH2] |
| 39 | [DABCO-based bis-quaternary with –(CH2)3OH] |

TABLE-continued

| # | Q |
|---|---|
| 40 | (N+-CH2CH2F bicyclic diamine, N+ attached) |
| 41 | (1-methylimidazolium) |
| 42 | (1-(2-hydroxyethyl)imidazolium) |
| 43 | (thiazolium) |

TABLE-continued

| # | Q |
|---|---|
| 45 | (N+-CH2C(O)NH2 bicyclic diamine, L−) |
| 46 | (N+-CH2CH2CH2OH bicyclic diamine, L−) |
| 47 | (1-methylimidazolium) |
| 49 | (N+-CH2C(O)NH2 bicyclic diamine) |

TABLE-continued
| # | Q |
|---|---|
| 50 | 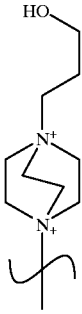 |
| 51 | 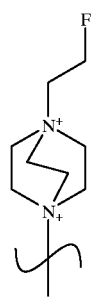 |
|  | 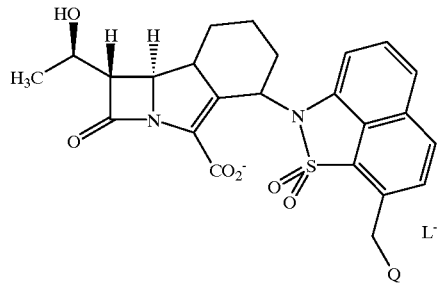 |
| 52 | 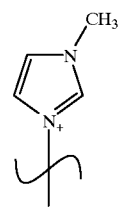 |
| 53 | 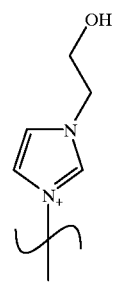 |
TABLE-continued
| # | Q |
|---|---|
| 54 | 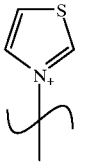 |
|  | 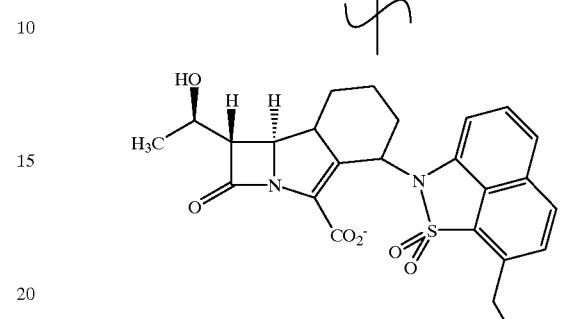 |
| 56 | 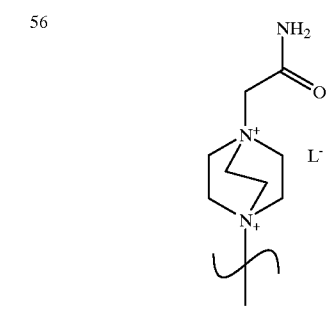 |
| 57 | 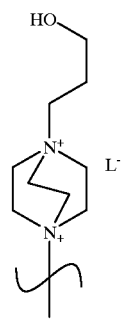 |
| 58 | 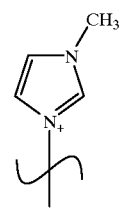 |
|  | 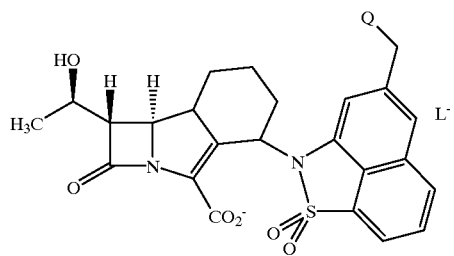 |

TABLE-continued
| # | Q |
|---|---|
| 60 | 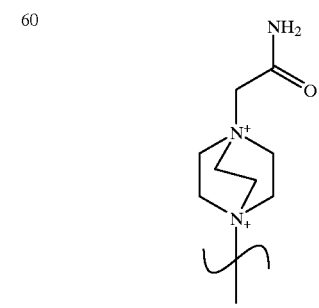 |
| 61 | 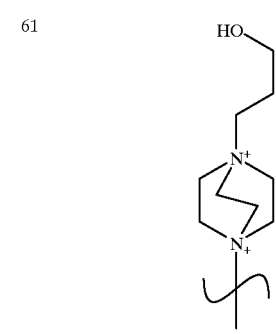 |
| 62 | 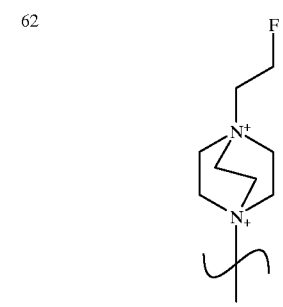 |
| | 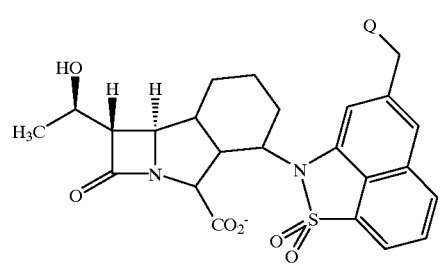 |
| 63 | |
TABLE-continued
| # | Q |
|---|---|
| 64 | 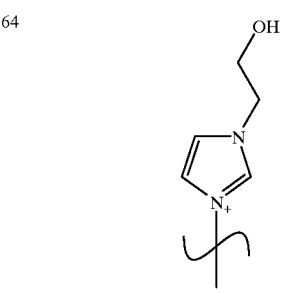 |
| 65 | 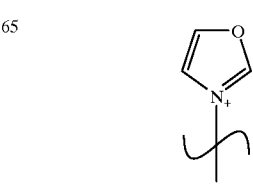 |
| | 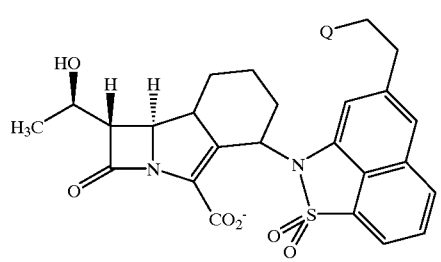 |
| 67 | 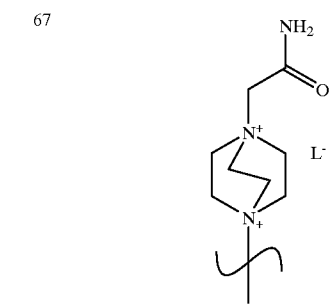 |
| 68 | 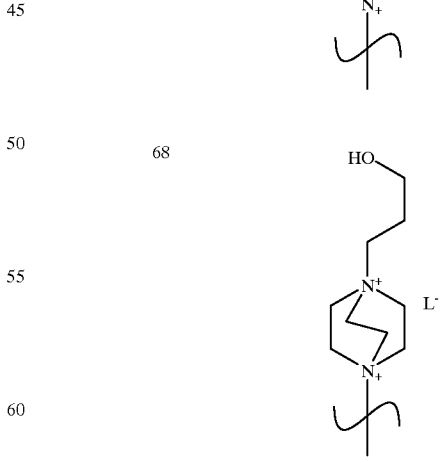 |

TABLE-continued
| # | Q |
|---|---|
| 69 | 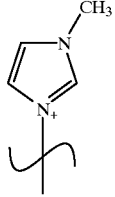 |
| | 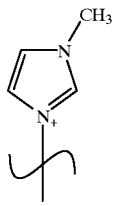 |
| 74 | 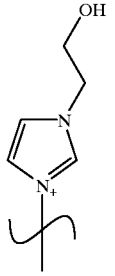 |
| 75 | 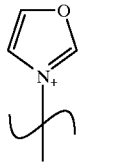 |
| 76 | 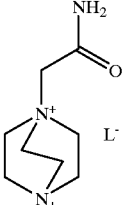 |
| | 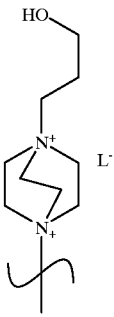 |
TABLE-continued
| # | Q |
|---|---|
| 78 | 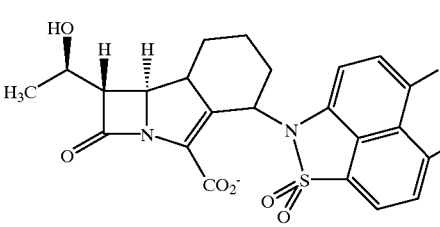 |
| 79 | |
| 80 | |
| | |
| 82 | |

US 6,207,823 B1
TABLE-continued
| # | Q |
|---|---|
| 83 | 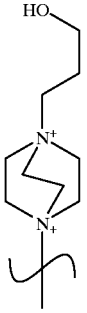 |
| 84 | 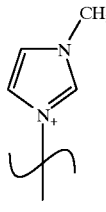 |
| 86 | 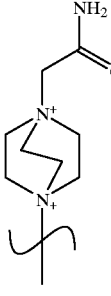 |
| 87 | 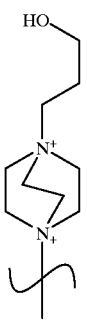 |
TABLE-continued
| # | Q |
|---|---|
| 88 | 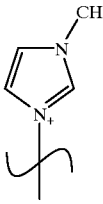 |
| 90 | 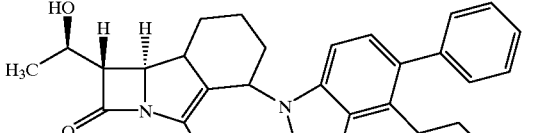 |
| 91 | 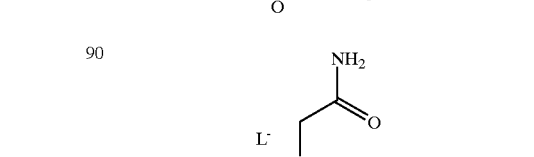 |
| 92 |  |
| R₂ | Q |
|---|---|

TABLE-continued

| # | Q |
|---|---|
| Cl | [structure: -CH2-C(=O)-NH2 on N+ of diazabicyclo cage, other N+ with wavy bond] |
| CH3 | [structure: -CH2-C(=O)-NH2 on N+ of diazabicyclo cage, other N+ with wavy bond] |
| Cl | [structure: HO-(CH2)3- on N+ of diazabicyclo cage, other N+ with wavy bond] |
| CH3 | [structure: HO-(CH2)3- on N+ of diazabicyclo cage, other N+ with wavy bond] |

TABLE-continued

| # | Q |
|---|---|
| Cl | [structure: -CH2-C(=O)-NH2 on N+ of diazabicyclo cage, other N+ with wavy bond] |
| CH3 | [structure: -CH2-C(=O)-NH2 on N+ of diazabicyclo cage, other N+ with wavy bond] |
| Cl | [structure: HO-(CH2)3- on N+ of diazabicyclo cage, other N+ with wavy bond] |
| CH3 | [structure: HO-(CH2)3- on N+ of diazabicyclo cage, other N+ with wavy bond] |

Ph = phenyl wherein Q is as defined in the tables and L⁻ represents a pharmaceutically acceptable counterion.

-continued
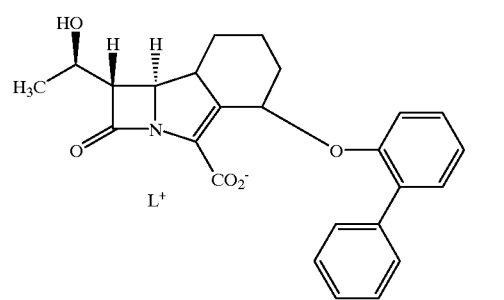
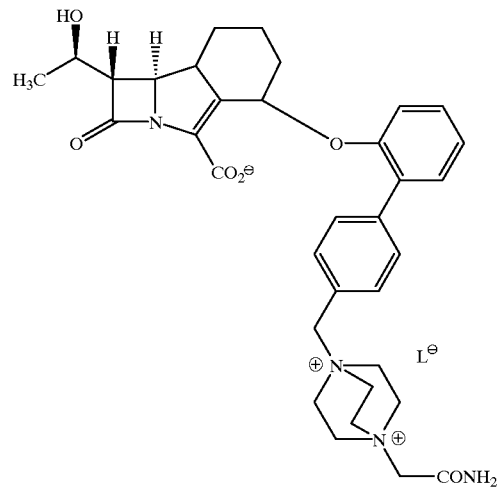
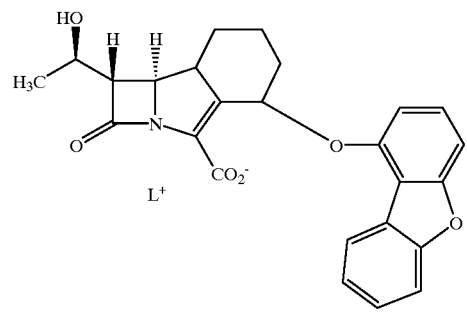
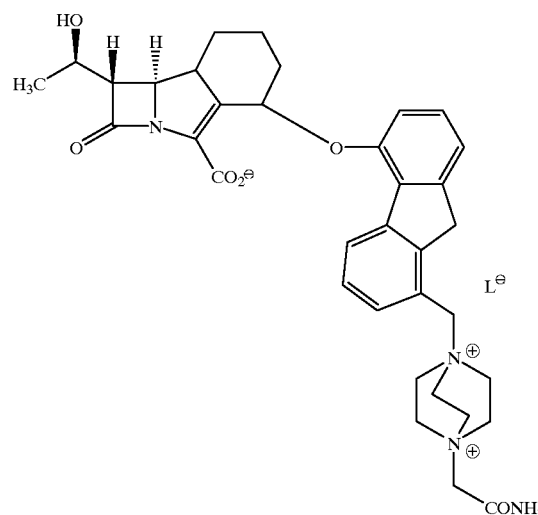
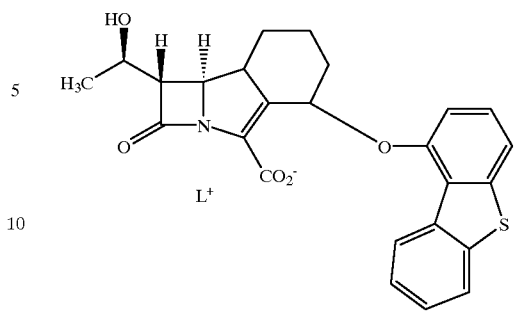
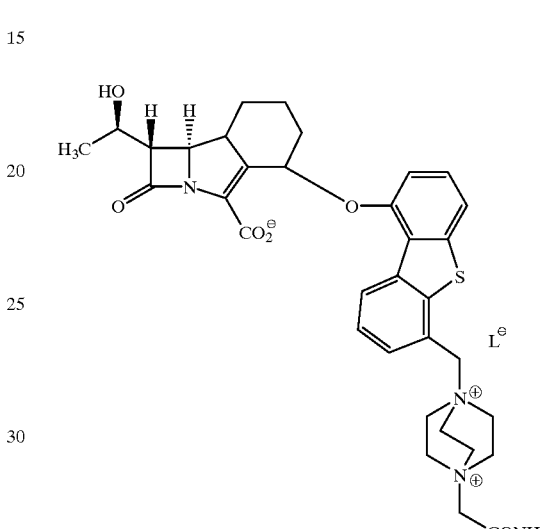
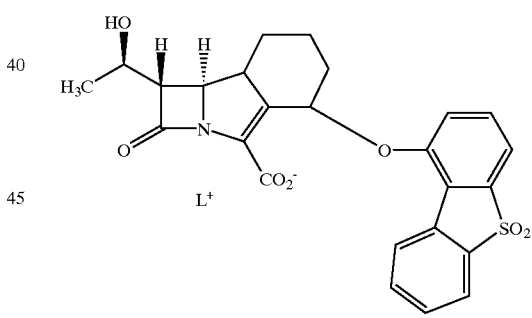
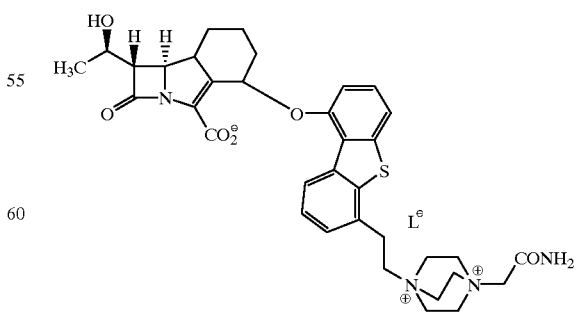

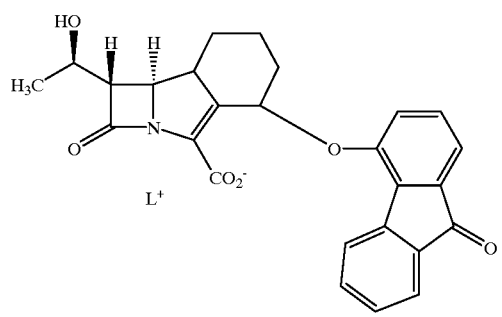
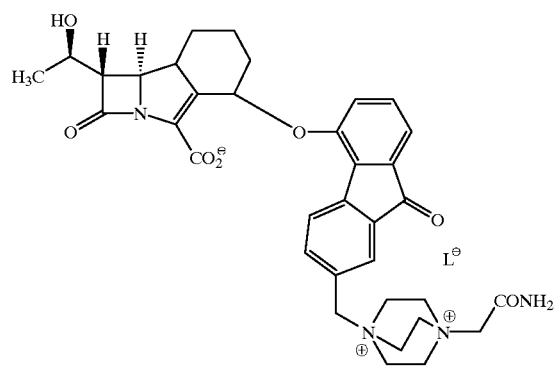
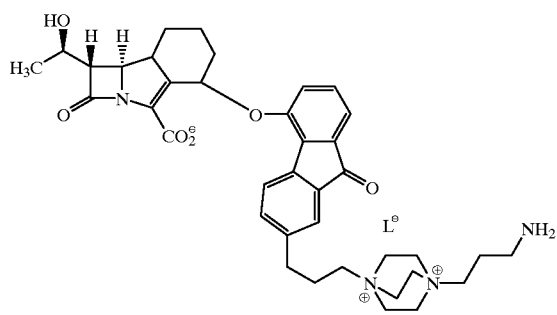
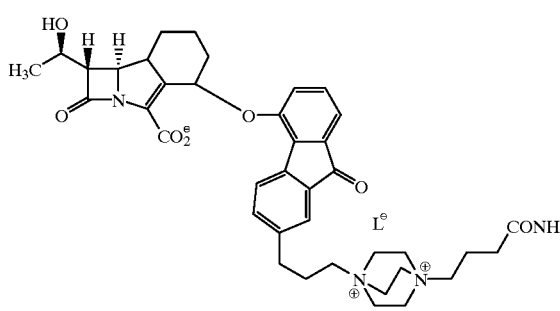
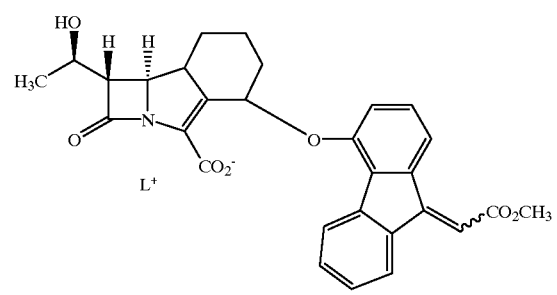
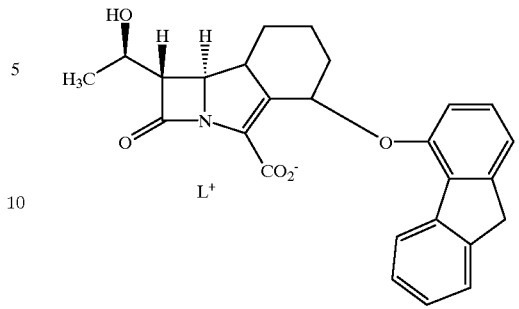
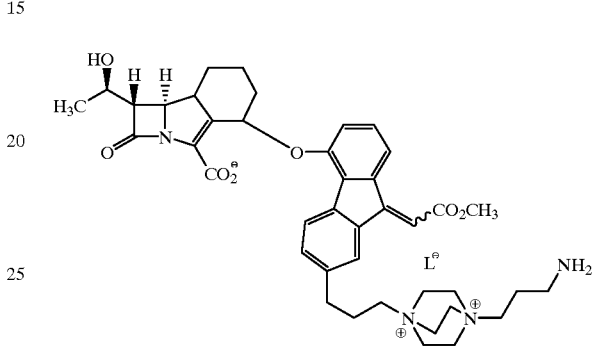
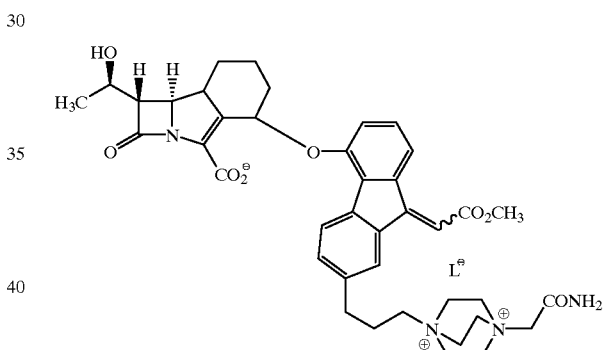
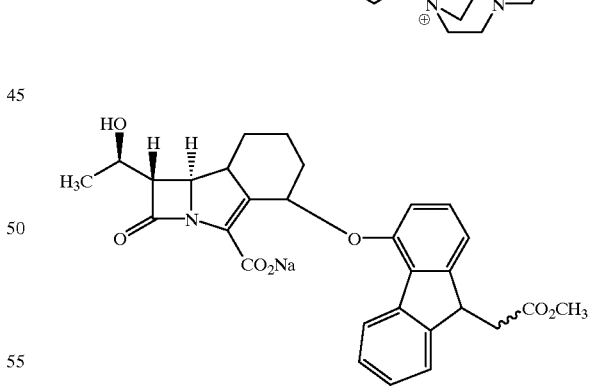
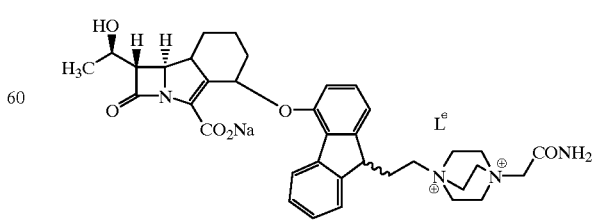

-continued
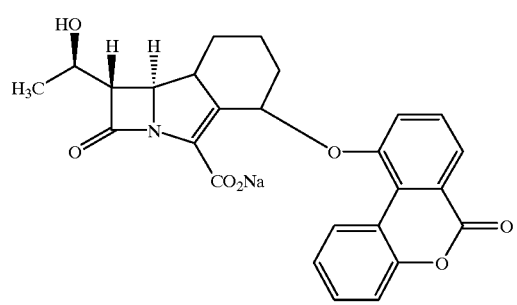
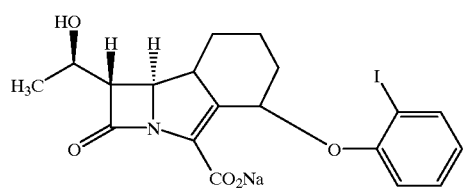
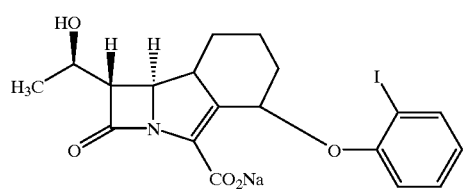
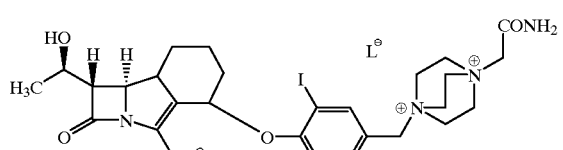
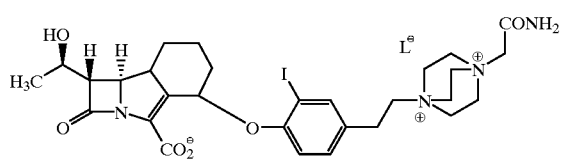
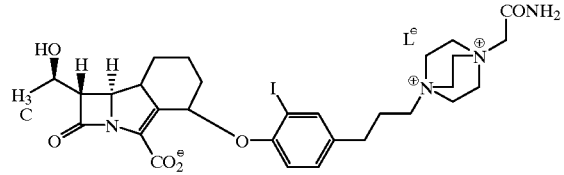
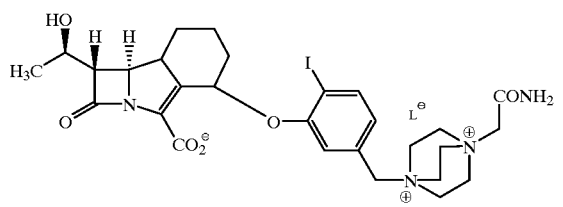
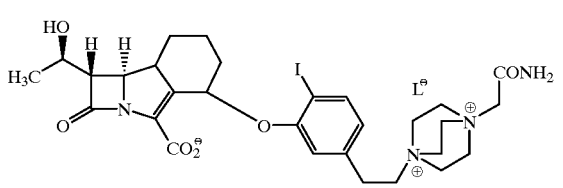
-continued
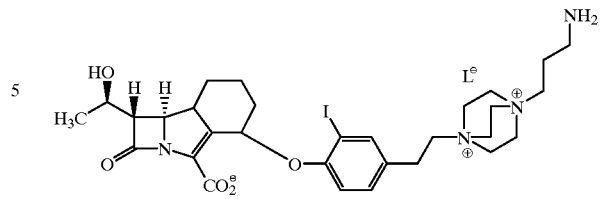
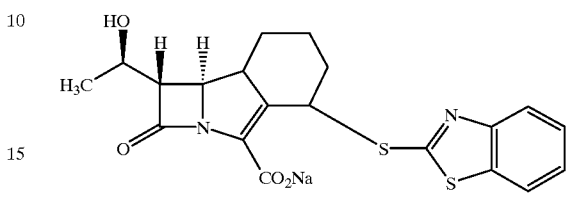
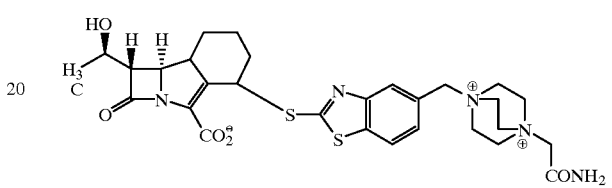
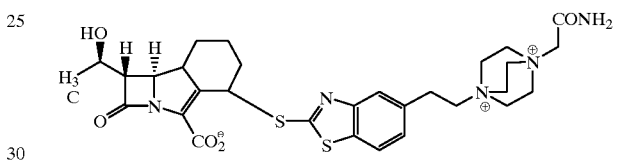
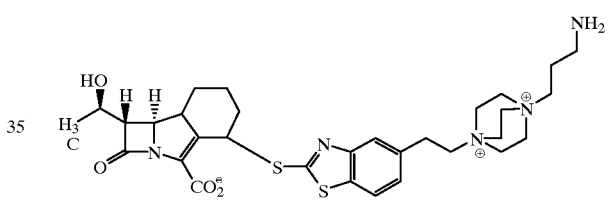
$L^+$ represents a positively charged counterion, e.g. $Na^+$, $K^+$, or an appropriate molar amount of a divalent cation, e.g., $Ca^{+2}$.
The compounds of the present invention are prepared by two basic processes which are illustrated by the following generic schemes:
General Synthesis Scheme I
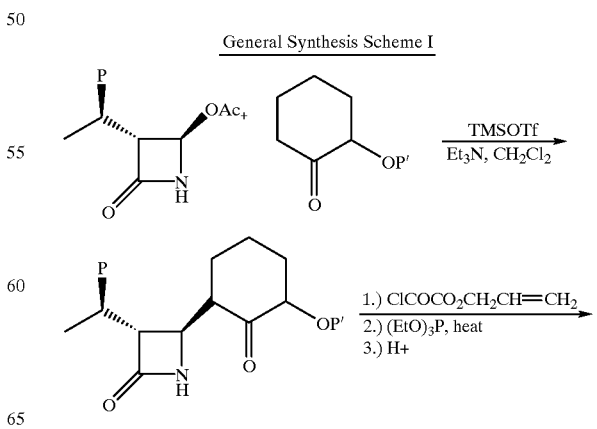

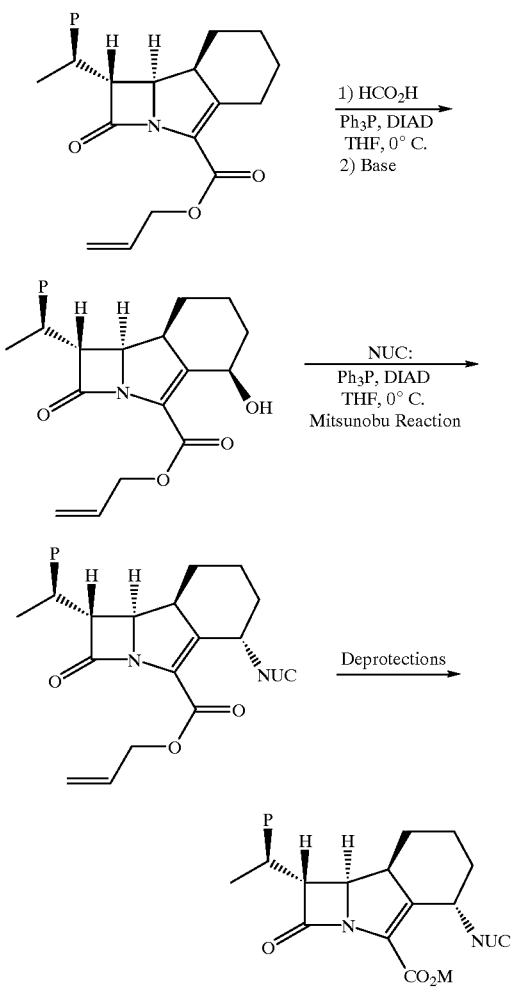

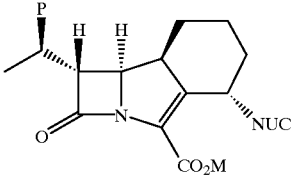

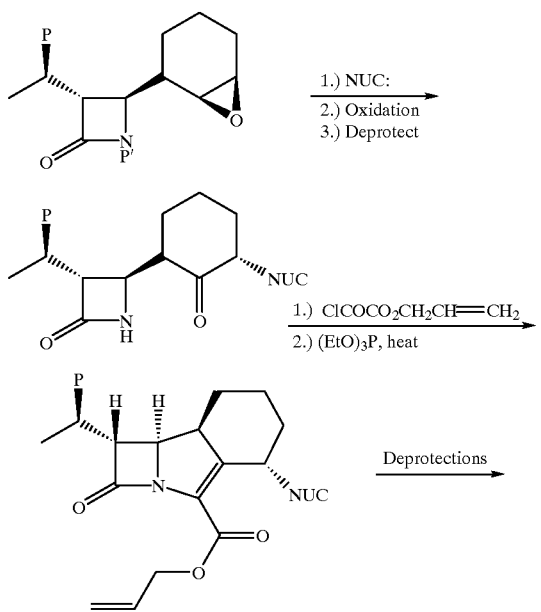

General Synthesis Scheme 2

In words relative to Scheme 1, the tricyclic synthon is prepared in a similar fashion to the description found in EPO 507,313, in which the acetoxyazetidinone, wherein P is F or a suitably protected hydroxyl radical, such a allyloxycarbonyl, t-butyldimethylsilyl (TBS), t-butyldiphenylsilyl (DPTBS) or the like, is reacted with a suitably protected 2-hydroxy-cyclohexanone derivative such a trimethysilyl (TMS) or t-butyldimethylsilyl, or the like, using the conditions of Barrett, etal. (A. G. M. Barrett, etal, *J. Org. Chem.*, 1984, 49, 1679.) to effect displacement to provide a mixture of azetidinones in which the desired beta-isomers can be separated. Conversion to the oxalamide intermediate is accomplished with chloroallyloxalate or the like, and triethylamine in methylene chloride solution at from −78° C. to 0° C., which in turn is converted to the trinem synthon by in situ formation of the trisubstituted phosphorane intermediate with excess triethylphosphite, or diethylmethylphosphonite, or the like in toluene, p-xylene, or mesitylene, or the like at temperature of from 120° C. to 160° C. and concomitant intramolecular cyclization on prolonged heating at the same temperature range. Desilylation of either TMS or TBS covering groups using tetrabutylammonium fluoride (TBAF) or ammonium bifluoride and acetic acid in tetrahydrofuran (THF) solvent at a temperature of from 0° C. to 50° C., provides the requisite alcohol. The configuration of the hydroxyl group is inverted prior to incorporation of the MRS active sidechain, using the Mitsunobu reaction partners with anhydrous formic acid, or the like, to produce the formate ester, or the like, of the opposite configuration as the starting alcohol. Hydrolysis of the formate ester or the like provides the alcohol of the opposite configuration ready for incorporation of the MRS pharmacophore to ultimately provide the trinems of the invention in their protected form. Through the intermediacy of the Mitsunobu reaction (for a review see: Hughes, D. L. *Organic Reactions*, Paquette, L. ed., Vol. 42, John Wiley & Sons, USA, 1992. ), nucleophilic (NUC:) side chains (naphthosultams, phenols, and mercaptobenzothiazoles) in combination with reagents that comprise the Mitsunobu reaction such as an azodicarboxylate like diethylazodicarboxylate (DEAD), diisopropyldiazodicarboxylate(DIAD), and tetramethyldiazodicarboxamide (TMAD), or the like, and a tri-substituted phosphine, such as triphenylphosphine, tri-n-butylphosphine, and the like, in a suitable solvent such as tetrahydrofuran (THF), ether, acetonitrile, dimethylformamide (DMF), benzene, dimethylsulfoxide (DMSO), and the like at a temperature between about −20° C. and 35° C. for about 5 to 90 minutes can be readily incorporated onto the trinem nucleus. The covering groups of the resulting new trinems are then removed in accordance with the previous definitions of P. Typically, when P is a silyl based protecting group for the hydroxyl radical, the deprotections are performed sequentially: first, desilylation with TBAF/HOAc or aqueous triflic acid in THF, or the like; and second, deallylation using the palladium (O) catalyzed method of Jeffrey and McCombie (JOC, 1982, 47, 587.) Alternatively, if the hydroxyl protecting is allylcarbonyl, then the deprotections are performed simultaneously by the latter method.

49

Alternatively, as depicted in Scheme 2, the cyclohexene-epoxy-azetidinone, as described in EP 416,953 and incorporated by reference herein, is reacted with the previously defined nucleophiles (NUC:) of the invention in the presence of a base in a manner as described in EP 416,953. The resulting alcohol is oxidized to the ketone via a Swern oxidation or the like, and after the removal of the azetidinone protecting group, if it was necessary, the resulting azetidinone is then processed in a fashion analogous to that outlined in Scheme 1, ie, oxalamide and ylid formation followed by cyclization provides the fully elaborated trinems ready for the deprotection sequences.

In most instances, the aforementioned nucleophilic partners in the Mitsunobu reaction possess functionalized substituents which allow for the introduction of the previously defined heterocycles, Q, and thereby necessitate additional chemical steps in the general synthesis plan. These steps are outlined in Scheme 3. Once the fully elaborated trinem has been synthesized, the substitutent tether from the particular side-chain class typically possesses a silyl covered hydroxyl radical which in the first step is then uncovered in the usual way as expressed above. Next the hydroxyl group is converted to a suitable leaving group such as a triflate, mesylate, tosylate, iodide, chloride, bromide, and the like, and then displacing the resulting leaving group with a compound Q, such as N-methyl-imidazole, N-(2-hydroxyethyl)-imidazole, N-methyl-diazabicyclooctane, 1-(carbamoylmethyl)-4-aza-1-azoniabicyclo-[2.2.2.]-octane, 1-(3-hydroxyprop-1-yl)-4-aza-1-azoniabicyclo-[2.2.2.]-octane, pyridine, morpholine and the like which contain a nitrogen atom that can act as a nucleophile. Alternatively, in some cases, the charged substituent may be incorporated in the side chain before addition to the trinem or may be introduced after the final deprotections. However, introduction of the charged substituent by modification of the hydroxyl group before deprotection is greatly preferred.

General Synthesis Scheme 3

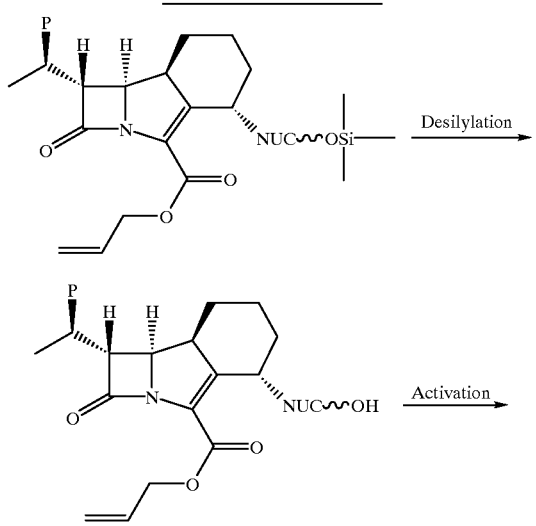

50

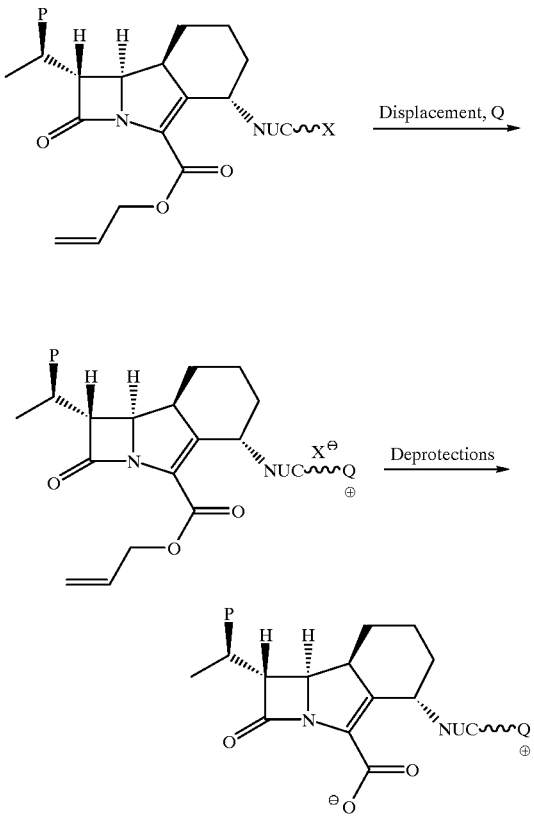

The conversion of the hydroxyl group to a suitable leaving group is accomplished by treating the hydroxyl substituted compound in a suitable solvent such as dichloromethane, tetrahydrofuran, ether, benzene, and the like with an activating reagent, such as trifluoromethanesulfonic anhydride, methanesulfonic anhydride, toluenesulfonic anhydride, methanesulfonyl chloride, benzenesulfonyl chloride, toluenesulfonyl chloride, and the like in the presence of a suitable base such as triethylamine, tributylamine, diisopropylethylamine, and the like at a temperature between about −100° C. and 0° C. for about 5 to 120 minutes. is treated with 1–3 molar equivalents of compound Q at a temperature between about −78° C. and 50° C. for about 15 to 120 minutes.

The intermediate thus obtained contains a leaving group, which may be converted to an alternative leaving group, iodide, by treating a solution of the intermediate in a suitable solvent such as acetone, methyl ethyl ketone, and the like at about −10° C. to 50° C. with an excess of sodium iodide or potassium iodide for about 0.25 to 24 hours.

In many cases, the iodide is obtained in sufficiently pure form that it may be used without further purification. For ease of handling, the iodide, if not crystalline, may be lyophilized from benzene to afford an amorphous, easily handled, solid.

The activated hydroxyl group or iodide is displaced by reacting with 1–3 molar equivalents of compound Q at a temperature between about −78° C. and 50° C. for about 15 to 120 minutes, in a solvent such as acetonitrile, dichloromethane, DMF, or DMSO, or the like.

In some cases, it is desirable to form the activated intermediate in one solvent, isolate the activated intermediate, and conduct the displacement reaction in a different solvent. In other cases, the displacement may be conducted without isolation of the intermediate and, in cases where Q is also used as a base, may even be concurrent with the formation of the activated intermediate.

In cases where the displacement reaction is best accomplished by using the iodide, a solution of the iodide is combined with an approximately equivalent amount (0.9–1.05 molar equivalents) of compound Q. A silver salt of a non-nucleophilic acid, such as silver trifluoromethanesulfonate, silver tetrafluoroborate and the like is then added. Although the reaction will proceed in the absence of the silver salt, the reaction proceeds more rapidly in the presence of the silver salt. In addition, the silver salt assists in the removal of the displaced iodide from the reaction mixture which can improve the efficiency of subsequent steps. The resulting mixture is then subjected to a standard work-up procedure familiar to those skilled in the art to afford a crude product which is purified, if necessary, by recrystallization or chromatography.

An alternative method for introducing a positive charge into the side chain may be applied to side chains (i.e. $R^{sc}$ groups) that contain a nitrogen atom which may be quaternized by reaction with a suitable alkylating reagent AR, such as methyl iodide, methyl bromide, benzyl trichloroacetimidate, methyl trifluoromethanesulfonate, triethyloxonium tetrafluoroborate, and the like. Quaternization of the nitrogen atom in the side chain is effected by treating a solution of the compound with a slight excess (1.05 to 1.2 molar equivalents) of the alkylating reagent.

The synthesis of the target compound is completed by removing any protecting groups which are present in the penultimate intermediate using standard techniques which are well known to those skilled in the art. The deprotected final product is then purified, as necessary, using standard techniques such as ion exchange chromatography, HPLC on reverse phase silica gel, MPLC on reverse phase polystyrene gel, and the like or by recrystallization.

The final product may be characterized structurally by standard techniques such as NMR, IR, MS, and UV. For ease of handling, the final product, if not crystalline, may be lyophilized from water to afford an amorphous, easily handled solid.

The naphthosultam, 2-mercapto-benzothiazole, and phenolic side chain groups used in the synthesis of the compounds of the present invention have, in some cases, been described in the chemical literature. In particular the 2-mercapto-benzothiazoles have been adequately described in U.S. Pat. No. 5,496,816, issued Mar. 5, 1996, which is incorporated herein by reference. In other cases, precursor compounds which may be readily converted to the requisite side chain types have been described in the literature. In cases where the requisite synthons are unknown in the literature it is necessary to synthesize them by a newly developed synthesis. One skilled in the art can adapt a previously published synthesis of an analogous synthon to prepare the requisite compound in a straightforward manner without undue experimentation. Numerous examples of these syntheses are described herein (see below).

The compounds of the present invention are valuable antibacterial agents active against various Gram-positive and to a lesser extent Gram-negative bacteria, and accordingly find utility in human and veterinary medicine.

Many of compounds of the present invention are biologically active against MRSA/MRCNS. In vitro antibacterial activity is predictive of in vivo activity when the compounds are administered to a mammal infected with a susceptible bacterial organism.

Using standard susceptibility tests, the compounds of the invention are determined to be active against MRSA.

The compounds of the invention can be formulated in pharmaceutical compositions by combining the compound with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral composions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal a compound of formula I in an amount effective to treat said infection.

The preferred methods of administration of the Formula I antibacterial compounds include oral and parenteral, e.g., i.v. infusion, i.v. bolus and i.m. injection.

For adults, about 5–50 mg of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

The compounds of Formula I are of the broad class known as carbapenems. Many carbapenems are susceptible to attack by a renal enzyme known as dehydropeptidase (DHP). This attack or degradation may reduce the efficacy of the carbapenem antibacterial agent. Many of the compounds of the present invention, on the other hand, are less subject to such attack, and therefore may not require the use of a DHP inhibitor. However, such use is optional and contemplated to be part of the present invention. Inhibitors of DHP and their use with carbapenems are disclosed in, e.g., [European Patent Application Nos. 79102616.4, filed Jul. 24, 1979 (U.S. Pat. No. 0 007 614); and 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

The invention is further described in connection with the following non-limiting examples.

PREPARATIVE EXAMPLE 1

Synthesis of 5-(Trimethylsilyloxymethyl)-1,8-Naphthosultam

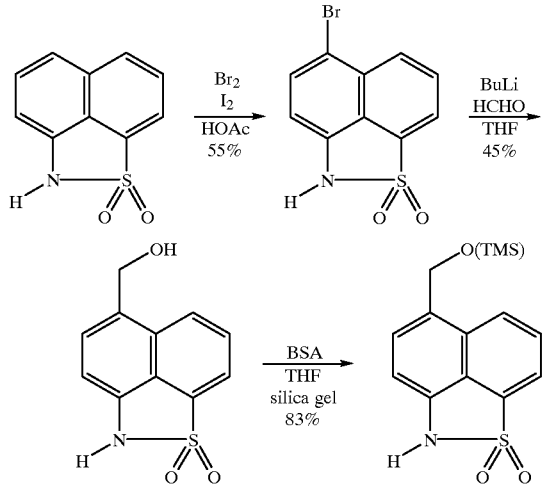

Step 1: 5-Bromo-1,8-naphthosultam

A suspension of 1,8-naphthosultam (5 g, 24.4 mmol) in acetic acid (20 mL) was treated with a dark solution of iodine (6.5 g, 25.6 mmol) and bromine (1.3 mL, 25.2 mmol) in acetic acid (20 mL) over 10 minutes. The suspension was stirred an additional 95 minutes then placed in a 60° C. oil bath for 30 minutes. After cooling to room temperature, the mixture was added to a 1% aqueous NaHSO$_3$ solution (300 mL). The dark precipitate was filtered and dried overnight under a stream of nitrogen. The resulting solid (6 g) was dissolved in ethyl acetate then silica gel (ca. 6 g) was added and the mixture was evaporated under vacuum. The silica-adsorbed mixture was loaded onto a 4.5×30 cm silica column (silica gel 60) and was eluted with 5% ethyl acetate/methylene chloride, collecting 25 mL fractions. Fractions 24–60 were combined and evaporated to give a green solid which was recrystallized from toluene to give the title compound as a light green solid (3.8 g).

$^1$H NMR (CDCl$_3$, 500 MHz) δ6.82 (d, ArH), 6.83 (br.s, NH), 7.80 (d, ArH),7.93 (t, ArH), 8.05 (d, ArH) and 8.38 (d, ArH).

Step 2: 5-(hydroxymethyl)-1,8-naphthosultam

A solution of 5-bromo-1,8-naphthosultam (0.5 g, 1.76 mmol) in anhydrous tetrahydrofuran (10 mL) under nitrogen was cooled in a dry ice/acetone bath in a three neck flask. N-butyllithium (2.75 mL of a 1.6 M solution in hexanes, 4.4 mmol) was added over 2 minutes and the suspension was stirred an additional 7 minutes. Paraformaldehyde (0.317 g, 10.6 mmol), placed in the bulb of a drying tube which was attached to the flask, was heated with a heat gun while a slow stream of nitrogen was blown over the solid. The generated formaldehyde was carried into the flask and the carrier gas vented through a line connected to a Firestone valve over a period of 13 minutes. After an additional 5 minutes, the mixture was removed from the bath and stirred for 10 minutes. Aqueous hydrochloric acid (3 mL of a 2 N solution) was added and the clear suspension was stirred an additional 10 minutes. The mixture was partitioned between ethyl acetate (50 mL) and water (50 mL). The ethyl acetate layer was washed with saturated aqueous sodium chloride (20 mL), dried over magnesium sulfate, filtered, and evaporated. The solid residue (0.5 g) was dissolved in 5% methanol/methylene chloride and was loaded onto a 24×4.5 cm silica gel column (silica gel 60, packed/loaded/eluted with 5% methanol/methylene chloride), collecting 8 mL fractions. Fractions 12–42 were combined and evaporated to give the title compound as a white solid (0.185 g).

$^1$H NMR (DMSO-d$_6$, 500 MHz) δ4.85 (d, CH$_2$OH), 5.22 (t, CH$_2$OH), 6.82 (d, ArH), 7.52 (d, ArH),7.83 (t, ArH), 8.13 (d, ArH) and 8.38 (d, ArH).

Step 3: 5-(trimethylsilyloxymethyl)-1,8-naphthosultam

A solution of 5-(hydroxymethyl)-1,8-naphthosultam (0.185 g, 0.79 mmol) in tetrahydrofuran (1 mL) was treated with N,O-Bis(trimethylsilyl)acetamide ((BSA), 0.49 mL, 1.98 mmol). The mixture was stirred at room temperature for 1 hour then evaporated. The residual oil was dissolved in methylene chloride (1 mL) and was filtered through silica gel 60 (2.5 g), eluting the silica with additional methylene chloride (50 mL). The solvent was evaporated under vacuum and the residue was lyophilized from benzene (3 mL) to give the title compound as a white solid (0.20 g).

$^1$H NMR (CDCl$_3$, 500 MHz) δ0.19 (s, SiMe$_3$), 5.07 (s, CH$_2$), 6.83 (d, ArH), 6.87 (br.s, NH), 7.50 (d, ArH), 7.78 (t, ArH), 7.95 (d, ArH) and 8.26 (d, ArH).

PREPARATIVE EXAMPLE 2

Synthesis of 5-(2-(Trimethylsilyloxy)-Ethyl)-1,8-Naphthosultam

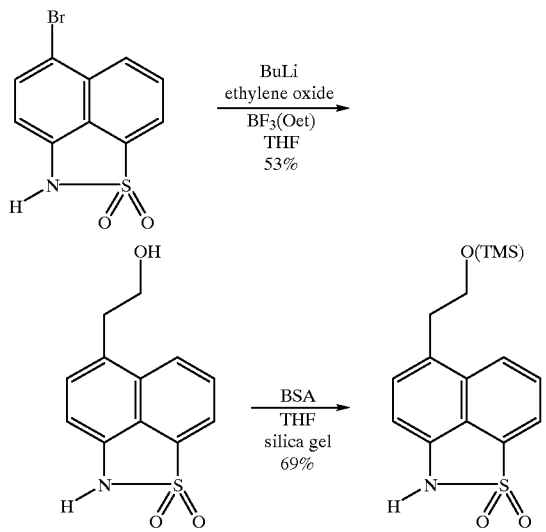

PREPARATIVE EXAMPLE 3

Synthesis of 4-(2-(Trimethylsilyloxy)-Ethyl)-1,8-Naphthosultam

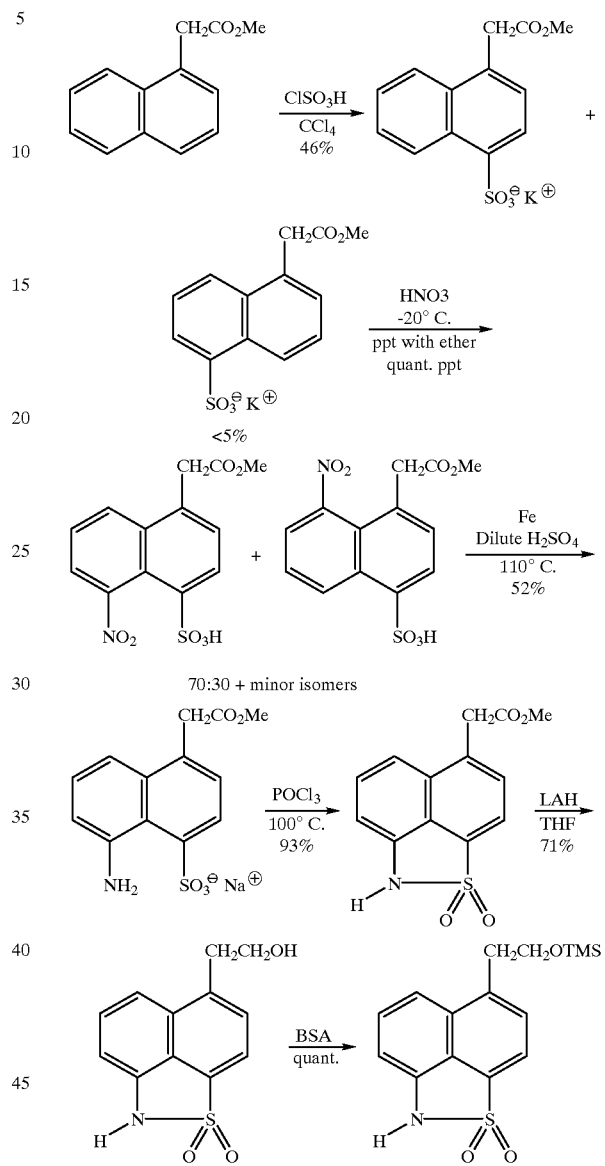

Step 1: 5-(2-(hydroxy)-ethyl)-1,8-naphthosultam

A solution of 5-bromo-1,8-naphthosultam (0.6 g, 2.11 mmol) in anhydrous tetrahydrofuran (10 mL) under nitrogen was cooled in a dry ice/acetone bath. N-butyllithium (3.3 mL of a 1.6 M solution in hexanes, 5.28 mmol) was added over 7 minutes and the suspension was stirred an additional 8 minutes. An excess of ethylene oxide was slowly bubbled into the mixture over 5 minutes. Boron trifluoride etherate (0.26 mL, 2.11 mmol) was then added over 5 minutes. After an additional 20 minutes, the reaction was quenched with the addition of acetic acid (0.35 mL, 6 mmol). The mixture was partitioned between ethyl acetate (100 mL) and water (100 mL). The ethyl acetate layer was washed with saturated aqueous sodium chloride (50 mL), dried over magnesium sulfate, filtered, and evaporated. The residual oil (0.7 g) was dissolved in 5% methanol/methylene chloride and was loaded onto a 24×2.75 cm silica gel column (silica gel 60, packed/loaded/eluted with 5% methanol/methylene chloride), collecting 8 mL fractions. Fractions 26–39 were combined and evaporated to give the title compound as an oil (0.28 g).

$^1$H NMR (DMSO-$d_6$, 500 MHz) δ3.22 (t, CH$_2$Ar), 3.87 (t, CH$_2$OH), 6.79 (d, ArH), 7.35 (d, ArH), 7.74 (t, ArH), 7.91 (d, ArH) and 8.21 (d, ArH).

Step 2: 5-(2-(trimethylsilyloxy)-ethyl)-1,8-naphthosultam

A solution of 5-(2-(hydroxy)-ethyl)-1,8-naphthosultam (0.09 g, 0.36 mmol) in tetrahydrofuran (1 mL) was treated with N,O-Bis(trimethylsilyl)acetamide (0.223 mL, 0.90 mmol). The mixture was stirred at room temperature for 20 minutes and was evaporated. The residual oil was dissolved in methylene chloride (3 mL) and was filtered through silica gel 60 (2.7 g), eluting the silica with additional methylene chloride (50 mL). The solvent was evaporated under vacuum and the residue was lyophilized from benzene (3 mL) to give the title compound as a white solid (0.08 g).

Step 1: potassium 1-(methoxycarbonylmethyl)-4-naphthalene sulfonate

A solution of methyl 1-naphthaleneacetate (1 mL, 5.77 mmol) in carbon tetrachloride (1 mL) was cooled under nitrogen in an ice bath. Chlorosulfonic acid (0.38 mL, 5.7 mmol) was added dropwise over 8 minutes. After an additional 30 minutes, the viscous mixture was removed from the bath and was stirred at room temperature for 17 hours to give a white solid. The solid was partitioned between methylene chloride (5 mL) and water (5 mL). After filtering through solka-floc, the methylene chloride layer was extracted with more water (2×5 mL), and the combined aqueous extracts were basified with potassium carbonate to give a precipitate. The suspension was concentrated to approximately 5 mL and was cooled in an ice bath. The suspension was then filtered and the collected solid was washed with cold water (2 mL). The solid was dried under a stream of nitrogen to give the title compound as a white solid (0.84 g).

¹H NMR (DMSO-d₆, 500 MHz) δ3.73 (s, OMe), 4.27 (s, CH₂Ar), 7.53 (d, ArH), 7.71 (t, ArH),7.76 (t, ArH), 8.06 (d, ArH), 8.10 (d, ArH) and 8.73 (d, ArH).

Step 2: 1-(methoxycarbonylmethyl)-5-nitro-4-naphthalene sulfonic acid

Potassium 1-(methoxycarbonylmethyl)-4-naphthalene sulfonate (10 g, 31.4 mmol) was added portionwise over 30 minutes to 90% nitric acid, which was cooled in a methanol/ice bath to approximately −15° C. After 2 hours, the bath temperature had reached −10° C. and diethyl ether (200 mL) was added to the mixture. The precipitated solid was filtered, washed with ether (100 mL) and isopropanol (20 mL), and dried under a stream of nitrogen to give the title compound as an approximately 70:30 mixture of the 5- and 8-nitro isomers (approximately 12 g).

¹H NMR (D₂O, 500 MHz) δ3.69 (s, OMe), 4.30 (s, CH₂Ar), 7.67 (t, ArH), 7.71 (d, ArH),8.18 (d, ArH), 8.29 (d, ArH) and 8.33 (d, ArH).

Step 3: sodium 1-(methoxycarbonylmethyl)-5-amino-4-naphthalene sulfonate 1-(methoxycarbonylmethyl)-5-nitro-4-naphthalene sulfonic acid (2 g, 6.15 mmol) was dissolved in water (20 mL), containing 0.5 mL concentrated sulfuric acid, and was added dropwise over 5 minutes to a refluxing suspension of iron (4 g, 71.6 mmol) in water (100 mL). After refluxing for one hour, the dark mixture was cooled to room temperature, made basic with sodium carbonate, and concentrated to approximately 30 mL. The residual mixture was placed on a CG-161 amberchrom resin column (2.5×30 cm). The column was washed with water (200 mL), 10% MeCN/H₂O (200 mL), and 25% MeCN/H₂O (400 mL), collecting 25 mL fractions. Fractions 21–28 were combined and evaporated to give the title compound as a dark solid (0.675 g).

¹H NMR (D₂O 500 MHz) δ3.64 (s, OMe), 4.18 (s, CH₂Ar), 7.04 (d, ArH), 7.38 (d, ArH),7.41 (d, ArH), 7.45 (t, ArH) and 8.22 (d, ArH).

Step 4: 4-(methoxycarbonylmethyl)-1,8-naphthosultam

Sodium 1-(methoxycarbonylmethyl)-5-amino-4-naphthalene sulfonate (0.675 g, 2.13 mmol) was suspended in phosphorous oxychloride (10 g, 65.2 mmol) and was refluxed for 1 hour to give a thin suspension. The mixture was cooled to room temperature and was partitioned between ethyl acetate (100 mL) and water (100 mL). The water layer was extracted with ethyl acetate (50 mL) and the combined ethyl acetate layers were washed with saturated aqueous sodium chloride (100 mL), dried over magnesium sulfate, filtered and evaporated to give the title compound as a solid (0.55 g).

¹H NMR (CDCl₃, 500 MHz) δ3.72 (s, OMe), 4.15 (s, CH₂Ar), 6.86 (br s, NH), 6.97 (d, ArH), 7.60 (t, ArH),7.67 (d, ArH), 7.71 (d, ArH) and 7.95 (d, ArH).

Step 5: 4-(2-(hydroxy)-ethyl)-1,8-naphthosultam

A solution of 4-(methoxycarbonylmethyl)-1,8-naphthosultam (0.2 g, 0.72 mmol) in tetrahydrofuran (2 mL) was cooled under nitrogen in an ice bath. Lithium aluminum hydride (1.44 mL of a 1.0 M solution in THF, 1.44 mmol) was added over 1 minute to give a light yellow suspension. After 30 minutes, water was carefully added and the mixture was partitioned between ethyl acetate (30 mL) and 1N hydrochloric acid (10 mL). The aqueous layer was extracted with ethyl acetate (50 mL) and the combined ethyl acetate layers were washed with saturated aqueous sodium chloride (10 mL), dried over magnesium sulfate, filtered and evaporated. The residual solid (0.16 g) was purified by preparative thin layer chromatography (2×1000 micron silica gel plates, developed/eluted with 5% MeOH/CH₂Cl₂) to give the title compound as a solid (0.127 g).

¹H NMR (0.14 mL CDCl₃ and 0.01 mL CD₃OD, 500 MHz) δ3.33 (t, CH₂Ar), 3.91 (t, CH₂OH), 6.84 (d, ArH), 7.49 (dd, ArH),7.59 (d, ArH), 7.59 (d, ArH) and 7.83 (d, ArH).

Step 6: 4-(2-(trimethylsilyloxy)-ethyl)-1,8-naphthosultam

N,O-Bistrimethylsilylacetamide (0.31 mL, 1.25 mmol) was added to a solution of 4-(2-(hydroxy)-ethyl)-1,8-naphthosultam (0.125 g, 0.50 mmol) in tetrahydrofuran (1 mL). After one hour the mixture 5 was evaporated and the residue was dissolved in methylene chloride (2 mL) and filtered through silica gel (2.5 g). The silica gel was eluted with methylene chloride (50 mL), the solvent was evaporated and the residue was lyophilized from benzene (3 mL) to give the title compound as an oil (0.16 g, quant.).

¹H NMR (CDCl₃, 500 MHz) δ0.035 (s, TMS), 3.37 (t, CH₂Ar), 3.94 (t, CH₂O(TMS)), 6.95 (d, ArH), 7.56 (dd, ArH), 7.64 (d, ArH), 7.71 (d, ArH) and 7.92 (d, ArH).

PREPARATIVE EXAMPLE 4

Synthesis of 4-(Trimethylsilyloxy)-1,8-Naphthosultam

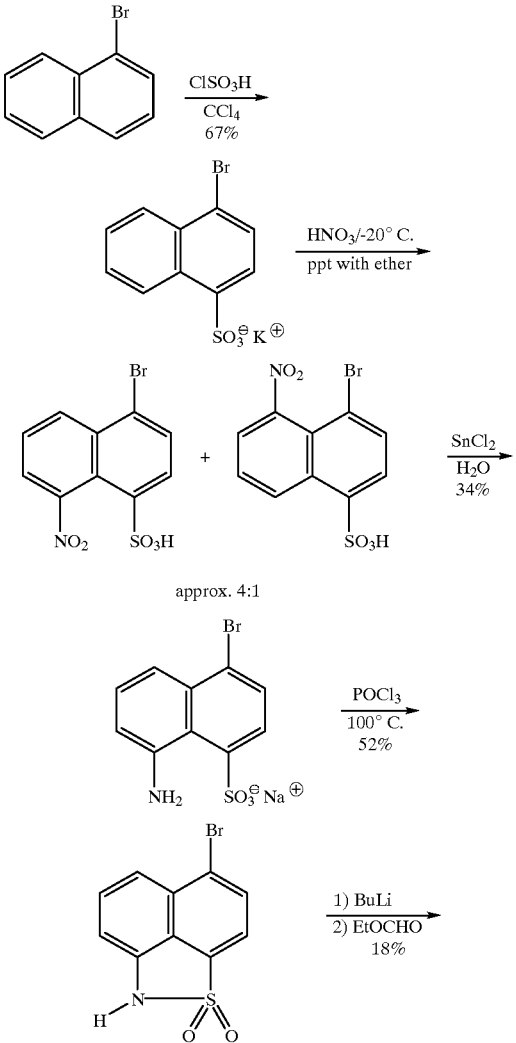

-continued

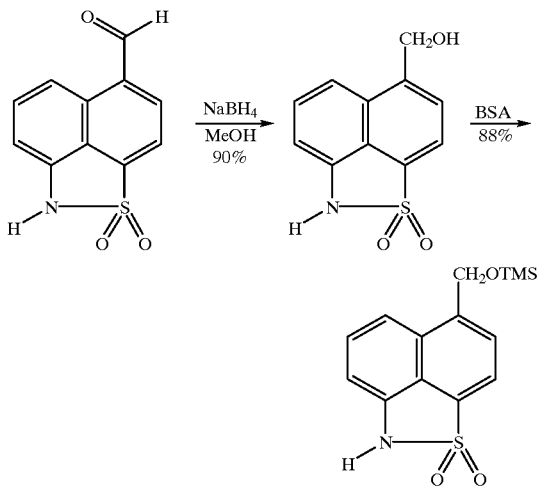

Step 1: potassium 1-bromo-4-naphthalenesulfonate

A solution of 1-bromonaphthalene (19 mL, 137 mmol) in carbon tetrachloride (24 mL) was cooled in an ice bath under nitrogen. Chlorosulfonic acid (9.1 mL, 137 mmol) was added dropwise over 20 minutes. After an additional 5 minutes, the heavy grey suspension was removed from the ice bath and was stirred at room temperature for 16 hours to give a grey paste. The mixture was partitioned between methylene chloride (100 mL) and water (300 mL). The aqueous layer was made basic with potassium carbonate and the resulting suspension was filtered. The collected solid was washed with methylene chloride (50 mL) and water (50 mL), and dried under vacuum to give the title compound as a white solid (30 g, 67%).

$^1$H NMR (DMSO-d$_6$, 500 MHz) δ7.61 (m, ArH), 7.65 (m, ArH), 7.82 (m, 2ArH), 8.14 (dd, ArH), and 8.90 (dd, ArH).

Step 2: 1-bromo-5-nitro-4-naphthalene sulfonic acid

Potassium 1-bromo-4-naphthalenesulfonate (1.38 g, 4.24 mmol) was added portionwise over 20 minutes to 90% nitric acid (2 mL), which was cooled in a methanol/ice bath to approximately −15° C. After 1.5 hours, the mixture was placed in a refrigerator for 20 hours. Diethyl ether (20 mL) was added and the precipitated solid was filtered, washed with ether (100 mL) and isopropanol (20 mL), and dried under a stream of nitrogen to give the title compound as an approximately 4:1 mixture of the 5- and 8-nitro isomers (1.25 g).

$^1$H NMR (D$_2$O, 500 MHz) δ7.70 (dd, ArH), 8.09 (d, ArH), 8.20 (d, ArH), 8.21 (dd, ArH), and 8.63 (d, ArH).

Step 3: sodium 1-bromo-5-amino-4-naphthalenesulfonate

1-Bromo-5-nitro-4-naphthalenesulfonate (1 g, 3.01 mmol) and tin chloride dihydrate (1.83 g, 8.1 mmol) were suspended in a mixture of water (10 mL) and ethanol (10 mL). The resulting mixture was heated for 3 hours in a 100° C. oil bath. The mixture was cooled to room temperature and filtered. The collected solid was suspended in water (20 mL) and the mixture was made basic with sodium carbonate then placed on a CG-161 amberchrom resin column (3×9 cm). The column was washed with water (300 mL) and was eluted with 25% MeCN/H$_2$O, collecting 12 mL fractions. Fractions 17–19 were combined and evaporated to give the title compound as a solid (0.33 g).

$^1$H NMR (D$_2$O, 500 MHz) δ7.07 (dd, ArH), 7.49 (t, ArH), 7.83 (d, ArH), 7.85 (dd ArH) and 8.08 (d, ArH).

Step 4: 4-bromo-1 8-naphthosultam

Sodium 1-bromo-5-amino-4-naphthalenesulfonate (1.2 g, 3.70 mmol) was suspended in phosphorous oxychloride (10 mL, 107 mmol) and the mixture was refluxed for 1 hour to give a thin suspension. The mixture was cooled to room temperature and was added to ice (100 nL). The precipitate was collected and washed with water (20 mL) then dried under vacuum (0.675 g). A second drop was obtained from the filtrate (0.186 g). The combined solids were dissolved in 5% methanol in methylene chloride and were placed on a silica gel column (29×3.5cm, packed and eluted with 5% methanol in methylene chloride), collecting 8 mL fractions. Fractions 27–39 were combined and evaporated to give the title compound as a solid (0.55 g).

$^1$H NMR (0.14 mL CDCl$_3$ and 0.01 mL CD$_3$OD, 500 MHz) δ6.89 (d, ArH), 7.58(dd ArH), 7.68 (d, ArH), 7.73 (d, ArH) and 7.95 (d, ArH).

Step 5: 4-formyl-18-naphthosultam

A solution of 4-bromo-1,8-naphthosultam (0.24 g, 0.845 mmol) in anhydrous tetrahydrofuran (5 mL) was cooled in a dry ice/acetone bath under nitrogen. n-Butyllithium (1.32 mL of a 1.6 M solution in hexanes, 2.11 mmol) was added and the mixture was stirred for 5 minutes. Ethyl formate (1 mL, 12.4 mmol) was then added, and after an additional 5 minutes, 2N aqueous hydrochloric acid (3 mL) was added. The flask was removed from the bath and the yellow solution was partitioned between ethyl acetate (30 mL) and water (30 mL). The ethyl acetate layer was washed with saturated aqueous sodium chloride (20 mL), dried over magnesium sulfate, filtered, and evaporated. The residual oil was purified on preparative silica gel plates (3×1000 micron/ developed and eluted with 5% methanol/methylene chloride) to give the title compound as a red solid (0.035 g).

$^1$H NMR (CDCl$_3$, 500 MHz) δ7.09 (d, ArH), 7.78 (dd, ArH), 8.12 (d, ArH), 8.30(d, ArH), 8.70 (d, ArH) and 10.5 (s, CHO).

Step 6: 4-(hydroxymethyl)-1,8-naphthosultam

A solution of 4-formyl-1,8-naphthosultam (0.035 g, 0.15 mmol) in anhydrous methanol (1 mL) was cooled in an ice bath under nitrogen. Sodium borohydride (0.011 g, 0.3 mmol) was added and the solution was stirred for 30 minutes. The mixture was partitioned between methylene chloride (10 mL) and 0.2N aqueous hydrochloric acid (10 mL). The aqueous layer was extracted with 5% methanol in methylene chloride (2×10 mL), and the combined organic layers were evaporated to give the title compound as a yellow solid (0.032 g).

$^1$H NMR (0.14 mL CDCl$_3$ and 0.01 mL CD$_3$OD, 500 MHz) δ5.13 (s, CH$_2$OH), 6.85 (d, ArH), 7.50 (dd, ArH), 7.57 (d, ArH), 7.82 (d, ArH) and 7.88 (d, ArH).

Step 7: 4-(trimethylsilyloxymethyl)-1,8-naphthosultam

A solution of 4-(hydroxymethyl)- 1,8-naphthosultam (0.032 g, 0.136 mmol) in tetrahydrofuran (0.5 mL) was treated with N,O-Bis(trimethylsilyl)acetamide (0.084 mL, 0.34 mmol). The mixture was stirred at room temperature for 45 minutes and was evaporated. The residual oil was dissolved in methylene chloride (1 mL) and was filtered through silica gel 60 (1 g), eluting the silica with additional methylene chloride (50 mL). The solvent was evaporated under vacuum and the residue was lyophilized from benzene (3 mL) to give the title compound as a white solid (0.037 g).

$^1$H NMR (CDCl$_3$, 500 MHz) δ0.23 (s, SiMe$_3$), 6.78 (brs, NH), 5.23 (s, CH$_2$), 6.97 (d, ArH), 7.58 (dd, ArH), 7.64 (d, ArH), 7.90 (d, ArH) and 7.97 (d, ArH).

PREPARATIVE EXAMPLE 5

Synthesis of 4-(3-Trimethylsilyloxyprop-1-YL)-1,8-Naphthosultam

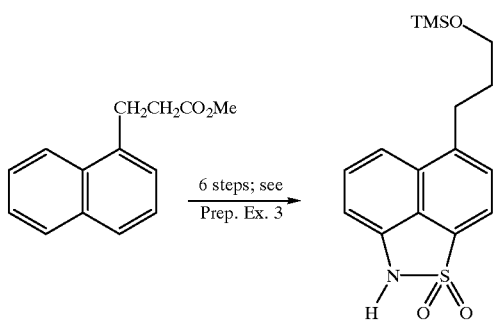

Steps 1–6 Synthesis of 4-(3-trimethylsilyloxyprop-1-yl)-1,8-naphthosultam

By substitution of methyl 1-naphthalenepropionate for methyl 1-naphthaleneacetate in the procedure of Preparative Example 3,4-(3-trimethylsilyloxyprop-1-yl)-1,8-naphthosultam is prepared.

PREPARATIVE EXAMPLE 6

Synthesis of 1-Hydroxydibenzothiophene

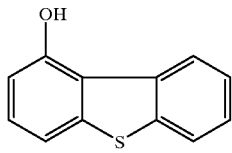

Step A

A stirred mixture of 3-methoxy benzenethiol (0.5 g, 3.6 mmoles), 1-fluoro-2-nitrobenzene (0.5 g, 3.6 mmoles), 37% KF/$Al_2O_3$ (1.4755 g, 3 w/w), and 18-crown-6 (0.1255 g, 0.36 mmoles) in sieve-dried acetonitrile (5 mL) was refluxed at 90° C. under a $N_2$ atmosphere for 1 hr. The reaction was allowed to cool to ambient temperature. The insoluble solids present in the reaction were filtered off and washed with EtOAc. The filtrate was collected and concentrated in vacuo to give a black/red solid (1.1487 g). The product was purified by plate layer chromatography with a mixture of 2:1 hexane/$CH_2Cl_2$ to afford the desired product as a yellow solid (0.7095 g).

$^1$H NMR ($CDCl_3$) δ: 3.82 (s, 3H), 6.90 (dd, 1H), 7.01 (dd, 1H), 7.12–7.23 (m, 3H), 7.3314 7.39 (m, 2H), 8.22 (dd, 1H).

Step B

To a stirred solution of the product obtained from Step A (0.7095 g, 2.7 mmoles) in absolute EtOH (7 mL) was added $SnCl_2.H_2O$ (1.8563 g, 8.1 mmoles). The resulting mixture was refluxed at 90° C. for 1.5 hrs under an atmosphere of $N_2$. The reaction was cooled to ambient temperature, poured into a mixture of ice, brine, and 5 N NaOH, and extracted with EtOAc (2X). The organic layers were combined, washed with brine, and dried over $Na_2SO_4$. Concentration in vacuo afforded the desired product as a yellow oil (0.6826 g). The product was purified by plate layer chromatography with 1:1 $CH_2Cl_2$/hexane to give the desired amine.

$^1$H NMR ($CDCl_3$) δ: 3.72 (s, 3H), 4.29 (br s, 2 H), 6.62–6.69 (m, 3H), 6.73–6.80 (m, 2H), 7.11 (t, 1H), 7.21 (t, 1H), 7.44 (dd, 1H).

Step C

To a thick slurry of the amine (0.277 g, 1.74 mmoles) from Step B in 2 N HCl (1.76 mL) and HOAc (0.54 mL) was added absolute EtOH (1.76 mL) to solubilize the mixture. The stirred mixture was cooled to 0° C. and a solution of $NaNO_2$ (0.1552 g, 2.09 mmoles) in water (0.2 mL) was added under $N_2$. The resulting light brown solution was stirred at 0° C. for 20 min. before adding a 93.1 mg/mL aqueous solution of $KPF_6$ (2.7 mL). Upon addition, yellow solid immediately precipitated out of solution. The yellow/brown solid was collected by vacuum filtration and washed with cold water (2X) and cold $Et_2O$ (3X). After drying in vacuo over 18 hrs, the diazonium salt was collected as a yellow solid (0.3149 g).

$^1$H NMR ($d_6$-acetone) δ: 3.83 (s, 3H), 7.16 (dd, 1H), 7.27 (s, 1H), 7.27–7.30 (dd, 1H), 7.47 (t, 1H), 7.79 (d, 1H), 7.88 (t, 1H), 8.18 (t, 1H), 8.84 (dd, 1H).

Step D

A solution of $FeSO_4.7H_2O$ (0.2258 g, 0.81 mmoles) in distilled water (3 mL) was heated to 100° C. The diazonium salt from Step C was added in one portion and the resulting mixture was stirred at 100° C. under $N_2$. Gas evolution was observed for the first 5–10 min. of the reaction. With time, the product oiled out of solution. After 30 min., the reaction was partitioned between EtOAc and ice/brine. The organic layer was collected, dried over $Na_2SO_4$, and concentrated in vacuo to give a green/brown oil (0.3317 g). The crude material was purified by plate layer chromatography with 20% $CH_2Cl_2$/hexane to afford the desired product as a white solid (0.040 g).

$^1$H NMR ($CDCl_3$) δ: 4.07 (s, 3H), 6.89 (d, 1H), 7.36–7.45 (m, 4H), 7.80 (dd, 1H), 8.64 (dd, 1H).

Step E

To a stirred solution of the dibenzothiophene (0.040 g, 0.19 mmoles) isolated from Step D in HOAc (2.5 mL) was added 40% HBr (0.65 mL, 5.6 mmoles) under $N_2$. The reaction was heated to 130° C. for 20 hrs. The resulting green solution was partitioned between EtOAc and ice/brine. The organic layer was washed with sat. $NaHCO_3$ (2X) and brine. The EtOAc extract was dried over $Na_2SO_4$ and concentrated in vacuo to give an off-white solid (0.0366 g). Purification by plate layer chromatography with 1:1 hexane/$CH_2Cl_2$ afforded the desired phenol as a white solid (0.0294 g).

$^1$H NMR ($CDCl_3$) δ: 5.53 (s, 1H), 6.77 (d, 1H), 7.26 (t, 1H), 7.43–7.49 (m, 3H), 7.82 (dd, 1H), 8.63 (dd, 1H).

PREPARATIVE EXAMPLE 7

Preparation of 1-Hydroxy-5- T-Butyldimethylsilyloxymethyl Dibenzothiophene

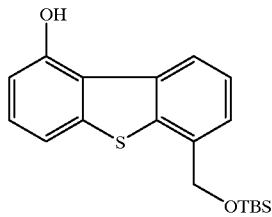

Step A

2-Bromo-3-nitrotoluene and 3-methoxy benzenethiol were coupled using the procedures described in Example 6 (Step A) to afford the desired product as a yellow oil.

$^1$H NMR ($CDCl_3$) δ: 2.38 (s, 3H), 3.73 (s, 3H), 6.62–6.66 (m, 2H), 6.68 (dd, 1H), 7.11 (t, 1H), 7.39 (m, 2H), 7.53 (dd, 1H).

Step B

The coupled product from Step A was reduced to its corresponding amine using the procedures described in Example 6 (Step B). The amine was obtained as a green/yellow oil.

$^1$H NMR (CDCl$_3$) γ: 2.39 (s, 3H), 3.71 (s, 3H), 6.58–6.65 (m, 3H), 6.71–6.76 (m, 2H), 7.09 (q, 2H).

Step C

Utilizing the procedure described in Example 6 (Step C), the amine from Step B was converted to its diazonium salt. The product was isolated as a green/yellow solid.

$^1$H NMR (d$_6$-acetone) δ: 2.49 (s, 3H), 3.78 (s, 3H), 6.97–7.02 (m, 3H), 7.35 (t, 1H), 8.04 (t, 1H), 8.31 (d, 1H), 8.87 (d, 1H).

Step D

To a solution of the diazonium salt (0.9275 g, 2.3 mmoles) obtained from Step C in anhydrous DMSO (20 mL) was added 3A molecular sieves. The mixture was heated to 60° C. and stirred for 1 hr. The orange mixture was filtered and the molecular sieves washed well with EtOAc. The filtrate was collected and washed with H$_2$O (4X) followed by brine. The organic layer was dried over Na$_2$SO$_4$ and concentrated in vacuo to give a dark red/orange oil. The crude material was purified by plate layer chromatography with 2:1 hexane/CH$_2$Cl$_2$ to give the desired dibenzothiophene as a white solid (0.1047 g).

$^1$H NMR (CDCl$_3$) δ:2.58 (s, 3H), 4.08 (s, 3H), 6.91 (d, 1H), 7.25 (d, 1H), 7.36 (t, 2H), 7.47 (d, 1H), 8.50 (d, 1H).

Step E

Utilizing the procedure described in Example 6 (Step E), the product from Step D was demethylated to give the phenol as a white solid.

$^1$H NMR (CDCl$_3$) δ:2.58 (s, 3H), 6.77 (d, IH), 7.24–7.31 (2d, 2H), 7.38 (t, 1H), 7.43 (t, 1H), 8.48 (d, 1H).

Step F

To a solution of the phenol (0.076 g, 0.35 mmoles) from Step E in CH$_2$Cl$_2$ (1 mL) was added NEt$_3$ (0.059 mL, 0.42 mmoles) at 0° C. under N$_2$. The reaction was stirred for 10 min. before adding acetyl chloride (0.027 mL, 0.39 mmoles). The reaction was then stirred at 0° C. for another 15 min. and poured into ice/H$_2$O. The mixture was extracted with EtOAc. The organic layers were washed with 1 N HCl followed by brine, and dried over Na$_2$SO$_4$. Concentration in vacuo gave the desired product as a light brown oil (0.1163 g).

$^1$H NMR (CDCl$_3$) δ: 2.53 (s, 3H), 2.57 (s, 3H), 7.19 (d, 1H), 7.27 (d, 1H), 7.38 (t, 1H), 7.43 (t, 1H), 7.73 (d, 1H), 8.08 (d, 1H).

Step G

The acetylated product (0.0902, 0.35 mmoles) obtained from Step F was dissolved in CCl$_4$ (0.5 mL) and placed under a N$_2$ atmosphere. NBS (0.0817 g, 0.46 mmoles) was added followed by a crystal of AIBN. The reaction was heated to 80° C. for 23 hrs. The reaction was poured into ice/brine and extracted with EtOAc. The organic layers were washed with 5% Na$_2$S$_2$O$_3$ and brine. Concentration in vacuo gave the crude product as a yellow oil (0.2085 g). The oil was purified by plate layer chromatography with 1:1 hexane/CH$_2$Cl$_2$ to afford the alkyl bromide as a yellow solid (0.0895 g).

$^1$H NMR (CDCl$_3$) δ: 2.53 (s, 3H), 4.77 (s, 2H), 7.23 (d, 1H), 7.46–7.52 (m, 3H), 7.76 (d, 1H), 8.22 (dd, 1H).

Step H

The alkyl bromide (0.0895 g, 0.27 mmoles) from Step G was combined with KOAc (0.0541 g, 0.53 mmoles) in sieve-dried DMF (1 mL) and heated to 100° C. for 1 hr. The reaction was poured into ice/H$_2$O and extracted with EtOAc. The organic layers were washed with additional H$_2$O (2X) and brine, and dried over Na$_2$SO$_4$. Concentration in vacuo gave an orange/red oil (0.114 g). The oil was purified by plate layer chromatography with 3:1 CH$_2$Cl$_2$/hexane to give a pale yellow solid (0.0635 g).

$^1$H NMR (CDCk$_3$) δ: 2.17 (s, 3H), 2.55 (s, 3H), 5.38 (s, 2H), 7.21 (d, 1H), 7.44–7.49 (m, 3H), 7.73 (d, IH), 8.22 (dd, 1H).

Step I

A yellow mixture of the product (0.0635 g, 0.2 mmoles) from Step H, 5 N NaOH (0.1 mL, 0.42 mmoles), and absolute EtOH (1 mL) was heated to 70° C. under N$_2$ for 15 min. The reaction was partitioned between EtOAc and ice/1 N HCl. The organic layer was washed with brine, dried over Na$_2$SO$_4$, and concentrated in vacuo to give an orange solid (0.0637 g). The solid was purified by plate layer chromatography with 5% EtOAc/CH$_2$Cl$_2$ to give the desired product as a slightly orange solid (0.0335 g).

$^1$H NMR (CDCl$_3$+CD$_3$OD) δ: 4.76 (s, 2H), 6.71 (d, 1H), 7.07 (t, 1H), 7.17 (d, 1H), 7.24–7.28 (m, 2H), 8.45 (d, 1H).

Step J

To a flask charged with the phenol (0.0335 g, 0.16 mmoles) from Step I was added a solution of TBSCI (0.0305 g, 0.17 mmoles) in DMF (0.5 mL) under N$_2$. The reaction was cooled to 0° C. and stirred for 10 min. before adding dropwise a solution of imidazole (0.0137 g, 0.19 mmoles) in DMF (0.25 mL). The solution was stirred at 0° C. for 1 h. The reaction was partitioned between EtOAc and ice/1 N HCl. The organic layer was washed with brine, dried over Na$_2$SO$_4$, and concentrated in vacuo to give a light brown oil. The oil was purified by plate layer chromatography with 3:1 CH$_2$Cl$_2$/hexane to afford the TBS-protected alcohol as a light yellow solid (0.0416 g).

$^1$H NMR (CDCl$_3$) δ: 0.15 (s, 3H), 0.98 (s, 6H), 4.97 (s, 2H), 6.76 (d, 1H), 7.26 (t, 1H), 7.45–7.48 (m, 3H), 8.55 (dd, 1H).

PREPARATIVE EXAMPLE 8

Preparation of 1-Hydroxy-5- T-Butyldimethylsilyloxypropyl Dibenzothiophene

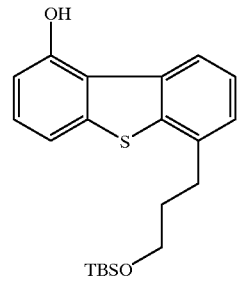

Step A

The acetylated dibenzothiophene (0.3985, 1.55 mmoles) obtained from Example 7 (Step F) was dissolved in CCl$_4$ (5 mL) and place under a N$_2$ atmosphere. Recrystallized NBS (0.3051 g, 1.7 mmoles) was added followed by a crystal of AIBN. The reaction was heated to 80° C. for 23 hrs. Additional NBS (0.3067 g, 1.7 mmoles) was added to the reaction and the mixture was stirred at 80° C. for another 6.5 hrs. The reaction was poured into ice/brine and extracted with EtOAc. The organic layers were washed with 5% Na$_2$S$_2$O$_3$ and brine. Concentration in vacuo gave an orange solid (0.5974 g). By $^1$H NMR analysis, the crude product contained a 3:1 mixture of the desired dibrominated product to the monobrominated product or the dibrominated product.

¹H NMR (CDCl₃) δ: 2.55 (s, 3H), 6.96 (s, 1H), 7.25 (d, 1H), 7.48–7.50 (m, 2H), 7.76 (t, 2H), 8.24 (d, 1H).

Step B

The crude alkyl bromide (0.4670 g, 1.1 mmoles) from Step A was dissolved in sieve-dried DMF (5 mL) and placed under $N_2$. KOAc (0.3396 g, 3.4 mmoles) was added in one portion and the reaction was heated to 100° C. After 1.5 hrs, The reaction was partitioned between EtOAc and $H_2O$. The organic layer was washed with water (3X) and brine, dried over $Na_2SO_4$, and concentrated in vacuo to give a brown/yellow oil (0.6382 g). The oil was purified by plate layer chromatography with 4 elutions using 3:2 $CH_2Cl_2$/hexane to give 2 major fractions: 1) the triacetate compound (0.1403 g) and 2) a mixture of the diacetate compound and the aldehyde (0.2077 g).

¹H NMR (CDCl₃) δ: 2.18 (s, 6H), 2.55 (s, 3H), 7.23 (d, 1H), 7.47 (t, 2H), 7.61 (d, 1H), 7.75 (d, 1H), 7.93 (s, 1H), 8.31 (dd, 1H).

Step C

The fraction from Step B containing the triacetate compound (0.1255 g, 0.4 mmoles) was suspended in absolute EtOH (2 mL) and 5 N NaOH (0.15 mL, 0.8 mmoles) was added under $N_2$. The reaction was heated to 70° C. for 20 min. then poured into ice/1 M HCl. The mixture was extracted with EtOAc. The organic layer was collected, washed with brine, dried over $Na_2SO_4$, and cocentrated in vacuo to give an orange solid (0.1065 g). The solid was purified by plate layer chromatography with 5% EtOAc/$CH_2Cl_2$ to afford the clean aldehyde as a yellow solid (0.0756 g).

¹H NMR (CDCl₃+d₆-acetone) δ: 6.73 (d, 1H), 7.07 (t, 1H), 7.21 (d, 1H), 7.40 (t, 1H), 7.73 (d, 1H), 8.78 (dd, 1H), 9.00 (bs, I H), 10.04 (s, 1H).

Step D

The fraction from Step B containing a mixture of the diacetate compound and the aldehyde (0.2077 g, 0.77 moles) was submitted under the same reaction conditions described in Step C. The resulting mixture of aldehyde and diol was separated by plate layer chromatography with 5% EtOAc/$CH_2Cl_2$ to give 0.0895 g of clean aldehyde.

Step E

The aldehydes from Step C and Step D were combined and acetylated using the procedures described in Example 7 (Step F). The reaction was stirred at 0° C. for a total of 30 min. The desired product was isolated as tan solid.

¹H NMR (CDCl₃) δ: 2.57 (s, 3 H), 7.29 (d, IH), 7.50 (t, 1H), 7.65 (t 1H), 7.82 (d, 1H), 7.99 (dd, 1H), 8.54 (dd, 1H), 10.29 (s, 1H).

Step F

The acetylated product (0.1572 g, 0.58 mmoles) from Step E was dissolved in $CH_2Cl_2$ (3 mL) and methyl (triphenylphosphoranylidene)-acetate (0.2141 g, 0.64 mmoles) was added under $N_2$. The mixture was stirred at ambient temperature for 1.5 hrs. The reaction was concentrated in vacuo to give a white/yellow solid. The solid was purified by plate layer chromatography with 5% hexane/$CH_2Cl_2$ to give the desired ester as a white solid (0.1688 g).

¹H NMR (CDCl₃) δ: 2.54 (s, 3 H), 3.86 (s, 3H), 6.67 (d, 1H), 7.24 (d, 1H), 7.48 (t 2H), 7.66 (d, IH), 7.77 (d, 1H), 7.95 (d, 1H), 8.28 (d, 1H).

Step G

To a solution of the ester obtained from Step F (0.1688 g, 0.51 mmoles) in 1:1 EtOAc/EtOH was added 10% Pd/C (0.0186, 10% w/w). The resulting mixture was degassed with $N_2$ and hydrogenated under atmospheric $H_2$ pressure for 3 hrs. The reaction was degassed with $N_2$ and the catalyst removed by filtering through a celite pad. The filtrate was concentrated in vacuo to give a white/yellow solid (0.1595 g).

¹H NMR (CDCl₃) δ: 2.53 (s, 3 H), 2.80 (t, 2H), 3.21 (t, 2H), 3.70 (s, 3H), 7.21 (t, 1H), 7.31 (d, 1H), 7.40-7.49 (m, 2H), 7.73 (dd, 1H), 8.12 (dd, 1H).

Step H

The alkyl ester isolated from Step G (0.1595 g, 0.49 mmoles) was dissolved in absolute EtOH (2 mL), and 5 N NaOH (0.29 mL, 1.5 mmoles) was added under $N_2$. The resulting yellow mixture was heated to 70° C. After 1 hr, the reaction was partitioned between ice/1 M HCl and EtOAc. The organic layer was washed with brine, dried over $Na_2SO_4$, and concentrated in vacuo to afford the desired acid as a pale yellow solid (0.1614 g).

¹H NMR (CDCl₃+d₆-acetone) δ:2.77 (t, 2H), 3.15 (t, 2H), 6.81 (d, 1H), 7.18–7.26 (m, 2H), 7.32 (t, 1H), 7.32 (d, 1H), 8.52 (d, 1H).

Step I

To a solution of the carboxylic acid generated in Step H (0.1614, 0.49 mmoles) in distilled THF (5 niL) was added dropwise a 1 M solution of $BH_3$.THF in THF (0.98 mL, 0.98 mmoles). Upon addition, gas evolution was observed. With time, the reaction became a cloudy green mixture. The reaction was stirred at ambient temperature for a total of 2 hrs. The reaction was quenched with dropwise addition of MeOH until no further gas evolution was observed. The reaction mixture was concentrated in vacuo and the residue was purified by plate layer chromatography with 5% EtOAc/$CH_2Cl_2$ to give the desired diol as a white solid (0.1065 g).

¹H NMR (CDCl₃+d₆-acetone) δ: 1.88 (m, 2H), 2.81 (t, 2H), 3.57 (t, 2H), 6.74 (d, 1H), 7.08 (t, 2H), 7.10 (d, 1H), 7.21–7.27 (m, 2H), 8.42 (d, 1H), 8.69 (bs, 1 H).

Step J:

Utilizing the procedure described in Example 7 (Step J), the diol obtained from Step I was selectively protected at the primary alcohol position to give the desired TBS-protected product as a yellow oil after plate layer chromatography with 5% EtOAc/$CH_2Cl_2$.

¹H NMR (CDCl₃) δ: 0.07 (s, 3H), 0.92 (s, 6H), 1.99 (m, 2H), 2.92 (t, 2H), 3.70 (t, 2H), 6.74 (d, 1H), 7.24–7.27 (m, 2H), 7.38–7.43 (m, 2H), 8.48 (d, 1H).

PREPARATIVE EXAMPLE 9

Preparation of 1-Hydroxy-5- T-Butyldimethylsilyloxymethyl Dibenzofuran

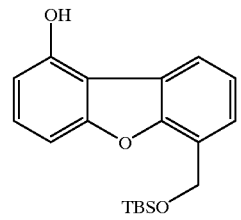

Step A:

To a mixture of 2,6-difluoronitrobenzene (1.0 g, 6.3 mmoles) in MeOH (10 mL) was added a 4.4 M solution of NaOMe in MeOH (1.57 mL, 6.9 mmoles). The mixture was heated to 70° C. for 20 min. The resulting orange reaction mixture was concentrated in vacuo. The residue was dissolved in EtOAc and washed with $H_2O$ and brine. The organic layer was dried over $Na_2SO_4$ and concentrated in vacuo to give a pale yellow solid. The solid was purified by plate layer chromatography with 1:1 hexane/$CH_2Cl_2$ to give clean product as a pale yellow solid (1.0559 g).

¹H NMR (CDCl₃) δ: 3.89 (s, 3H), 6.77–6.85 (m, 2H), 7.36–7.41 (m, 1H).

Step B:

The methoxy nitrobenzene isolated from Step A was coupled with o-cresol (0.64 mL, 6.2 mmoles) using the procedures described in Example 6 (Step A) with the exception that the reaction time was 3 hrs. After purification by plate layer chromatography with 1:1 hexane/$CH_2Cl_2$, the desired adduct was obtained as a pale yellow solid.

$^1$H NMR ($CDCl_3$) δ: 2.18 (s, 3H), 3.91 (s, 3H), 6.27 (d, 1H), 6.66 (d, 1H), 6.98 (d, 1H), 7.10–7.27 (m, 4H).

Step C:

The adduct from Step B (1.3924 g, 5.4 mmoles) was hydrogenated under 40–46 psi of $H_2$ in a Parr Shaker for 5 days using 10% Pd/C (0.139 g, 10 w/w) in 1:1 EtOH/EtOAc. The catalyst was filtered off through a celite pad and the filtrate was concentrated in vacuo. The product was obtained as a yellow oil (1.2833 g).

$^1$H NMR ($CDCl_3$) δ: 2.30 (s, 3H), 3.88 (s, 3H), 6.36 (m, 1H), 6.60 (m, 2H), 6.79 (d, 1H), 6.97 (t, 1H), 7.08 (t, 1H), 7.21 (d, 1H).

Step D:

The amine from Step C was converted to its $KPF_6$ diazonium salt using the procedures described in Example 6 (Step C). The product was isolated as a yellow solid.

$^1$H NMR ($d_6$-acetone) δ: 2.26 (s, 3H), 4.36 (s, 3H), 6.57 (d, 1H), 7.25 (d, 1H), 7.32 (d, 1H), 7.38 (t, 2H), 7.46 (dd, 1H), 8.17 (t, 1H).

Step E:

A mixture of 0.438 g (0.48 mmoles) of $Pd_2(dba)_3$ in anhydrous DMSO (30 mL) was heated to 100° C. under $N_2$ and the diazonium salt from Step D (1.8489 g, 4.8 mmoles) was added in one portion, resulting in significant gas evolution. The reaction was stirred at 100° C. for 40 min and then filtered through celite. The filtrate was paritioned between EtOAc and water. The organic layer was washed well with $H_2O$ (2x) followed by brine. The organic layer was dried over $Na_2SO_4$ and concentrated in vacuo to give a black solid. The solid was purified by plate layer chromatography with 2:1 hexane/$CH_2Cl_2$ to give the desired product as a white solid (0.4335 g).

$^1$H NMR ($CDCl_3$) δ: 2.59 (s, 3H), 4.05 (s, 3H), 6.77 (d, 1H), 7.20–7.27 (m, 3H), 7.35 (t, 1H), 7.95 (dd, 1H).

Step F:

The dibenzofuran from Step E was demethylated and acetylated using the procedures described in Example 6 (Step E) and Example 7 (Step F) respectively. The desired product was obtained as a white solid over the 2 steps.

$^1$H NMR ($CDCl_3$) δ: 2.50 (s, 3H), 2.58 (s, 3H), 7.11 (dd, 1H), 7.21–7.30 (m, 2H), 7.41–7.50 (m, 2H), 7.64 (dd, 1H).

Step G:

0.1126 g (0.49 mmoles) of acetylated dibenzofuran from Step F, recrystallized NBS (0.0970 g, 0.54 mmoles), benzoyl peroxide (0.0271 g, 0.099 mmoles), and $CCl_4$ (3 mL) were combined under $N_2$ and heated to 100° C. In addition to heating, the reaction was illuminated with a sun lamp. Within 30 min., the reaction became dark purple. After 2 hrs, another 0.3 equivalents of NBS and 0.0312 g of benzoyl peroxide were added. The reaction was heated for another 2 hrs, and then partitioned between EtOAc and 5% $Na_2S_2O_3$. The organic layer was washed with $H_2O$ and brine, dried over $Na_2SO_4$, and concentrated in vacuo to give a dark purple solid. The solid was purified by plate layer chromatography with 2:1 $CH_2Cl_2$/hexane to afford the desired alkyl bromide as an off-white solid (0.081 g).

$^1$H NMR ($CDCl_3$) δ: 2.50 (s, 3H), 4.84 (s, 2H), 7.16 (dd, 1H), 7.30 (t, 1H), 7.47–7.55 (m, 3H), 7.77 (dd, 1H).

Step H:

The diacetate was prepared after plate layer chromatography with 2:1 CH2Cl2/hexane, from the alkyl bromide of Step G using the procedures described in Example 7 (Step H).

$^1$H NMR ($CDCl_3$) δ: 2.14 (s, 3H), 2.51 (s, 3H), 5.49 (s, 2H), 7.15 (dd, 1H), 7.32 (t, 1H), 7.44–7.52 (m, 3H), 7.80 (dd, 1H).

Step I:

The diacetate from Step H was treated under the same conditions as Example 7 (Step I) to give the crude diol.

$^1$H NMR ($CDCl_3$+$CD_3OD$) δ: 5.00 (s, 2H), 6.67 (d, 1H), 7.03 (d, 1H), 7.19–7.30 (m, 2H), 7.38 (dd, 1H), 8.02 (dd, 1H).

Step J:

The diol from Step I was selectively protected at the primary position using the procedures described in Example 7 (Step J) to give the desired product as a white solid after plate layer chromatography with 2:1 $CH_2Cl_2$/hexane.

$^1$H NMR ($CDCl_3$) δ: 0.15 (s, 3H), 0.97 (s, 6H), 5.15 (s, 2H), 6.68 (d, 1H), 7.15 (d, 1H), 7.25 (t, 1H), 7.33 (t, 1H), 7.53 (d, 1H), 7.98 (d, 1H).

PREPARATIVE EXAMPLE 10

Preparation of 3-Hydroxybiphenyl

A stirred mixture of 660 mg (3 mmol) of 3-iodophenol, 439 mg (3.6 mmol) phenylboronic acid, and 173 mg (0.15 mmol) tetrakistriphenylphosphine in 10 mL of toluene, 5 mL ethanol, and 6 mL 2M sodium carbonate (aqueous) was heated at 100° C. in an inert atmosphere of nitrogen for 15 minutes. The cooled mixture was partitioned between EtOAc, ice, and brine and the organic phase was separated, washed with brine, dried over anhydrous $Na_2SO_4$, filtered and evaporated. The residue was purified by plate layer chromatography (PLC) using $CH_2Cl_2$ as the eluant to give 430 mg of the titled product.

$^1$H NMR ($CDCl_3$) δ: 1.26 (d, J=7.3 Hz,3H), 1.47 (d, J=6.3 Hz, 3H), 3.47 (dd, J=3.0, 11 Hz, 1H-6), 3.50 (m, 1H-1), and 4.2 (dd, J=3.0, 10 Hz, 1H-5).

PREPARATIVE EXAMPLE 11

Preparation of 4'-T-Butyldiphenylsilyloxymethyl-3-Hydroxybiphenyl

As described in Example 10, 391 mg (1 mmol) of 4-t-butyldiphenylsilyloxymethylboronic acid (prepared as exemplified in U.S. Pat. No. 5,192,758) and 220 mg (1 mmol) of 3-iodophenol gave 354.3 mg of the title compound.

PREPARATIVE EXAMPLE 12

Preparation of 4-Hydroxy-fluorene

A partial solution of 196.2 mg (1 mmol) of 4-hydroxy-fluoren-9-one in 2 mL EtOAc and 3 mL EtOH with 40 mg 10% Pd/C was stirred under a balloon of hydrogen for 27.5 hours. The catalyst was removed by filtration through celite, washed well with EtOAc, and the filtrate evaporated. The residue was purified by plate layer chromatography with $CH_2Cl_2$-EtOAc(50:1) to give 102.7 mg of the title substance.

$^1$H NMR ($d_6$-acetone) δ: 3.88 (s, $CH_2$).

PREPARATIVE EXAMPLE 13

Preparation of 4-Hydroxy-9-Carbomethoxy-Fluorylidene

A stirred mixture of 401 mg (2 mmol) of 4-hydroxy-fluoren-9-one and 1.37 g (4.1 mmol) of methyl- (triphenylphosphoranylidene)-acetate in 10 mL of toluene was refluxed under an atmosphere of nitrogen for 65.5 hours. The cooled reaction mixture was evaporated and the residue purified by plate layer chromatography using $CH_2Cl_2$-EtOAc (50:1) as eluant to give 433 mg of the title compound as a mixture of isomers.

$^1$H NMR (CDCl$_3$) δ: 3.87 (s, 3H), 3.88 (s, 3H), 6.74–8.89 (m, 8H).

PREPARATIVE EXAMPLE 14

Preparation of 4-Hydroxy-9-Carbomethoxymethyl-Fluorene

A stirred mixture of 348 mg (1.38 mmol) of the fluorylidene derivative prepared in Example 28, Step A, and 50 mg of 10% Pd/C in 10 mL of EtOAc-EtOH (1:1) was hydrogenated under balloon pressure at ambient temperature for 2.5 hours. The catalyst was removed by filtration through celite, washed well with EtOAc, and the filtrate evaporated and dried in vacuo to give 348.5 mg of the title product.

$^1$H NMR (CDCl$_3$) δ: 2.77 (d, J=7.3 Hz, 2H), 3.79 (s, 3H), 4.42 (t, J=7.3 Hz, 1H), 5.6 (s, OH), 6.72–8.09 (m, 7ArH).

PREPARATIVE EXAMPLE 15

Preparation of 4-Hydroxy-9-Silyoxyethyl-Fluorene
Step A: Preparation of 4-Hydroxy-9-hydroxyethyl-fluorene To a stirred solution of 277.5 mg (1.09 mmol) of the ester prepared in Example 14 in 5 mL of anhydrous THF at 0° C. was added dropwise 1.1 mL (1.1 mmol) of a 1M solution of lithium aluminum hydride in ether. The resulting mixture was stirred at 0° C. under nitrogen for 1.5 hours and then carefully quenched with Glaubers salt. The mixture was partitioned between EtOAc, ice, 2N HCl, and brine and the organic phase was separated, washed with brine, dried over $Na_2SO_4$, filtered, and evaporated. The residue was purified by PLC with $CH_2Cl_2$-EtOAc (10:1) to give 236.8 mg of the title compound.

$^1$H NMR (CDCl$_3$) δ: 2.33 (q, J=6.8 Hz, 2H), 3.57 (t, J=6.8 Hz, 2H), 4.13 (t, J=6.8 Hz), 6.08 (s, OH), 6.68–8.13 (m, 7ArH).
Step B:

A mixture of 236.8 mg (1.05 mmol) of carbinol, prepared in the previous step, 173.5 mg (1.15 mmol) of t-butyldimethylchlorosilane, and 85.5 mg (1.26 mmol) of imidazole in 5 mL of sieve-dried DMF was stirred at 0° C. under nitrogen for 40 minutes. The mixture was partitioned between EtOAc, ice, 2N HCl, and the organic phase was separated, washed twice with ice-water and then with brine, dried over $Na_2SO_4$, filtered, and evaporated. The residue was purified by PLC with $CH_2Cl_2$-EtOAc (50:1) to give 325.1 mg of the title compound.

$^1$H NMR (CDCl$_3$) δ: 0.03 (s, 6H), 0.88 (s, 9H), 2.19 (m, 2H), 3.67 (t, J=6.8 Hz, 2H), 4.13 (t, J=6.4 Hz), 5.12 (s, OH), 6.71–8.10 (m, 7ArH).

PREPARATIVE EXAMPLE 16

Preparation of 4-Hydroxy-9-E,Z-T-Butyldimethylsilyloxyethenyl-Fluorene
Step A: Preparation of 4-Acetoxy-9-(2-t-butyldimethylsilyloxyethyl)-fluorene To a stirred solution of a mixture of 1.91 g (5.6 mmol) of the phenol, prepared in Step B of Example 15, and 736.6 mg (7.28 mmol) of triethylamine in 20 mL of $CH_2Cl_2$ at 0° C. was added 527.5 mg (6.72 mmol) of neat acetyl chloride and the mixture was stirred further for 0.5 hour. The mixture was partitioned between EtOAc, ice, 1N HCl, and brine and the organic phase was separated, washed with brine, dried over $Na_2SO_4$, filtered, evaporated, and dried in vacuo to give 2.14 g of crude product which was used without further purification.

$^1$H NMR (CDCl$_3$) δ: 0.86 (s, 9H), 2.47 (s, 3H).
Step B: Preparation of 4-Acetoxy-9-bromo-9-(2-t-butyldimethylsilyloxyethyl)-fluorene A mixture of 2.14 g (5.6 mmol) of material prepared in the previous step, 1.2 g (6.72 mmol) of N-bromosuccinimide, and a pinch of AIBN in 20 mL of carbon tetrachloride was refluxed under nitrogen for 1.5 hours. The cooled mixture was partitioned between EtOAc, ice, 5% aqueous sodium thiosulfate, and brine and the organic phase was separated, washed with brine, dried over $Na_2SO_4$, filtered, evaporated, and dried in vacuo to give the crude, title product which was used without further purification.

$^1$H NMR (CDCl$_3$) δ: 0.73 (s, 9H), 2.47 (s, 3H), 2.91 (m, 2H), 3.20 (m, 2H).
Step C: Preparation of 4-Acetoxy-9-E,Z-t-butyldimethylsilyloxyethenyl-fluorene A mixture of the crude product from the previous step, 913 mg (10.9 mmol) of NaHCO$_3$, and 1.54 g (5.98 mmol) of silver triflate in 25 mL DMSO was stirred at room temperature for 15 minutes. The mixture was diluted with EtOAc, filtered through celite to remove the insoluble materials, and washed thoroughly with EtOAc. The filtrate was partitioned between EtOAc, ice, and brine and the organic phase was separated, washed twice with ice-water, and then with brine, dried over $Na_2SO_4$, filtered, evaporated, and dried in vacuo. Purification by PLC eluted with $CH_2Cl_2$-hexanes (1:1) gave 1.22 g of product, as a mixture of geometric isomers.

$^1$H NMR (CDCl$_3$) δ: 0.17 (s, 6H), 0.98 (s, 9H), 2.48 (s, 3H), 5.02 (m, 2H).
Step D:

To a stirred, warm solution of 1.19 g (3.13 mmol) of acetate, prepared in the previous step, in 20 mL EtOH was added dropwise 0.77 mL (3.85 mmol) of a 5N solution of sodium hydroxide in water. The resulting dark solution was stirred further for 5 minutes and then partitioned between EtOAc, ice, 1N HCl, and brine. The organic phase was separated, washed with brine, dried over $Na_2SO_4$, filtered, evaporated, and dried in vacuo. Purification by PLC eluted with $CH_2Cl_2$gave 890.0 mg of product, as a mixture of geometric isomers.

$^1$H NMR (CDCl$_3$) δ: 0.15 (s, 6H), 0.96 (s, 9H), 4.98 (m, 2H), 5.18 & 5.22 (2s's, 1-OH), 6.68–8.1 (m, 8H).

PREPARATIVE EXAMPLE 17

Preparation of 4-Hydroxy-7-T-Butyldimethylsilyloxymethyl-Fluoren-9-One
Step A: Preparation of 2-Methoxy-6-carbomethoxy-4'-t-butyldiphenylsilyloxymethylbiphenyl Using the procedure described Example 10, 10.0 g (34.2 mmol) of methyl-2-iodo-3-methoxybenzoate (prepared as outlined by W. M. Stanley, E. McMahon, and R. Adams, *J. Amer. Chem. Soc.* 1933, 55, 706) was refluxed for 5 hours to give after chromatography on silica gel with $CH_2Cl_2$-hexanes (2:1) 12.1 g of the title compound.

$^1$H NMR (CDCl$_3$) δ: 1.14 (s, 9H), 3.57 (s, 3H), 3.78 (s, 3H), 7.1–7.77 (m, ArH).
Step B: Preparation of 2-Methoxy-4'-hydroxymethylbiphenyl-6-carboxylic acid A stirred mixture of 6.0 g (11.7 mmol) of biphenyl derivative prepared in Step A and 4.7 mL of 5N NaOH in 100 mL of EtOH was refluxed in an inert atmosphere of nitrogen for 4 hours. The mixture was partitioned between EtOAc, ice, 2N HCl, and the organic phase was separated, washed with brine, dried over $Na_2SO_4$, filtered, evaporated, and dried in vacuo. Upon addition of a little $CH_2Cl_2$ the product crystallized and after the addition of some hexanes 1.95 g of the product was collected by filtration and dried in vacuo.

$^1$H NMR ($d_6$-acetone) δ: 3.74 (s, 3H), 4.64 (s, 2H), 7.17–7.44 (m, 7ArH).

Step C: Preparation of 4-Methoxy-7-chloromethyl-fluoren-9-one

To a stirred suspension of 2.0 g (7.74 mmol) of acid prepared in Step B in 40 mL of sieve-dried $CH_2Cl_2$ at 0° C. was added all at once 3.55 g (17.0 mmol) of phosphorous pentachloride and the mixture was stirred further for 5 minutes, and then for 1 hour with the ice-water bath removed. The homogenous solution was recooled to 0° C., and 1.55 g (11.6 mmol) of $AlCl_3$ was added all at once. The resulting mixture was stirred further for 0.5 hour and then partitioned between EtOAc, ice, and brine. The organic phase was separated, washed with brine and saturated $NaHCO_3$, dried over $Na_2SO_4$, filtered, evaporated, and dried in vacuo to give 2.04 g of the title material as a yellow solid, which was used without further purification.

IR ($CH_2Cl_2$): 1717.5 $cm^{-1}$;
$^1$H NMR ($CDCl_3$) δ: 3.90 (s, 3H), 4.53 (s, 2H), 6.94–7.68 (m, 6ArH).

Step D: Preparation of 4-Methoxy-7-acetoxymethyl-fluoren-9-one

A mixture of 2.0 g (7.7 mmol) of material prepared in Step C and 1.52 g (15.5 mmol) of potassium acetate in 30 mL of DMF was stirred at 100° C. under nitrogen for 36 minutes. The cooled mixture was partitioned between EtOAc and ice-water and the organic phase was separated, washed twice with ice-water, and then with brine, dried over $Na_2SO_4$, filtered, evaporated, and dried in vacuo to give 2.17 g of the title material as a yellow solid, which was used without further purification.

IR ($CH_2Cl_2$): 1742, 1718 $cm^{-1}$;
$^1$H NMR ($CDCl_3$) δ: 2.12 (s, 3H), 3.99 (s, 3H), 5.10 (s, 2H), 7.04–7.81 (m, 6ArH).

Step E: Preparation of 4-Methoxy-7-hydroxymethyl-fluoren-9-one

A stirred mixture of the acetate prepared above and 3.07 mL (15.4 mmol) of 5N NaOH in 100 mL of EtOH was refluxed under nitrogen for 10 minutes. The cooled mixture was partitioned between EtOAc, ice-water and 2N HCl, and the organic phase was separated, washed with brine, dried over $Na_2SO_4$, filtered, evaporated, and dried in vacuo to give 2.07 g of the title material as a yellow solid, which was used without further purification.

$^1$H NMR ($CDCl_3$) δ: 3.96 (s, 3H), 4.68 (s, 2H), 7.01–7.77 (m, 6ArH).

Step F: Preparation of 4-Methoxy-7-formyl-fluoren-9-one

To a stirred suspension of 1.85 g (7.69 mmol) of carbinol from Step E in 50 mL $CH_2Cl_2$ was added 270.1 mg (0.769 mmol) of tetrapropylammonium perruthenate. After stirring for 5 minutes, 1.35 g (11.5 mmol) of solid N-methylmorpholine-N-oxide was added all at once, and the resulting mixture stirred further for 5 minutes. The dark solution was passed over a column of florisil eluted with $CH_2Cl_2$-EtOAc (10:1) to give 1.42 g of the title aldehyde as a yellow solid.

IR ($CH_2Cl_2$): 1720, 1698 $cm^{-1}$;
$^1$H NMR ($CDCl_3$) δ: 4.02 (s, 3H), 7.09–8.1 (m, 6ArH), 10.0 (s, 1H).

Step G: Preparation of 4-Hydroxy-7-formyl-fluoren-9-one

A stirred mixture of the methylether from the previous step and 30 mL of 48% HBr in 15 mL of acetic acid was heated at 130° C. under nitrogen for 7 hours. The cooled mixture was poured onto ice-water and the separated product collected by suction filtration, washed well with water, and dried in vacuo to give 0.94 g of the title compound.

$^1$H NMR ($d_6$-acetone) δ: 7.18–8.15 (m, 6ArH), 9.8 (s, 1-OH), 10.07 (s,1-CHO).

Step H: Preparation of 4-Hydroxy-7-hydroxymethyl-fluoren-9-one

A stirred mixture of 405.2 mg (1.8 mmol) of aldehyde prepared in Step G and 804.3 mg (3.8 mmol) of sodium triacetoxyborohydride in 27 mL of anhydrous THF was refluxed under nitrogen for 1 hour. The cooled mixture was partitioned between EtOAc, ice-water and saturated $NaHCO_3$, and the organic phase was separated, washed with brine, dried over $Na_2SO_4$, filtered, evaporated, and dried in vacuo. Purification by PLC with $CH_2Cl_2$-EtOAc (2:1) yielded 303.7 mg of the crystalline, title product.

$^1$H NMR ($d_6$-acetone) δ: 4.66 (s,2H), 7.08–7.86 (m, 6ArH), 9.38 (s, 1-OH).

Step I:

A mixture of 332.2 mg (1.47 mmol) of the diol from Step H, 243.5 mg (1.61 mmol) of t-butyldimethylchlorosilane, and 120 mg (1.76 mmol) of imidazole in 8 mL of sieve dried DMF was stirred at 0° C. for 45 minutes. The mixture was partitioned between EtOAc, ice-water and 2N HCl, and the organic phase was separated, washed twice with ice-water, and then with brine, dried over $Na_2SO_4$, filtered, evaporated, and dried in vacuo. Purification by PLC using $CH_2Cl_2$-EtOAc (50:1) gave 447.4 mg of the title material.

$^1$H NMR ($d_6$-acetone) δ: 0.14 (s, 6H), 0.95 (s, 9H), 4.81 (s,2H), 7.08–7.86 (m, 6ArH), 9.35 (bs, 1-OH).

PREPARATIVE EXAMPLE 18

Preparation of 4-Hydroxy-7-(3 -T-Butyldimethylsilyloxypropyl)-Fluoren-9-One

Step A: Preparation of 4-Acetoxy-7-formyl-fluoren-9-one

To a stirred suspension of 1.53 g (6.83 mmol) of 4-hydroxy-7-formyl-fluoren-9-one, prepared in Step G of Example 43, in 25 mL THF at 0° C. was added 1.24 mL (8.88 mmol) of triethylamine and 0.58 mL (8.2 mmol) of acetyl chloride. The mixture was stirred further for 0.5 hour and then partitioned between EtOAc, ice, 1N HCl, and brine. The organic phase was separated, washed with brine, dried over $Na_2SO_4$, filtered, evaporated, and dried in vacuo. Purification by chromatography on silica gel using methylene chloride as eluant gave 1.46 g of the title compound.

IR ($CH_2Cl_2$): 1772, 1724, 1702, 1618, 1606 $cm^{-1}$;
$^1$H NMR ($CDCl_3$) δ: 2.48 (s, 3H), 7.38–8.15 (m, 6ArH), 10.0 (s, 1H).

Step B: Preparation of 4-Acetoxy-7-(E-2-carbomethoxyvinyl)-fluoren-9-one

A mixture of 1.46 g (5.49 mmol) of aldehyde, prepared in Step A, and 2.02 g (6.04 mmol) of methyl-(triphenylphosphoranylidene)-acetate in 25 mL of methylene chloride was stirred at room temperature for 1 hour, during which time product precipitation was progressive. Ether-hexanes (2:1, 20 mL) was added and the yellow solid was collected by suction filtration, washed with 60 mL of ether-hexanes (2:1), and dried in vacuo to give 1.43 g of the title material.

$^1$H NMR ($CDCl_3$) δ: 2.48 (s, 3H), 3.82 (s, 3H), 6.49 (d, J=16 Hz, 1H), 7.30–7.87 (m, 6ArH), 7.68 (d, J=16 Hz, 1H).

Step C: Preparation of 4-Acetoxy-7-(2-carbomethoxyethyl)-fluoren-9-one

The material prepared above in Step B, 1.11 g (3.45 mmol) and 267 mg of 5% Rh/C in 60 mL methylene chloride and 12 mL methanol was stirred under balloon pressure of hydrogen for 5 hours. The catalyst was removed by filtration through celite, washed well with methylene chloride, and the filtrate evaporated and dried in vacuo to give 1.1 g of product which was used without further purification.

$^1$H NMR (CDCl$_3$) δ: 2.46 (s, 3H), 2.65 (t, J=7.5 Hz, 2H), 2.98 (t, J=7.5 Hz, 2H), 3.67 (s, 3H), 7.23–7.56 (m, 6ArH).

Step D: Preparation of 2-(4-Hydroxy-7-fluoren-9-one) propionic acid

A stirred mixture of 1.27 g (3.92 mmol) of ester, prepared in Step C above, and 2.43 mL (12.2 mmol) of 5N NaOH in 30 mL of EtOH was refluxed under nitrogen for 70 minutes. The cooled mixture was partitioned between EtOAc, ice, 2N HCl, and brine, and the organic phase was separated, washed with brine, dried over Na$_2$SO$_4$, filtered, evaporated, and dried in vacuo to give 1.04 g of the title acid.

$^1$H NMR (d$_6$-acetone) δ: 2.67 (t, J=7.5 Hz, 2H), 2.97 (t, J=7.5 Hz, 2H), 7.08–7.80 (m, 6ArH), 9.37 (s, bs, 1H).

Step E: Preparation of 4-Hydroxy-7-(3-hydroxypropyl)-fluoren-9-ol

To a stirred suspension of the acid (905.1 mg, 3.38 mmol), prepared above in Step D, in 30 mL of anhydrous THF at ambient temperature was added cautiously 10.1 mL of 1M borane-THF in THF. The resulting mixture was stirred further for 2 hours and carefully quenched with methanol. The mixture was evaporated and the residue partitioned between EtOAc, ice, saturated NaHCO$_3$, and brine, and the organic phase was separated, washed with brine, dried over Na$_2$SO$_4$, filtered, evaporated, and dried in vacuo to give 0.96 g of the title triol.

$^1$H NMR (d$_6$-acetone) δ: 1.85 (m, 2H), 2.74 (t, J=7.4 Hz, 2H), 3.60 (t, J=7.4 Hz, 2H), 5.49 (d, J=6.1 Hz, 1H), 6.83–7.91 (m, 6ArH), 8.88 (s, 1H).

Step F: Preparation of 4-Hydroxy-7-(3-hydroxypropyl)-fluoren-9-one

A stirred mixture of 870 mg (3.38 mmol) of triol, prepared in Step E, and 958 mg (13.5 mmol) of manganese dioxide in 20 mL of acetone was refluxed for 17 hours. The cooled mixture was filtered through celite, washed well with acetone, and the filtrate evaporated and dried in vacuo to give 832.2 mg of the title compound, as a brick-red solid.

$^1$H NMR (d$_6$-acetone) δ: 1.85 (m, 2H), 2.74 (t, J=7.4 Hz, 2H), 3.59 (m, 2H), 7.06–7.79 (m, 6ArH), 9.30 (s, 1H).

Step G:

A mixture of 832.2 mg (3.28 mmol) of diol, prepared in Step F above, 543.2 mg (3.6 mmol) of t-butyldimethylchlorosilane, and 267.7 mg (3.9 mmol) of imidazole in 10 mL sieve-dried DMF was stirred at 0° C. for 45 minutes. The mixture was partitioned between EtOAc, ice, and 2N HCl, and the organic phase was separated, washed twice with ice-water and then with brine, dried over Na$_2$SO$_4$, filtered, and evaporated. The residue was purified by silica gel chromatography using an elution gradient of methylene chloride-ethyl acetate (50:1 to 10:1) to give 1.05 g of the title product.

$^1$H NMR (CDCl$_3$) δ: 0.04 (s, 6H), 0.89 (s, 9H), 1.84 (m, 2H), 2.68 (t, J=6.3 Hz, 2H), 3.62 (t, J=6.3 Hz, 2H), 5.25 (bs, 1H), 5.7 (d, J=15 Hz, 1H), 6.98–7.61 (m, 6ArH)

PREPARATIVE EXAMPLE 19

Preparation of 4-Hydroxy-7-(3-T-Butyldimethylsilyloxypropyl)-9-Carbomethoxy-Fluorylidene A stirred mixture of 110.4 mg (0.3 mmol) of fluorenone derivative prepared in Step G of Example 18 and 250.8 mg (0.75 mmol) of methyl-(triphenylphosphoranylidene)-acetate in 3 mL of p-xylene was refluxed under nitrogen for 21 hours. The cooled mixture was evaporated and the residue purified by PLC with CH$_2$Cl$_2$-EtOAc (50:1) to give 90 mg of the title compound as a mixture of geometric isomers.

$^1$H NMR (CDCl$_3$) δ: 0.07 (s, 6H), 0.92 (s, 9H), 1.87 (m, 2H), 2.73 (m, 2H), 3.65 (t, 2H), 3.87 (s, 3H), 6.71–8.74 (m, 7H).

PREPARATIVE EXAMPLE 20

Preparation of 12-Hydroxy-3,4-Benzocoumarin

Step A: Preparation of Methyl-2,2'-dimethoxy-biphenyl-6-carboxylate

Using the procedure outlined in Example 10, 201.7 mg (0.69 mmol) of methyl-2-iodo-3-methoxy-benzoate and 125.9 mg (0.82 mmol) of 2-methoxy-phenylboronic acid gave after 27 hours of reflux a quantitative yield of the title substance.

$^1$H NMR (CDCl$_3$) δ: 3.56 (s, 3H), 3.71 (s, 3H), 3.73 (s, 3H), 6.95–7.47 (m, 7H).

Step B: Preparation of 2,2'-dimethoxy-biphenyl-6-carboxylic acid

A stirred mixture of 188.4 mg (0.69 mmol) of ester prepared in Step A and 0.28 mL (1.39 mmol) of 5N NaOH in 2 mL of ethanol was refluxed under nitrogen for 1.5 hours. The mixture was partitioned between EtOAc, ice, 2N HCl, and the organic phase was separated, washed with brine, dried over Na$_2$SO$_4$, filtered, evaporated, and dried in vacuo to give 171.6 mg of the title acid which was used without further purification.

$^1$H NMR (d$_6$-acetone) δ: 3.66 (s, 3H), 3.71 (s, 3H), 6.79–7.48 (m, 7H).

Step C: Preparation of 12-Methoxy-3,4-benzocoumarin

To a stirred suspension of 171.6 mg (0.67 mmol) of acid prepared in Step B in 2 mL of sieve-dried CH$_2$Cl$_2$ at 0° C. was added all at once 173.1 mg (0.83 mmol) of phosphorous pentachloride and the mixture was stirred further for 5 minutes, and then for 1 hour with the ice-water bath removed. The homogeneous solution was recooled to 0° C., and 133 mg (0.99 mmol) of AlCl$_3$ was added all at once. The resulting mixture was stirred with the ice-water bath removed for 1 hour and then partitioned between EtOAc, ice, and brine. The organic phase was separated, washed with brine, dried over Na$_2$SO$_4$, filtered, evaporated, and dried in vacuo. Purification by PLC with hexanes-methylene chloride (2:1) provided 134.7 mg of the title compound.

$^1$H NMR (CDCl$_3$) δ: 3.99 (s, 3H), 7.21–8.87 (m, 7ArH).

Step D:

The methylether from Step C in 1 mL acetic acid and 3.4 mL 48% HBr was stirred at 130° C. for 5 hours. The cooled solution was treated with water and the insoluble product collected by filtration, washed well with water, and dried in vacuo to give 131.3 mg of the title product, which was used without further purification.

1H NMR (d$_6$-acetone) δ: 7.33–9.16 (m, 7H), 9.97 (s, 1H).

PREPARATIVE EXAMPLE 21

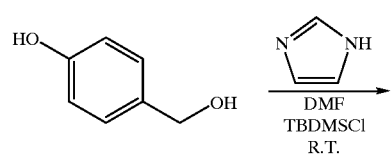

-continued

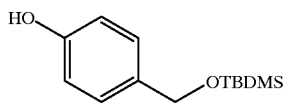

500 mg (4.03 mmoles) of commercially available 4-hydroxybenzyl alcohol was dissolved in 5.0 ml of anhydrous DMF, placed in an $N_2$ atmosphere and chilled to 0° C. To the stirred DMF solution, 301 mg (4.33 mmoles) of imidazole was added followed by 604 mg (4.03 mmoles) of t-butyldimethylsilyl-chloride. The reaction was warmed to ambient temperature and stirred for 18 hrs.

The reaction mixture was extracted with ethyl acetate and partitioned with $H_2O$-dilute aq. sodium bicarbonate and sat. brine. The ethyl acetate extract was dried with anhydrous sodium sulfate and concentrated in vacuo to provide a viscous oil.

The crude product was purified via flash chrom. (230–400 mesh silica gel) and was eluted with a 4:1 mixture of hexanes:ethyl acetate to afford 908 mg of the silyl ether.

$^1$H NMR (CDCl$_3$) δ: 0.10 (s, 6H), 0.94 (s, 9H), 4.66 (s, 2H), 6.08 (s, 1H), 6.72 (d, J=7.5 Hz, 2H), 7.14 (d, J=8.7 Hz, 2H).

PREPARATIVE EXAMPLE 22

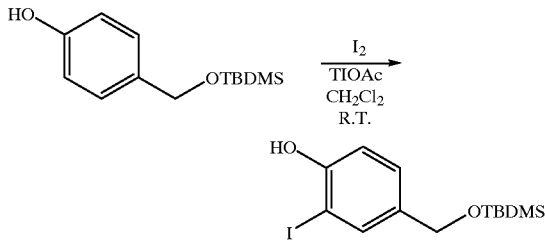

100 mg (0.418 mmoles) of the 4-hydroxy-silyl-ether was dissolved in 2.0 ml of sieve dried dichloromethane and placed in an $N_2$ atmosphere. To the stirred dichloromethane solution, 109 mg (0.418 mmoles) of thallium acetate was added and the tan suspension was stirred for 5 min. at ambient temperature. 109 mg (0.813 mmoles) of iodine was then added. The purple suspension was stirred for 2 hrs. and was filtered through a celite plug and was rinsed with 20 ml of ethyl acetate.

The ethyl acetate extract was partitioned with $H_2O$-ice and 5% aq. sodium thiosulfate and sat. brine. The extract was dried with andyhrous sodium sulfate and concentrated in vacuo to provide 108 mg of a tan solid.

The crude product was purified using plate layer chromatography with a 4:1 hexanes:ethyl acetate eluent to provide 145 mg of the iodophenol.

$^1$H NMR (CDCl$_3$) δ: 0.07 (s, 6H), 0.90 (s, 9H), 4.60 (s, 2H), 5.18 (s, 1H), 6.91 (d, J=8.3 Hz, 1H), 7.15 (dd, J=1.9 Hz, 6.3 Hz, 1H), 7.58 (d, J=3.0 Hz, 1H).

PREPARATIVE EXAMPLE 23

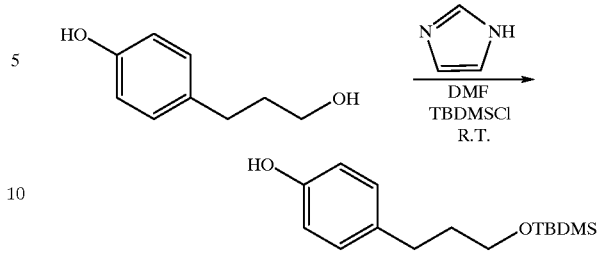

Using the analogous procedure of example 21, the the carbinol was converted to the silyl ether in yield.

PREPARATIVE EXAMPLE 24

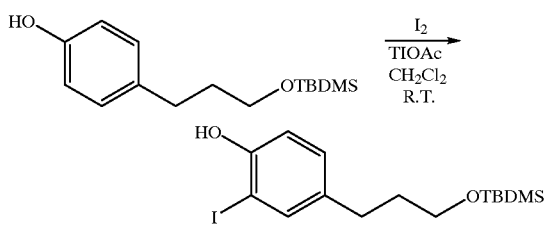

Using the analogous procedure of example 22, the phenol was converted to the iodophenol.

$^1$H NMR (CDCl$_3$) δ: 0.06 (s, 6H), 0.91 (s, 9H), 1.68 (m, 2H), 2.55 (t, J=6.7 Hz, 2H), 3.58 (t, J=6.3 Hz, 2H), 5.22 (s, 1H), 6.88 (d, J=8.2 Hz, 1H), 7.05 (dd, J=2.0 Hz, 6.3 Hz, 1H), 7.48 (d, J=2.0 Hz, 1H).

PREPARATIVE EXAMPLE 25

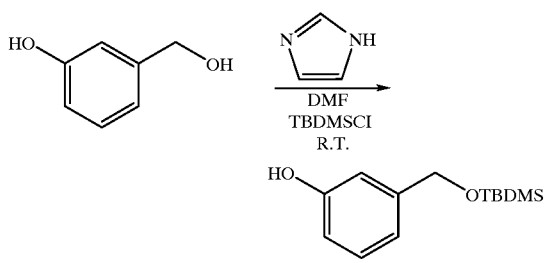

Using the analogous procedure of example 21, the carbinol was converted to the silyl ether.

$^1$H NMR (CDCl$_3$) δ: 0.12 (s, 6H), 0.96 (s, 9H), 5.72 (s, 2H), 6.70 (dd, J=1.9 Hz, 4.7 Hz, 1H), 6.83–6.88 (m, 2H), 7.16 (t, J=7.7 Hz, 1H).

PREPARATIVE EXAMPLE 26

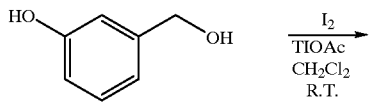

-continued

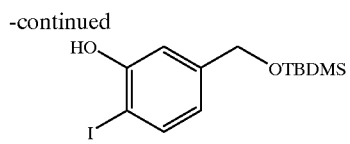

Using the analogous procedure of example 22, the phenol was converted to the iodophenol.

$^1$H NMR (CDCl$_3$) δ: 0.10 (s, 6H), 0.94 (s, 9H), 4.66 (s, 2H), 5.29 (s, 1H), 6.66 (dd, J=1.9 Hz, 4.7 Hz, 1H), 6.97 (d, J=2.0 Hz, 1H), 7.56 (d, J=7.3 Hz, 1H).

PREPARATIVE EXAMPLE 27

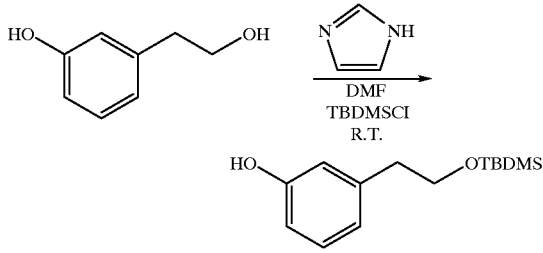

Using the analogous procedure of example 21, the carbinol was converted to the silyl ether.

$^1$H NMR (CDCl$_3$) δ: 0.08 (s, 6H), 0.88 (s, 9H), 2.76 (t, J=7.2 Hz, 2H), 3.78 (t, J=7.2 Hz, 2H), 6.65–6.69 (m, 2H), 6.76 (d, J=7.4 Hz, 1H), 7.12 (t, J=6.5 Hz, 1H).

PREPARATIVE EXAMPLE 28

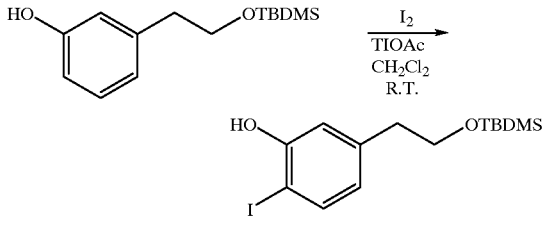

Using the analogous procedure of example 22, the phenol was converted to the iodophenol.

$^1$H NMR (CDCl$_3$) δ: 0.10 (s, 6H), 0.88 (s, 9H), 2.72 (t, J=7.0 Hz, 2H), 3.77 (t, J=6.9 Hz, 2H), 5.49 (s, 1H), 6.53 (dd, J=2.0 Hz, 6.1 Hz, 1H), 6.89 (d, J=2.0 Hz, 1H), 7.52 (d, J=8.0 Hz, 1H).

PREPARATIVE EXAMPLE 29

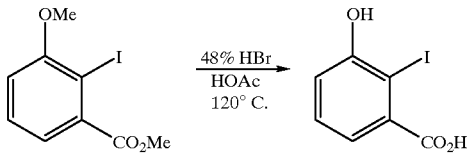

500 mg (1.712 mmoles) of the methyl ester (Stanley, W., M.; McMahan, E.; Adams, R. JACS, 1933, 55, 706) was dissolved in 2.9 ml of 48% HBr and 1.49 ml of acetic acid and was placed in an N$_2$ atmosphere. The reaction was stirred for 4 hrs. at 120° C. The cooled reaction mixture was basified to pH 10.0 with 2 ml of 5N aq. sodium hydroxide and partitioned with ethyl acetate-H$_2$O and ice. The aq. layer was saved and acidified to pH 2.5 with 2.0 N aq. hydrochloric acid, forming a white solid that precipitated from solution. The solid was collected in a sintered glass funnel, washed with 10 ml of deionized H$_2$O and dried in vacuo to provide 286 mg of benzoic acid.

$^1$H NMR (d$_6$-Me$_2$CO) δ: 7.06 (m, 1H), 7.29 (t, J=8.0 Hz, 1H), 7.51 (dd, J=1.5 Hz, 5.9 Hz, 1H).

PREPARATIVE EXAMPLE 30

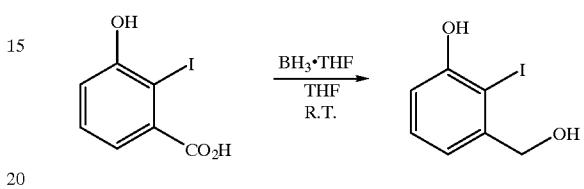

286 mg (1.08 mmoles) of benzoic acid was dissolved in 5.0 ml of anhydrous THF and was placed in an N$_2$ atmosphere. To the stirred THF solution, 2.16 ml of borane-THF complex was added dropwise over 20 min. and the reaction was stirred for 2 hrs. at ambient temperature. 10 ml of methanol was then added to the THF solution slowly over 1 hr.

The reaction was extracted with ethyl acetate and partitioned with H$_2$O-ice and sat. brine. The ethyl acetate extract was dried with anhydrous sodium sulfate and concentrated in vacuo to dryness. The crude product was purified using silica gel plate layer chromatography eluted with a 7:3 ethyl acetate:hexanes mixture to afford 120 mg of the benzyl alcohol.

PREPARATIVE EXAMPLE 31

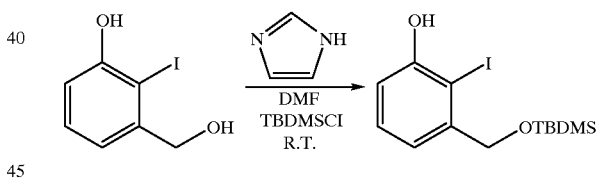

Using the analogous procedure of example 21, the carbinol was converted to the silyl ether.

0.10 (s, 6H), 0.95 (s, 9H), 4.70 (s, 2H), 4.94 (s, 1H), 6.68 (dd, J=2.3 Hz, 5.5 Hz, 1H), 6.83 (m, 1H), 7.16 (t, J=7.8 Hz, 1H).

PREPARATIVE EXAMPLE 32

Preparation of 4(R)- Acetoxy-3-[(R)-1-(T-Butyldiphenylsilyloxy)Ethyl]-Azetidin-2-One

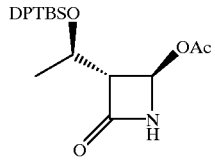

A mixture of 2.08 g (12 mmol) of 4(R)-acetoxy-3-[(R)-1-hydroxyethyl]-azetin-2-one, 4.28 g (15.6 mmol) of t-butyldiphenylchlorosilane, and 1.22 g (18 mmol) of imidazole in 20 mL of sieve dried DMF was stirred at ambient temperature in an inert atmosphere of nitrogen for two days. The reaction mixture was partitioned between ether, ice-water, and 2N HCl and the organic phase separated, washed twice with ice-water, and then brine, dried over anhydrous sodium sulfate, filtered, evaporated, and dried in vacuo. The white solid residue was recrystallized from boiling CH₂Cl₂-hexanes to give 3.78 g of the the title product; a second crop of 0.74 g of additional product was obtained from the mother liquors; total yield 4.52 g.

$^1$H NMR (CDCl₃) δ: 1.03 (s, 9H), 1.12 (d, J=6.3 Hz, 3H), 3.21 (dd, J=1.3, 5.7 Hz, 1H-3), 4.21 (m, 1H), 5.82 (d, J=1.3 Hz, 1H-4), 6.69 (bs, NH), 7.39–7.74 (m, ArH).

PREPARATIVE EXAMPLE 33

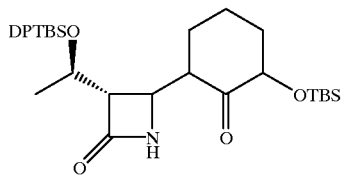

To a stirred solution of 2-t-butyldimethylsilyloxy-cyclohexanone (1.14 g, 5 mmol) in 10 mL of sieve dried CH₂Cl₂ at 0° C. was added sequentially 0.56 g (5.5 mmol) of triethylamine and then 1.67 g (7.5 mmol) of trimethylsilyltriflate. The resulting mixture was stirred cold for 5 minutes, and 1.03 g (2.5 mmol) of the azetidinone prepared in the previous example. The ice-water bath was removed and the mixture stirred further for 3 hours. The mixture was partitioned between ether, ice-water, and 2N HCl and the organic phase separated, washed with brine, dried over anhydrous sodium sulfate, filtered, and evaporated. The residue was purified by PLC eluting with CH₂Cl₂-EtOAc (50:1) to give 501.5 mg of a mixture of α-isomers, and 363.4 mg of β-isomers.

PREPARATIVE EXAMPLE 34

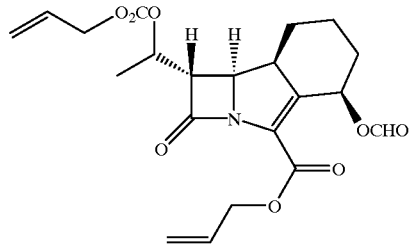

To a stirred solution of 117.3 mg (0.3 mmol) of trinem carbinol, prepared as described in EP 507,313, 102.3 mg (0.39 mmol) of triphenyl phosphine, and 15.2 mg (0.33 mmol) of anhydrous formic acid in 2 mL of anhydrous THF at 0° C. is added 78.9 mg (0.39 mmol) of neat diisopropylazodicarboxylate. The reaction is stirred until thin layer chromatography indicated the reaction is complete and the solvent is removed by evaporation under reduced pressure. Purification by conventional silica gel chromatography provides the corresponding formate ester.

PREPARATIVE EXAMPLE 35

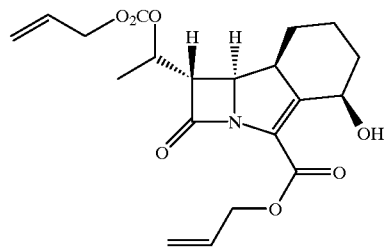

A mixture of 83.8 mg (0.2 mmol) of formate ester prepared in the previous example and 33.6 mg (0.4 mmol) of sodium bicarbonate in 3 mL of methanol is stirred magnetically until TLC indicates the reaction is complete. The mixture is partitioned between ethyl acetate, ice water, brine, and 2N HCl. The organic phase is separated, dried over sodium sulfate, filtered, and evaporated to give the corresponding alcohol derivative.

PREPARATIVE EXAMPLE 36

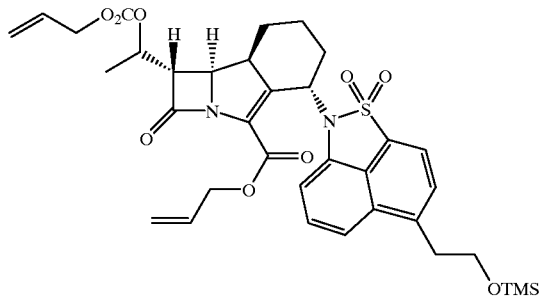

To a stirred solution of 78.2 mg (0.2 mmol) of the carbinol prepared in the previous example, 68.2 mg (0.26 mmol) of triphenylphosphine, and 70.6 mg (0.22 mmol) of the naphthosultam derivative prepared in example 3 in 2 mL of dry THF at 0° C. is added 52.6 mg (0.26 mmol) of diisopropylazodicarboxylate. The mixture is stirred cold until TLC indicates the reaction is complete. The solvent is evaporated and the product is isolated by purification on silica gel.

PREPARATIVE EXAMPLE 37

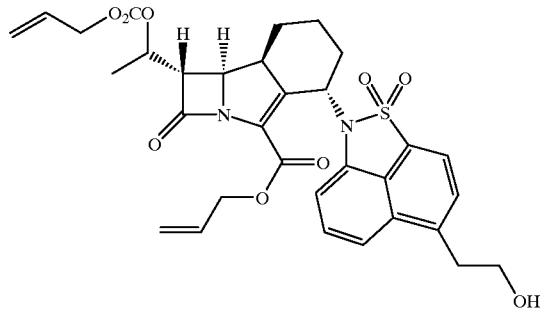

To a stirred solution of 135 mg (0.195 mmol) of the product of the previous example in 3 mL of THF at 0° C. is added 0.97 mL of 0.1M aqueous triflic acid. The resulting mixture is stirred cold until TLC indicates the absence of starting material. The mixture is partitioned between ethyl acetate, ice water, brine, and saturated sodium bicarbonate solution. The organic phase is separated, dried over sodium sulfate, filtered, and evaporated. The product is purified by silica gel chromatography.

PREPARATIVE EXAMPLE 38

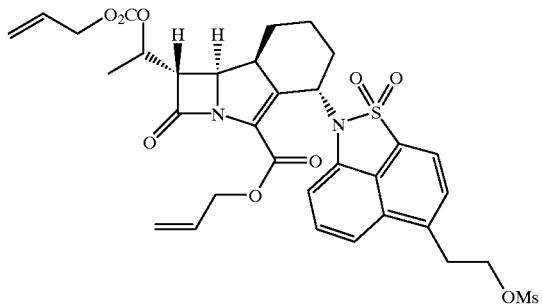

To a stirred solution of 121 mg (0.195 mmol) of alcohol from the previous example and 29.5 mg (0.29 mmol) of triethylamine in 2 mL of methylene chloride at 0° C. is added dropwise 29 mg (0.25 mmol) of mesyl chloride. The mixture is stirred further until TLC shows no remaining alcohol. The mixture is partitioned between ethyl acetate, ice water, brine, and 2N HCl. The organic phase is separated, dried over sodium sulfate, filtered, and evaporated to give the corresponding mesylate derivative, which is used without further purification.

PREPARATIVE EXAMPLE 39

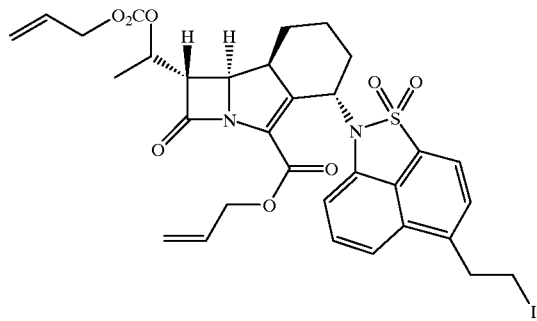

A mixture of 136.2 mg (0.195 mmol) of the mesylate prepared in the previous example and 58.3 mg (0.389 mmol) of sodium iodide in 3 mL of acetone is stirred at ambient temperature until TLC indicates that the reaction is complete. The mixture is partitioned between ethyl acetate, ice water, and brine. The organic phase is separated, dried over sodium sulfate, filtered, and evaporated to give the corresponding iodide derivative, which is used without further purification.

PREPARATIVE EXAMPLE 40

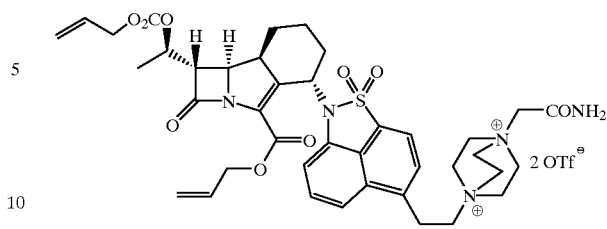

A mixture of 142.6 mg (0.195 mmol) of the iodide prepared in the previous example, 62.1 mg (0.195 mmol) of dabco acetamide triflate salt, and 50 mg (0.195 mmol) of silver triflate in 2 mL of acetonitrile is stirred at room temperature until TLC shows no remaining iodide. The insoluble materials are removed by filtration through celite, washed well with acetonitrile, and the filtrate is evaporated. The residue is taken up in methylene chloride and the product is precipitated by the addition of ether. The precipitate is collected and dried in vacuo to give the desired product.

EXAMPLE 1

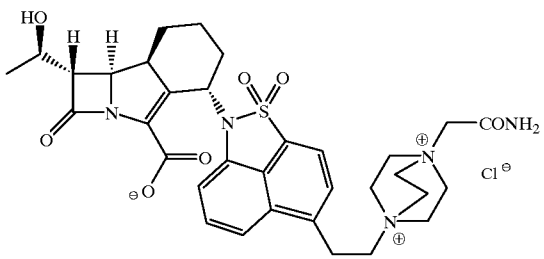

A mixture of 107.4 mg (0.1 mmol) of the product of the previous example, 15.7 mg (0.06 mmol) of triphenylphosphine, 21.1 mg (0.02 mmol) of tetrakistriphenylphosphinepalladium (0), 15.9 mg (0.11 mmol) of 2-ethylhexanoic acid, and 0.22 mL of a 0.5M solution of sodium-2-ethylhexanoate in ethyl acetate in 2 mL of DMF is stirred at ambient temperature for one hour. Ether is added to the mixture and the separated material is collected by centrifugation and decantation of the supernatant. The solid is washed similarly with ether and dried. The product is purified by ion exchange chromatography on MACROPREP resin with 5% NaCl solution, followed by desalting on AMBERCHROM CG 161 resin. The eluant containing the product is concentrated in vacuo and freeze-dried to give the final product.

EXAMPLE 2

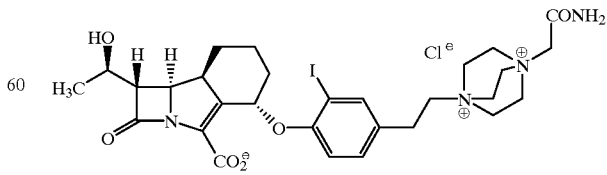

Following the procedure outlined in preparative example 36, with the phenol prepared in preparative example 28, and subsequently following the processes of preparative examples 37–40, and example 1, the product depicted is prepared.

EXAMPLE 3

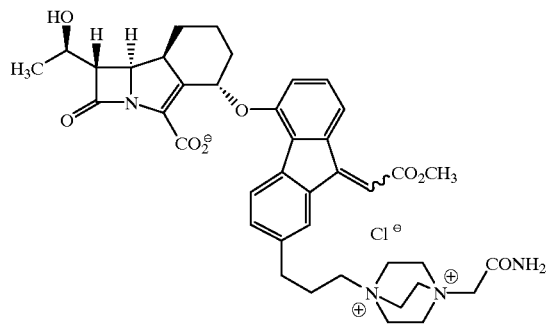

Following the procedure outlined in preparative example 36, with the phenol prepared in preparative example 19, and subsequently following the processes of preparative examples 37–40, and example 1, the product depicted is prepared.

EXAMPLE 4

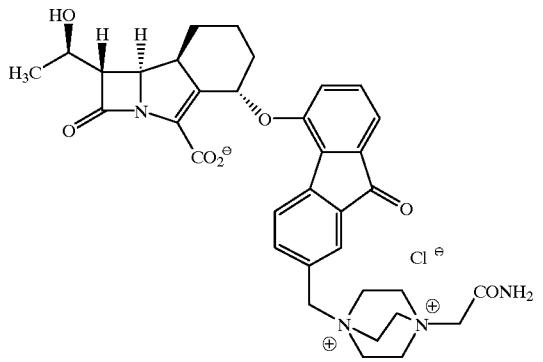

Following the procedure outlined in preparative example 36, with the phenol prepared in preparative example 17, and subsequently following the processes of preparative examples 37–40, and example 1, the product depicted is prepared.

EXAMPLE 5

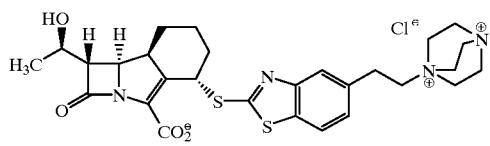

Following the procedure outlined in preparative example 36, with the mercaptobenzothiazole derivative prepared according to U.S. Pat. No. 5,496,816, and subsequently following the processes of preparative examples 37–40, and example 1, the product depicted is prepared.

EXAMPLE 6

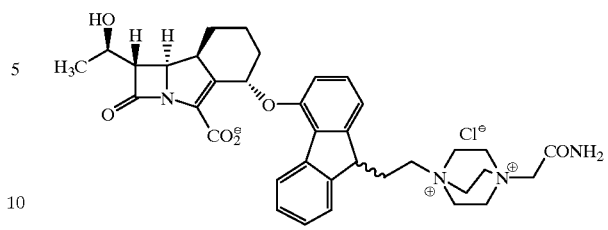

Following the procedure outlined in preparative example 36, with the phenol prepared in preparative example 15, and subsequently following the processes of preparative examples 37–40, and example 1, the product depicted is prepared.

EXAMPLE 7

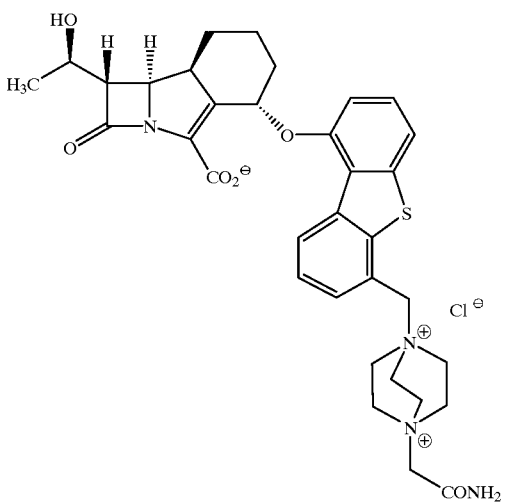

Following the procedure outlined in preparative example 36, with the phenol prepared in preparative example 7, and subsequently following the processes of preparative examples 37–40, and example 1, the product depicted is prepared.

EXAMPLE 8

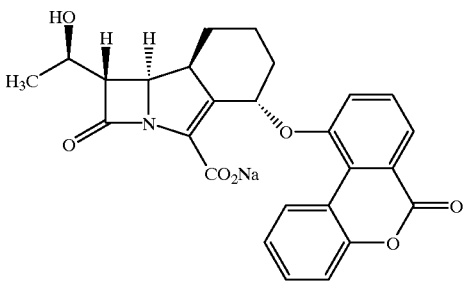

Following the procedure outlined in preparative example 36, with the phenol prepared in preparative example 20, and subsequently following the process of example 1, except that the purification is by reverse phase plate layer chromatography, the product depicted is prepared.

What is claimed is:
1. A compound represented by formula I:

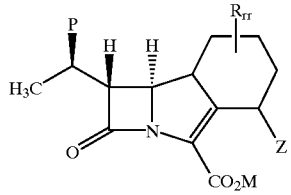

or a pharmaceutically acceptable salt thereof, wherein:
Z represents a*

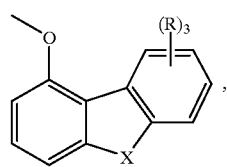

b*

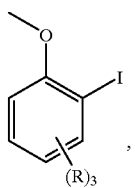

c*

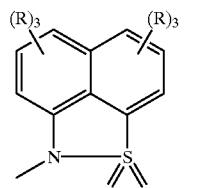

or d*

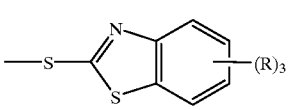

X represents $CH_2$, CHR, C=CHR, O, S, SO, $SO_2$, CO, $CO_2$, OCO, or NR;

$CO_2M$ represents a carboxylic acid, a carboxylate anion counter balanced by a counterion, or a pharmaceutically acceptable ester group;

Rrr represents hydrogen, —$C_{1-6}$ straight- or branched-chain alkyl, unsubstituted or substituted with one to four $R^i$ groups;

P represents hydrogen, hydroxyl, or F;

each R is independently selected from: —R*; -Q; hydrogen; halo; —CN; —$NO_2$; —$NR^aR^b$; —$OR^c$; —$SR^c$; —C(O)$NR^aR^b$; —C(O)$OR^h$; —S(O)$R^c$; —$SO_2R^c$; —$SO_2NR^aR^b$; —$NR^aSO_2R^b$; —C(O)$R^a$; —OC(O)$R^a$; —OC(O)$NR^aR^b$; —$NR^aC(O)NR^bR^c$; —$NR^aCO_2R^h$; —$OCO_2R^h$; —$NR^aC(O)R^b$; —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups;

with the proviso that at least one R is present which contains at least one positive charge which is counter balanced by at least one L– and/or with $CO_2M$ as a carboxylate anion, but there can be no more than three cationic centers, counter balanced by the appropriate number of counterions;

each $R^a$, $R^b$ and $R^c$ independently represents hydrogen, —R*, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^e COR^f$; —$OCOR^e$; —$OCONR^eR^f$; —$NR^eCONR^fR^g$; —$NR^eCO_2R^h$; —$OCO_2R^h$; —C($NR^e$)$NR^fR^g$; —$NR^eC(NH)NR^fR^g$; —$NR^eC(NR^f)R^g$; —R* or -Q;

$R^e$, $R^f$ and $R^g$ represent hydrogen; —R*; —$C_{1-6}$ straight- or branched-chain alkyl unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —$N^+(R^h)_3$; —C(O)$N(R^h)_2$; —$SO_2N(R^h)_2$; heteroaryl; heteroarylium; —$CO_2R^h$; —C(O)$R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3$–$C_6$ cycloalkyl group or phenyl;

Q is selected from the group consisting of:

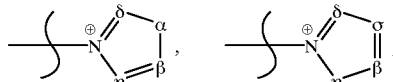

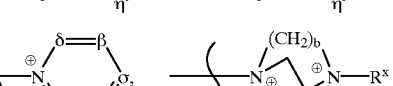

wherein:
a and b are 1, 2 or 3;
L⁻ is a pharmaceutically acceptable negatively charged counterion;
L⁺ is a pharmaceutically acceptable negatively charged counterion;
α represents O, S or $NR^s$;
β, δ, λ, μ and σ represent $CR^t$, N or $N^+R^s$, provided that no more than one of β, δ, λ, μ and σ is $N^+R^s$;
R* is selected from the group consisting of:

wherein:
d represents O, S or $NR^k$;
e, g, x, y and z represent $CR^m$, N or $N^+R^k$, provided that no more than one of e, g, x, y and z in any given structure represents $N^+R^k$;

$R^k$ represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;

each $R^m$ independently represents a member selected from the group consisting of: hydrogen; halo; —CN; —$NO_2$; —$NR''R^o$; —$OR''$; —$SR''$; —$CONR''R^o$; —$COOR^h$; —$SOR''$; —$SO_2R''$; —$SO_2NR''R^o$; —$NR''SO_2R^o$; —$COR''$; —$NR''COR^o$; —$OCOR''$; —$OCONR''R^o$; —$NR''CO_2R^h$; —$NR''CONR^oR^h$; —$OCO_2R^h$; —$CNR''NR^oR^h$; —$NR''CNHNR^oR^h$; —$NR''C(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;

$R^n$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR''R^v$; —$OR''$; —$SR''$; —$CONR''R^v$; —$COOR^h$; —$SOR''$; —$SO_2R''$; —$SO_2NR''R^v$; —$NR''SO_2R^v$; —$COR''$; —$NR''COR^v$; —$OCOR''$; —$OCONR''R^v$; —$NR''CO_2R^v$; —$NR''CONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

$R^x$ represents hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, phenyl or heteraryl, said phenyl and heteroaryl being optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—.

2. A compound in accordance with claim 1 wherein $CO_2M$ represents a carboxylate anion counter balanced by a counterion.

3. A compound in accordance with claim 1 wherein one R represents a group which contains a positively charged moiety, and the remaining R groups are selected from hydrogen and $C_{1-6}$ straight or branched chain alkyl, unsubstituted or substituted with one to four $R^d$ groups.

4. A compound in accordance with claim 3 wherein one R represents a group containing a positively charged moiety and the remaining R groups are hydrogen.

5. A method of treating or preventing a bacterial infection in a mammalian patient in need thereof, comprising administering to said patient an effective amount of a compound of claim 1.

6. A compound in accordance with claim 1 wherein the R groups contain two positive charges, one of which is the counterion for the carboxylate anion and the other is a negatively charged counterion.

7. A compound in accordance with claim 1 wherein one R group represents a —$C_{1-6}$ straight or branched chain alkyl group, substituted with one to four $R^d$ groups, wherein one $R^d$ group represents —$R^*$ or Q.

8. A compound in accordance with claim 1 wherein Q is selected from the group consisting of:

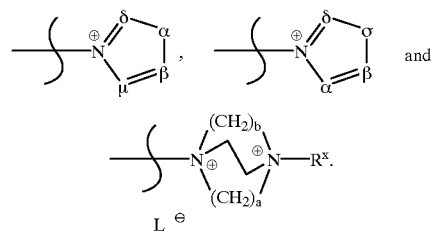

9. A compound in accordance with claim 8 wherein wherein Q represents:

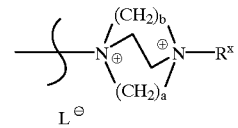

L–, a and b are as originally defined, and $R^x$ represents a member selected from the group consisting of: hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^W$, $NR^hR^W$, $N^+(R^h)_2R^W$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, phenyl, or heteroaryl, said phenyl and heteroaryl being optionally substituted with from one to four $R^i$ groups or with one to two $C_{1-3}$ straight- or branched-chain alkyl groups, said alkyl groups being unsubstituted or substituted with one to four $R^i$ groups, and $R^h$, $R^i$ and $R^w$ are as originally defined.

10. A compound in accordance with claim 1 wherein Q represents —$N^+R^xR^yR^z$, wherein $R^x$, $R^y$ and $R^z$ are as originally defined.

11. A compound in accordance with claim 1 wherein one $R^*$ group is present and is selected from:

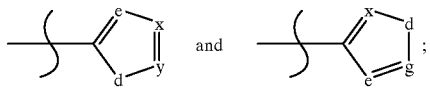

d represents NR$^k$; R$^k$ represents —C$_{1-6}$ straight or branched chain alkyl; and e, g, x and y represent CR$^m$ or N$^+$R$^k$, with R$^k$ as defined above and R$^m$ representing hydrogen.

12. A compound in accordance with claim 1 wherein:

CO$_2$M represents a carboxylate anion counter balanced by a counterion;

one R group which is attached to the naphthosultam platform contains at least one positively charged moiety, and the remaining R groups are selected from hydrogen and C$_{1-6}$ straight or branched chain alkyl, unsubstituted or substituted with one to four R$^d$ groups;

Rd is as originally defined;

R$^h$ represents hydrogen or a C$_{1-6}$ straight or branched chain alkyl group;

Q is selected from the group consisting of:

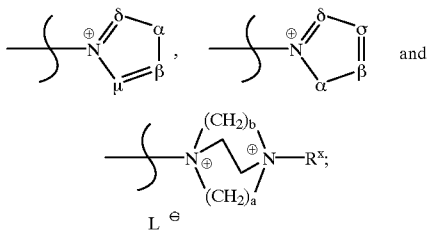

wherein L– is as originally defined; a and b represent 2, and R$^x$ represents a member selected from the group consisting of:

hydrogen or a C$_{1-8}$ straight- or branched-chain alkyl, optionally interrupted or terminated by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, phenyl, or heteroaryl, said phenyl and heteroaryl being optionally substituted with from one to four R$^i$ groups or with one to two C$_{1-3}$ straight- or branched-chain alkyl groups, said alkyl groups being unsubstituted or substituted with one to four R$^i$ groups;

R* is selected from:

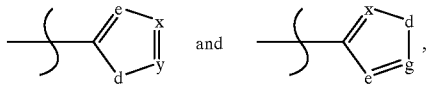

wherein d represents NR$^k$; R$^k$ represents —C$_{1-6}$ straight or branched chain alkyl; and e, g, x and y represent CR$^m$ or N$^+$R$^k$, with R$^k$ as defined above and R$^m$ representing hydrogen.

13. A compound in accordance with claim 1 represented by formula Ia:

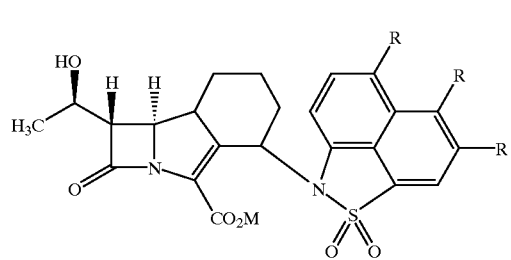

or a pharmaceutically acceptable salt thereof, wherein:

CO$_2$M represents a carboxylate anion counter balanced by a counterion;

one R contains a positively charged moiety, and the other R groups are selected from hydrogen and C$_{1-6}$ straight or branched chain alkyl, unsubstituted or substituted with one to four R$^d$ groups;

R$^d$ is as originally defined;

Q is selected from the group consisting of:

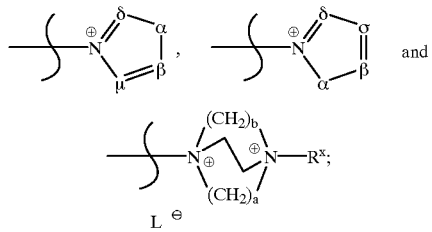

wherein L–, a and b are as originally defined, and R$^x$ represents a member selected from the group consisting of:

hydrogen or a C$_{1-8}$ straight- or branched-chain alkyl, optionally interrupted or terminated by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, phenyl, or heteroaryl, said phenyl and heteroaryl being optionally substituted with from one to four R$^i$ groups or with one to two C$_{1-3}$ straight- or branched-chain alkyl groups, said alkyl groups being unsubstituted or substituted with one to four R$^i$ groups;

R$^h$ represents hydrogen or a C$_{1-6}$ straight or branched chain alkyl group;

R$^w$ is as originally defined;

R* is selected from:

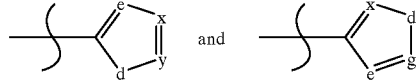

wherein d represents NR$^k$; R$^k$ represents —C$_{1-6}$ straight or branched chain alkyl; and e, g, x and y represent CR$^m$ or N$^+$R$^k$, with R$^k$ as defined above and R$^m$ representing hydrogen.

14. A compound in accordance with claim 1 represented by formula Ib:

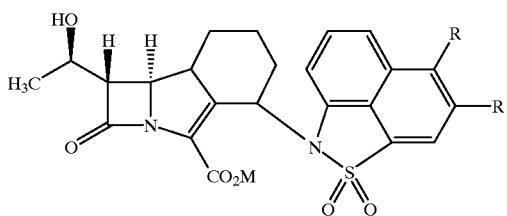

Ib

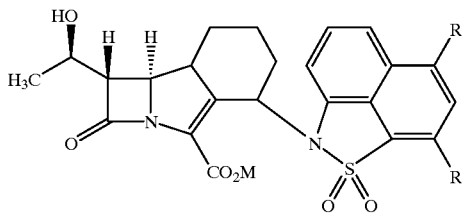

Ic or a pharmaceutically acceptable salt thereof, wherein:
CO₂M represents a carboxylate anion counter balanced by a counterion;
one R group is attached to the naphthosultam platform which contains a positively charged moiety, and the other R group is selected from hydrogen and $C_{1-6}$ straight or branched chain alkyl, unsubstituted or substituted with one to four $R^d$ groups;
$R^d$ is as originally defined;
Q is selected from the group consisting of:

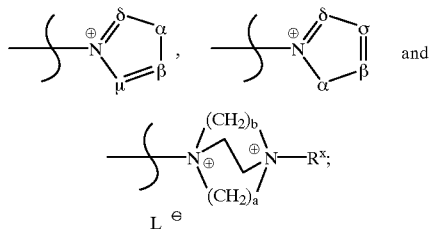

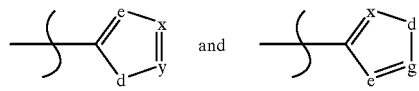

wherein L−, a and b are as originally defined, and $R^x$ represents a member selected from the group consisting of:
hydrogen or a $C_{1-8}$ straight- or branched-chain alkyl, optionally interrupted or terminated by one or two of O, S, SO, SO₂, $NR^w$, $N^+R^hR^w$, or —C(O)—, said chain being unsubstituted or substituted with one to four of halo, CN, NO₂, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, phenyl, or heteroaryl, said phenyl and heteroaryl being optionally substituted with from one to four $R^i$ groups or with one to two $C_{1-3}$ straight- or branched-chain alkyl groups, said alkyl groups being unsubstituted or substituted with one to four $R^i$ groups;
$R^h$ represents hydrogen or a $C_{1-6}$ straight or branched chain alkyl group;
$R^w$ is as originally defined;
R* is selected from:

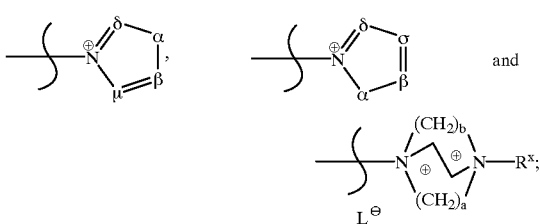

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen. Within this subset, all other variables are as originally defined with respect to formula I.

15. A compound in accordance with claim 1 represented by formula Ic:

or a pharmaceutically acceptable salt thereof, wherein:
CO₂M represents a carboxylate anion counter balanced by a counterion;
one R group is attached to the naphthosultam platform which contains a positively charged moiety, and the other R group is selected from hydrogen, halo and $C_{1-6}$ straight or branched chain alkyl, unsubstituted or substituted with one to four $R^d$ groups;
$R^d$ is as originally defined;
Q is selected from the group consisting of:

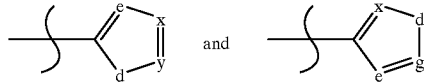

wherein L−, a and b are as originally defined, and $R^x$ represents a member selected from the group consisting of:
hydrogen or a $C_{1-8}$ straight- or branched-chain alkyl, optionally interrupted or terminated by one or two of O, S, SO, SO₂, $NR^w$, $N^+R^hR^w$, or —C(O)—, said chain being unsubstituted or substituted with one to four of halo, CN, NO₂, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, phenyl, or heteroaryl, said phenyl and heteroaryl being optionally substituted with from one to four $R^i$ groups or with one to two $C_{1-3}$ straight- or branched-chain alkyl groups, said alkyl groups being unsubstituted or substituted with one to four $R^i$ groups;
$R^h$ represents hydrogen or a $C_{1-6}$ straight or branched chain alkyl group;
$R^w$ is as originally defined;
R* is selected from:

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

16. A compound in accordance with claim 1 represented by formula Id:

or a pharmaceutically acceptable salt thereof, wherein:

$CO_2M$ represents a carboxylate anion counter balanced by a counterion;

one R group is attached to the naphthosultam platform which contains a positively charged moiety, and the other R group is selected from hydrogen, halo and $C_{1-6}$ straight or branched chain alkyl, unsubstituted or substituted with one to four $R^d$ groups;

$R^d$ is as originally defined;

Q is selected from the group consisting of:

wherein L–, a and b are as originally defined, and $R^x$ represents a member selected from the group consisting of:
    hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl, or heteroaryl, said phenyl and heteroaryl being optionally substituted with from one to four $R^i$ groups or with one to two $C_{1-3}$ straight- or branched-chain alkyl groups, said alkyl groups being unsubstituted or substituted with one to four $R^i$ groups;

$R^h$ represents hydrogen or a $C_{1-6}$ straight or branched chain alkyl group;

$R^w$ is as originally defined;

R* is selected from:

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

17. A compound in accordance with claim 1 represented by formula Ie:

or a pharmaceutically acceptable salt thereof, wherein:

R contains a positively charged moiety selected from the group consisting of:
    R*, Q, and a $C_{1-6}$ straight or branched alkyl chain substituted with one $R^d$ group;

$R^d$ is independently selected —R* or Q;

Q is selected from the group consisting of:

wherein L–, a and b are as originally defined, and $R^x$ represents a member selected from the group consisting of:
    hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl, or heteroaryl, said phenyl and heteroaryl being optionally substituted with from one to four $R^i$ groups or with one to two $C_{1-3}$ straight- or branched-chain alkyl groups, said alkyl groups being unsubstituted or substituted with one to four $R^i$ groups;

R* is selected from:

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

18. A compound in accordance with claim 1 represented by formula If:

If

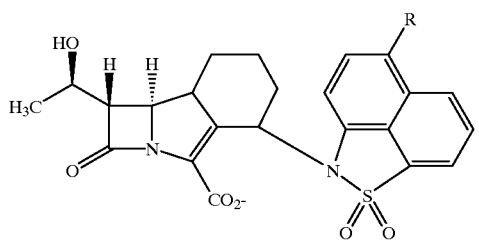

or a pharmaceutically acceptable salt thereof, wherein:
R contains a positively charged moiety selected from the group consisting of: —R*, Q, and a $C_{1-6}$ straight or branched alkyl chain substituted with one $R^d$ group;
$R^d$ is independently selected —R* or Q,
Q is selected from the group consisting of:

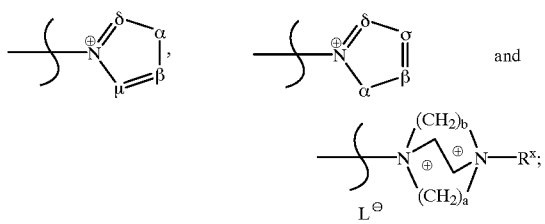

wherein L–, a and b are as originally defined, and $R^x$ represents a member selected from the group consisting of:
hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl, or heteroaryl, said phenyl and heteroaryl being optionally substituted with from one to four $R^i$ groups or with one to two $C_{1-3}$ straight- or branched-chain alkyl groups, said alkyl groups being unsubstituted or substituted with one to four $R^i$ groups;
R* is selected from:

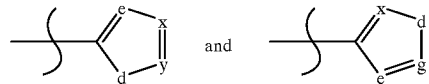

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.
19. A compound in accordance with claim 17 wherein:
R represents

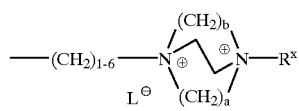

and $R^x$, a, b and L– are as originally defined.

20. A compound in accordance with claim 1 represented by formula Ig:

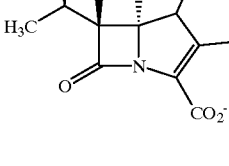

wherein:
R represents

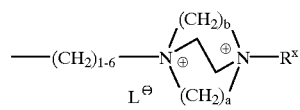

and $R^x$, a, b and L– are as originally defined.
21. A compound in accordance with claim 1 falling within one of the following tables:

TABLE

| # | Q |
|---|---|
| 27 | 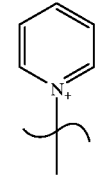 |
| 28 | 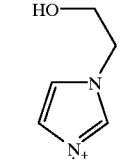 |
| 29 | 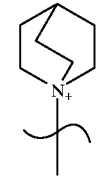 |

TABLE-continued
| # | Q |
|---|---|
| 30 | 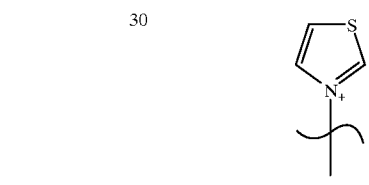 |
| 31 | 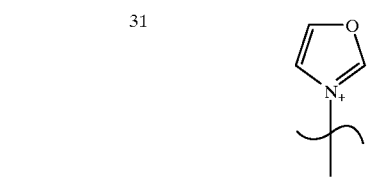 |
| 32 | 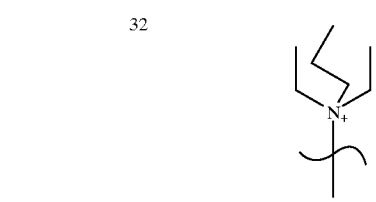 |
| 33 | 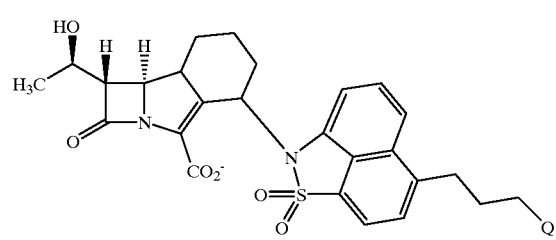 |
| 34 | 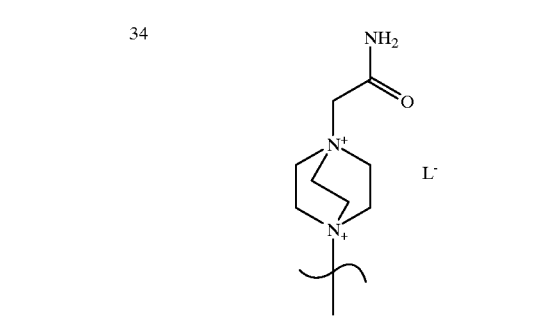 |
| 35 | 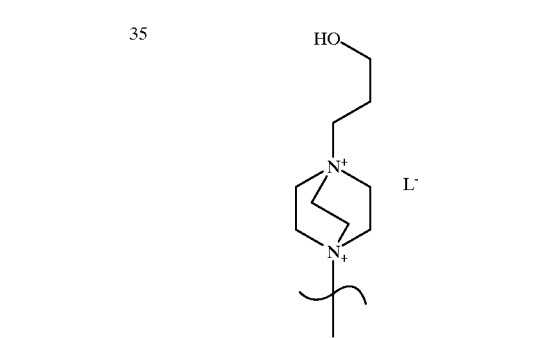 |
TABLE-continued
| # | Q |
|---|---|
| 36 | 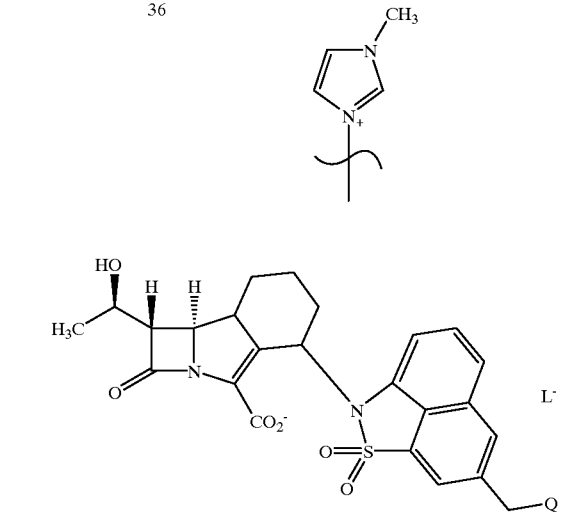 |
| 37 |  |
| 38 | 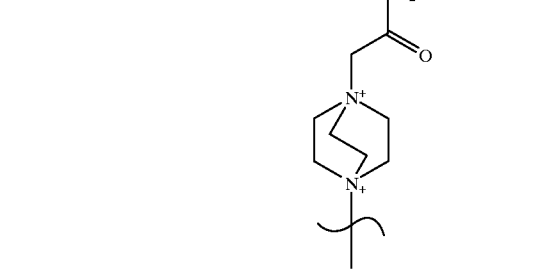 |
| 39 |  |
| 40 |  |

TABLE-continued

| # | Q |
|---|---|
| 41 | (1-methylimidazolium attached via N) |
| 42 | (1-(2-hydroxyethyl)imidazolium) |
| 43 | (thiazolium) |
| 45 | (carbamoylmethyl-DABCO, L⁻) |
| 46 | (3-hydroxypropyl-DABCO, L⁻) |
| 47 | (1-methylimidazolium) |
| 49 | (carbamoylmethyl-DABCO) |
| 50 | (3-hydroxypropyl-DABCO) |

(Entries 40, 44, and 48 show the tricyclic β-lactam carboxylate core bearing a naphthosultam N-substituent with a —CH₂Q, —CH₂CH₂Q, or —CH₂Q group respectively.)

TABLE-continued
| # | Q |
|---|---|
| 51 | 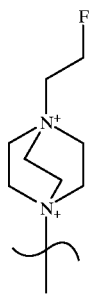 |
|  | 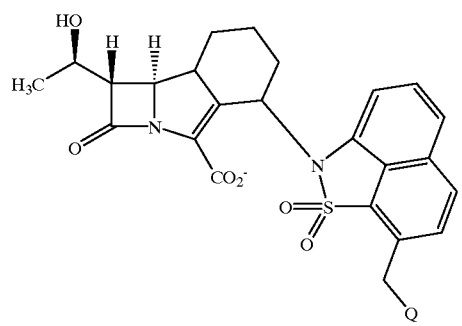 |
| 52 | 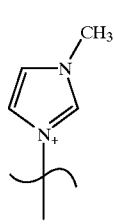 |
| 53 | 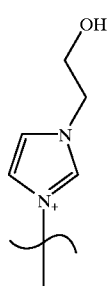 |
| 54 | 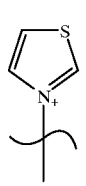 |
TABLE-continued
| # | Q |
|---|---|
|  | 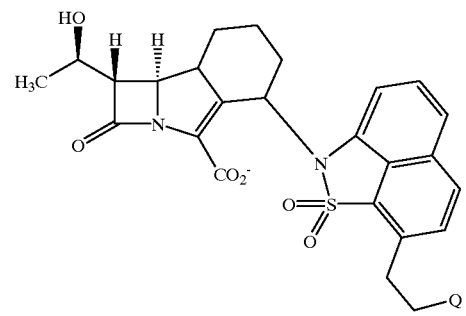 |
| 56 | 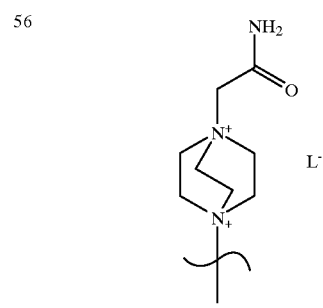 |
| 57 | 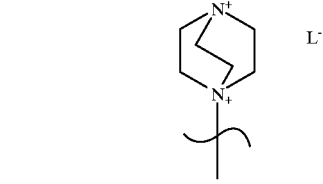 |
| 58 | 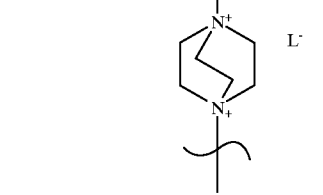 |
|  | 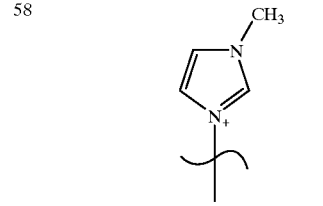 |
|  | 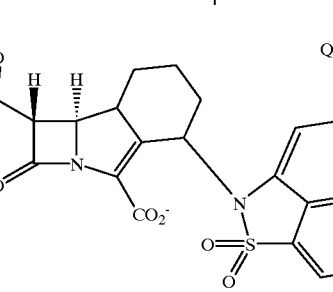 |

TABLE-continued
| # | Q |
|---|---|
| 60 | 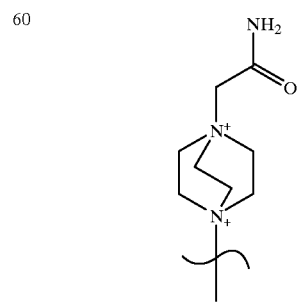 |
| 61 | 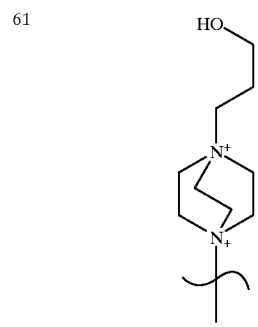 |
| 62 | 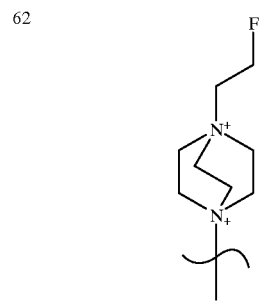 |
| | 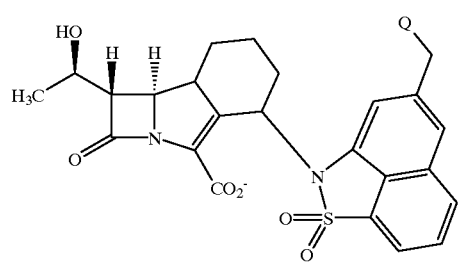 |
| 63 | 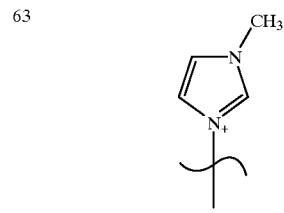 |
TABLE-continued
| # | Q |
|---|---|
| 64 | 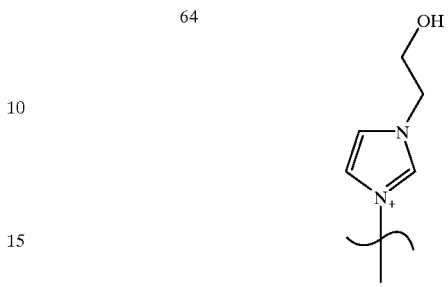 |
| 65 | 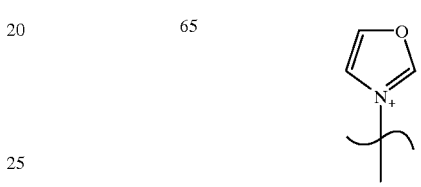 |
| | 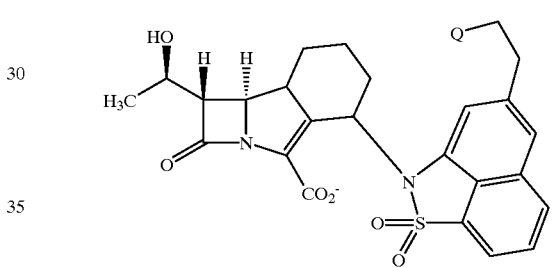 |
| 67 | 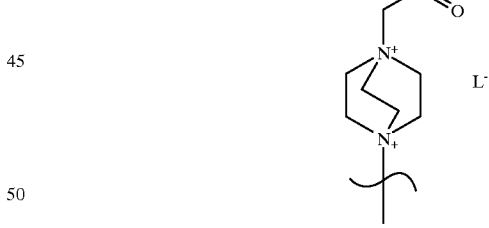 |
| 68 |  |

TABLE-continued

| # | Q |
|---|---|
| 69 | 1-methylimidazolium-CH₂- |
| 74 | 1-methylimidazolium-CH₂- |
| 75 | 1-(2-hydroxyethyl)imidazolium-CH₂- |
| 76 | oxazolium-CH₂- |

TABLE-continued

| # | Q |
|---|---|
| 78 | 1-(carbamoylmethyl)-4-aza-1-azoniabicyclo[2.2.2]octane, L⁻ |
| 79 | 1-(3-hydroxypropyl)-4-aza-1-azoniabicyclo[2.2.2]octane, L⁻ |
| 80 | 1-methylimidazolium-CH₂- |
| 82 | 1-(carbamoylmethyl)-4-aza-1-azoniabicyclo[2.2.2]octane, L⁻ |

TABLE-continued

| # | Q |
|---|---|
| 83 | (structure) |
| 84 | (structure) |
| 85 | (structure) |
| 86 | (structure) |
| 87 | (structure) |
| 88 | (structure) |
| 89 | (structure) |
| 90 | (structure) |
| 91 | (structure) |
| 92 | (structure) | wherein L− represents a pharmaceutically acceptable counterion.

22. A compound of structural formula:
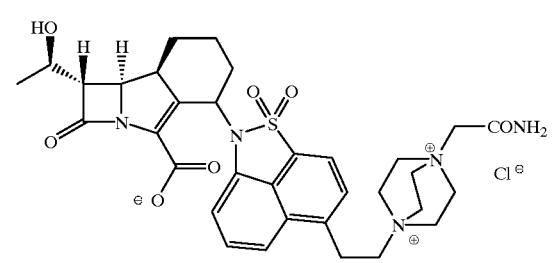
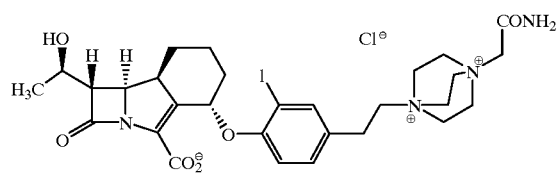
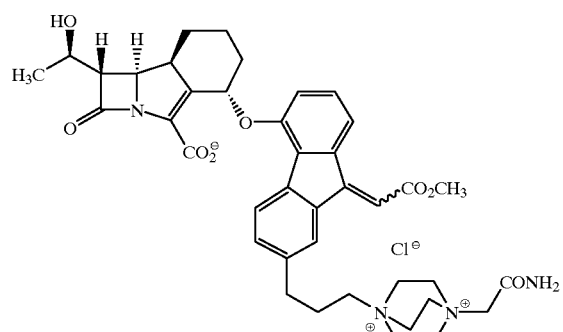
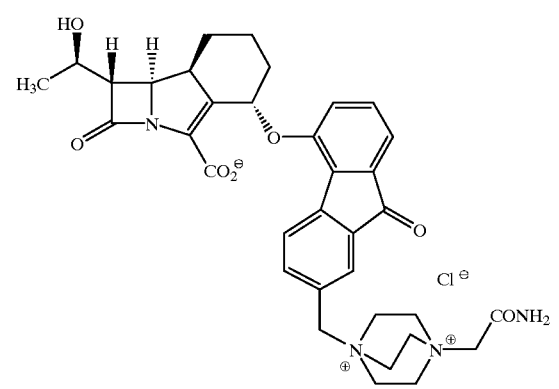
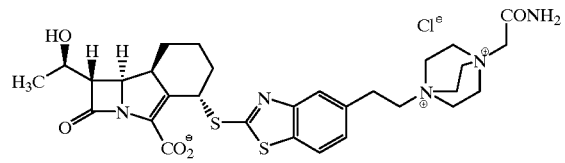
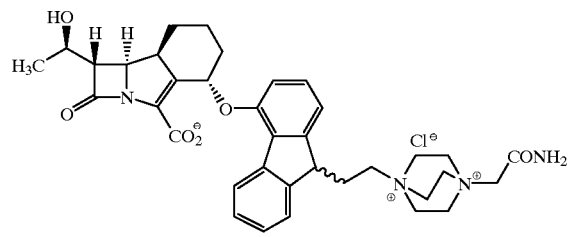
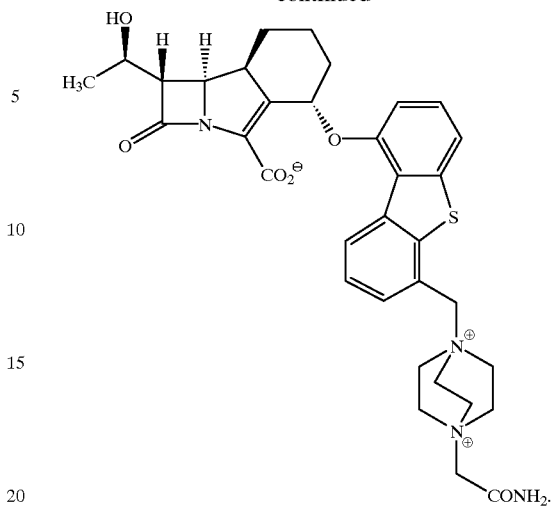
-continued
23. A pharmaceutical composition comprised of a compound in accordance with claim 1 in combination with a pharmaceutically acceptable carrier.
24. A compound in accordance with claim 1 represented by the structural formula:
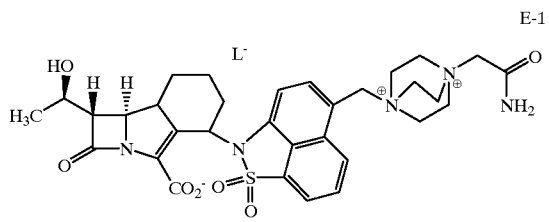
E-1
and
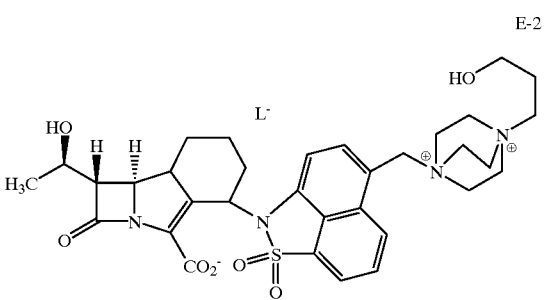
E-2
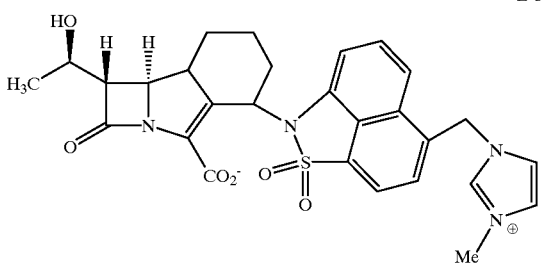
E-3
and E-4
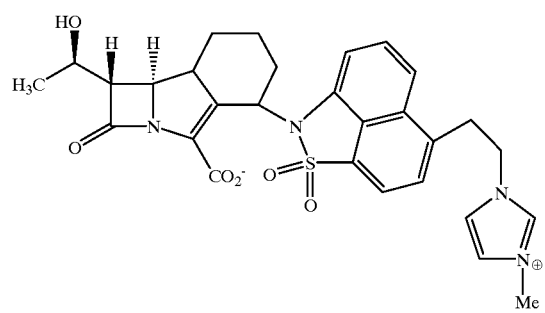
E-5
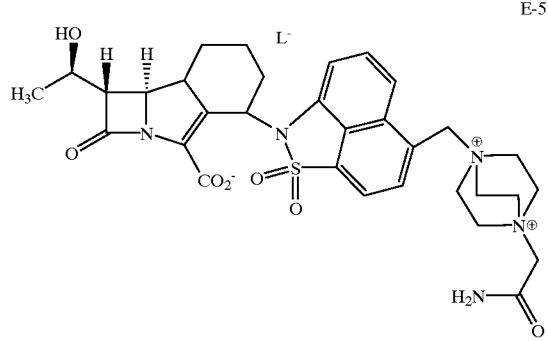
and
E-7
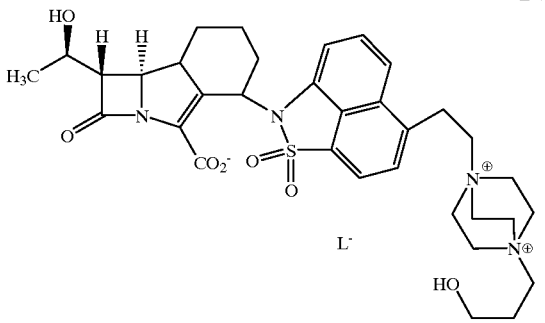
E-6
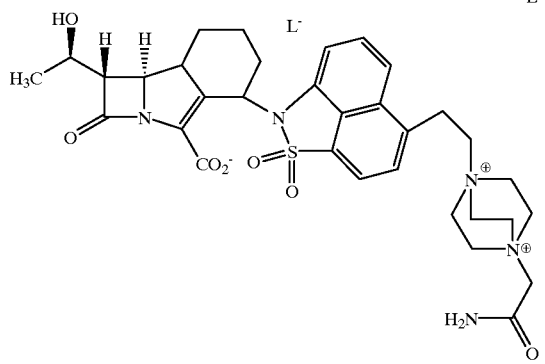
and
E-8
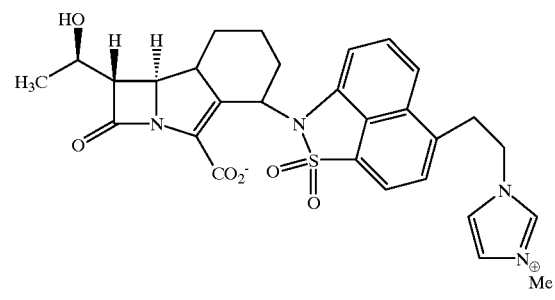
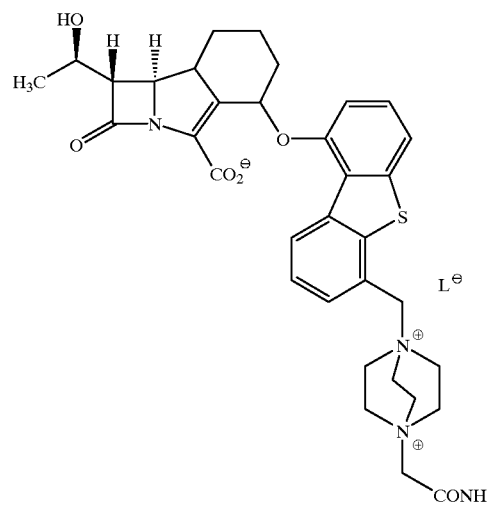
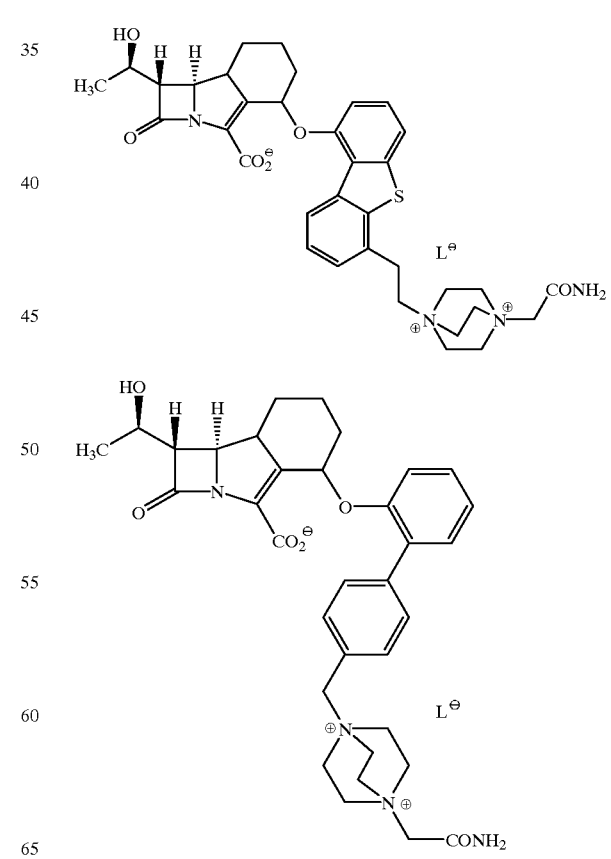

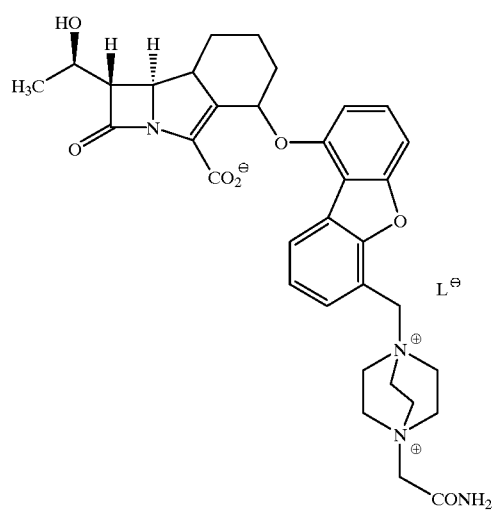
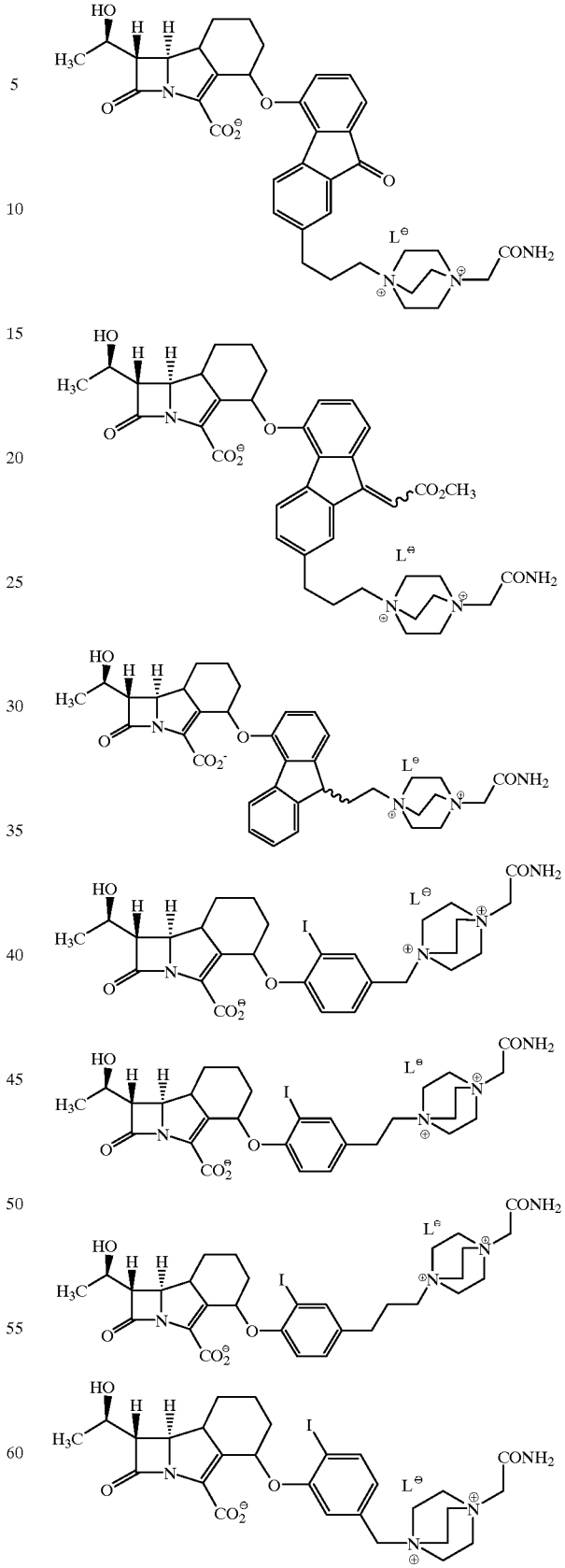

-continued
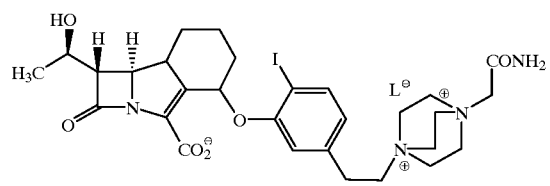
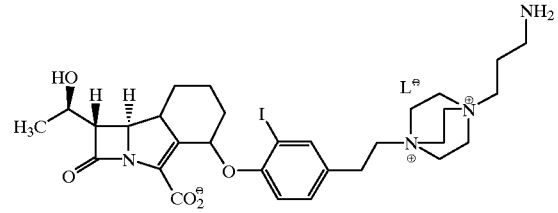
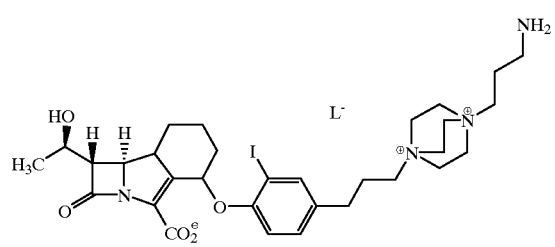
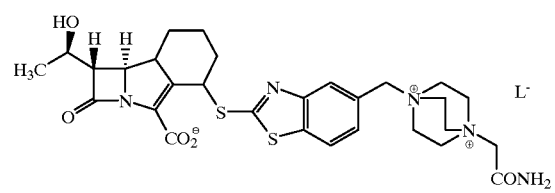
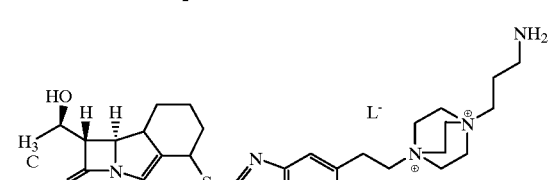
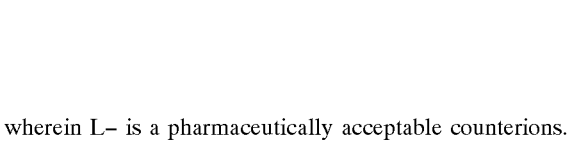
wherein L– is a pharmaceutically acceptable counterions.
25. A compound in accordance with claim 1 represented by the structural formula:
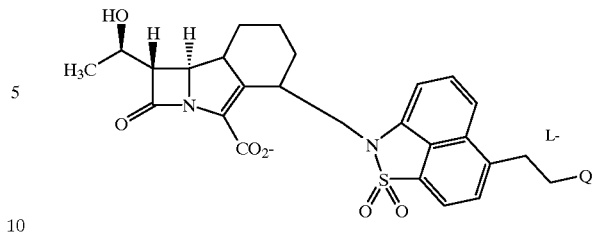
wherein Q is
| # | Q |
|---|---|
| 9 | 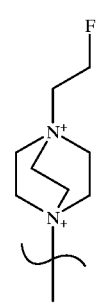 |
| 10 | |
| 11 | 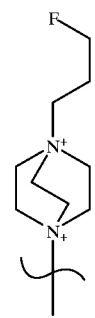 |
| 12 | |
TABLE TABLE-continued
| # | Q |
|---|---|
| 13 | 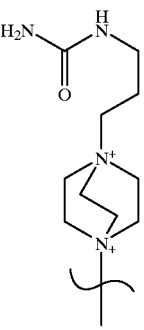 |
| 14 | 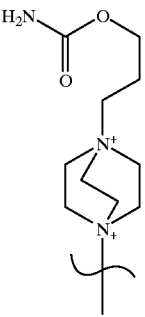 |
| 15 | 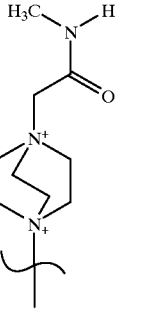 |
| 16 | 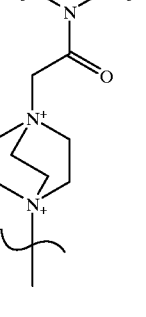 |
| 17 | 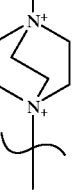 |
| 18 | 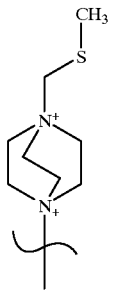 |
| 19 | 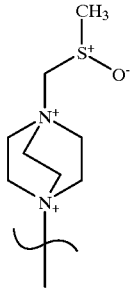 |
| 20 | 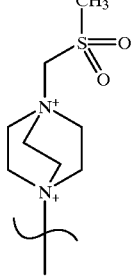 |
| 21 | 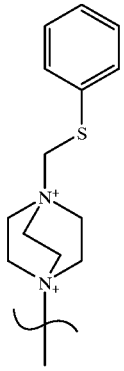 |

TABLE-continued
| # | Q |
|---|---|
| 22 | 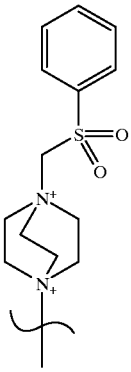 |
| 23 | 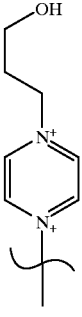 |
| 24 | 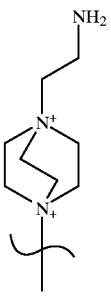 |
| 25 | 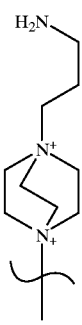 |
TABLE-continued
| # | Q |
|---|---|
| 26 | 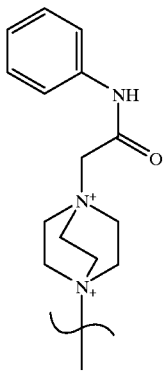 |
Ph = phenyl
and L− is a pharmaceutically acceptable counterion.
26. A compound represented by the structure:
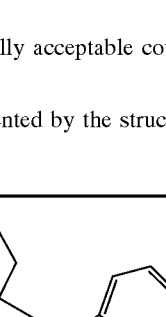
| R₂ | Q |
|---|---|
| Cl | 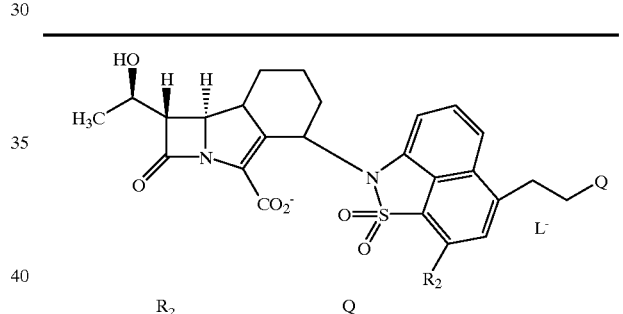 |
| CH₃ | 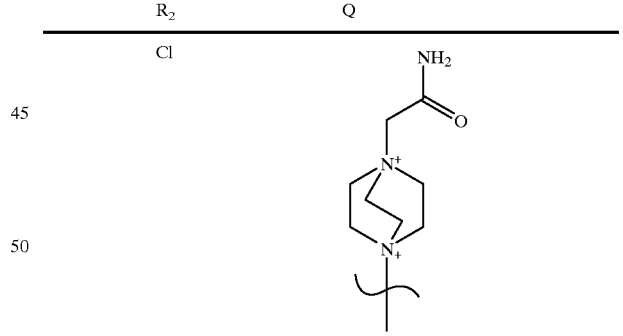 |

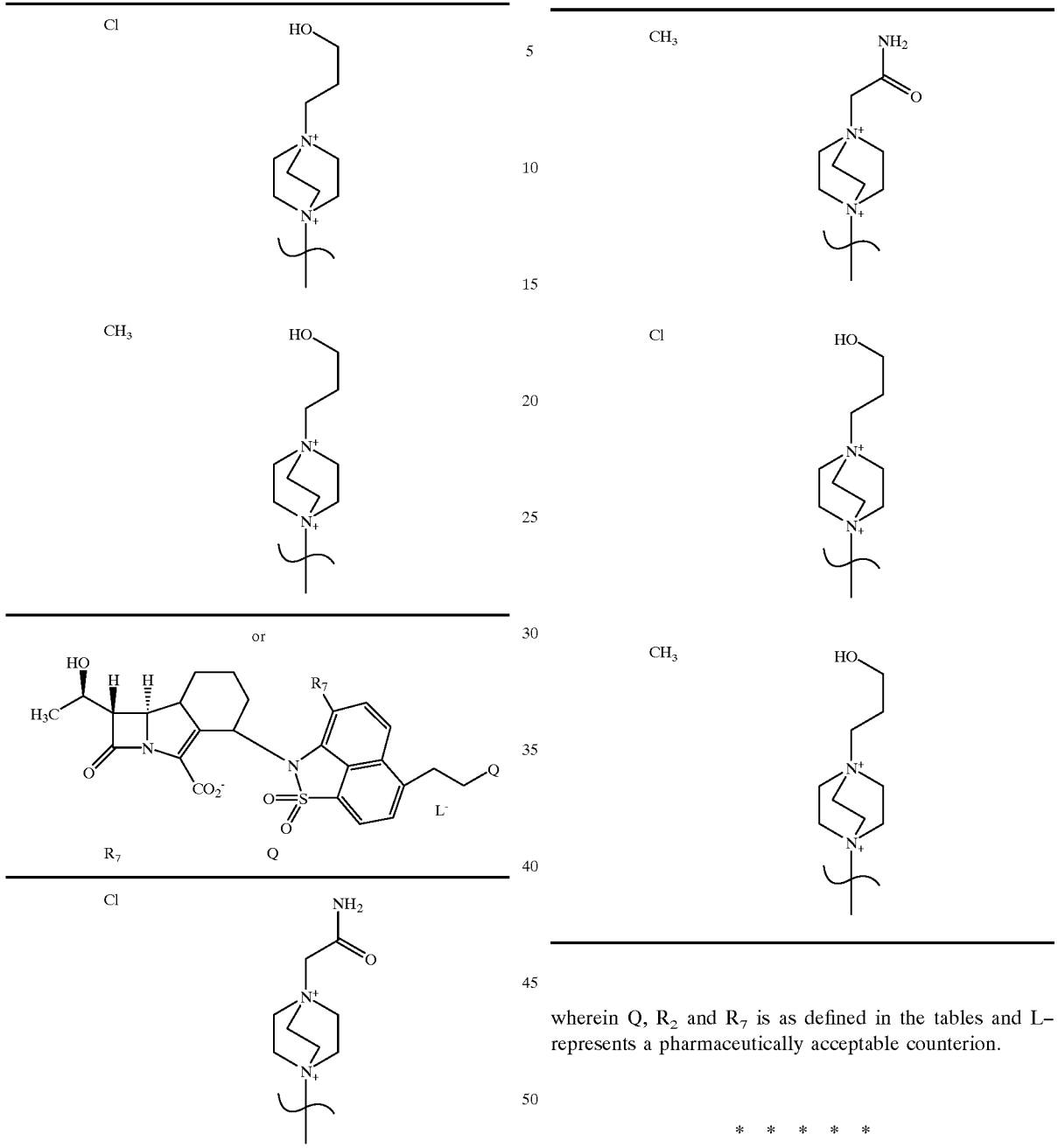
wherein Q, $R_2$ and $R_7$ is as defined in the tables and L− represents a pharmaceutically acceptable counterion.
* * * * *